US007709620B2

(12) United States Patent
Hucul et al.

(10) Patent No.: US 7,709,620 B2
(45) Date of Patent: May 4, 2010

(54) NON-RIBOSOMAL PEPTIDE SYNTHETASES AND ASSOCIATED BIOSYNTHETIC GENES

(75) Inventors: John A. Hucul, New City, NY (US); Nathan Magarvey, Jamaica Plain, MA (US); Michael Greenstein, Peoria, IL (US)

(73) Assignee: Wyeth, Madison, NJ (US)

( * ) Notice: Subject to any disclaimer, the term of this patent is extended or adjusted under 35 U.S.C. 154(b) by 503 days.

(21) Appl. No.: 11/687,152

(22) Filed: Mar. 16, 2007

(65) Prior Publication Data

US 2007/0172909 A1 Jul. 26, 2007

Related U.S. Application Data

(60) Division of application No. 10/746,795, filed on Dec. 23, 2003, now Pat. No. 7,195,907, which is a continuation-in-part of application No. 10/402,842, filed on Mar. 28, 2003, now abandoned.

(60) Provisional application No. 60/368,713, filed on Mar. 29, 2002.

(51) Int. Cl.

| | |
|---|---|
| *C12N 15/52* | (2006.01) |
| *C12N 9/00* | (2006.01) |
| *C12N 15/74* | (2006.01) |
| *C12N 15/76* | (2006.01) |
| *C12N 1/21* | (2006.01) |
| *C07H 21/04* | (2006.01) |

(52) U.S. Cl. .................. 536/23.2; 435/183; 435/252.3; 435/252.33; 435/252.35; 435/320.1; 536/23.7

(58) Field of Classification Search ...................... None
See application file for complete search history.

(56) References Cited

FOREIGN PATENT DOCUMENTS

| | | |
|---|---|---|
| EP | 1262562 | 12/2002 |
| WO | WO 00/40704 | 7/2000 |
| WO | WO 02/24736 | 3/2002 |
| WO | WO 02/077179 | 10/2002 |
| WO | WO 02/101051 | 12/2002 |

OTHER PUBLICATIONS

Marahiel et al., Chem Rev. 1997; 97: 2651-73###.
Stachelhaus et al., Chemistry and Biology 1999; 6:493-505.

*Primary Examiner*—Nashaat T Nashed
*Assistant Examiner*—William W Moore
(74) *Attorney, Agent, or Firm*—Darby & Darby PC

(57) ABSTRACT

The present invention describes the identification of novel non-ribosomal peptide synthetases and associated biosynthetic genes from *Streptomyces hygroscopicus*. The present invention further provides methods for generating novel compounds, such as antibiotics, from these synthetases and associated genes.

10 Claims, 9 Drawing Sheets

AC98-1 R =

AC98-2 R = OH

AC98-3 R =

$R^1$ and $R^2$ = H $R^3$ =

AC98-4 R =

$R^1$ and $R^3$ = H $R^2$ =

AC98-5

$R^2$ and $R^3$ = H $R^1$ =

AC98 BIOSYNTHETIC GENE CLUSTER
*Streptomyces hygroscopicus* NS17
48.2Kb mmpA Module 1 Adenylation domain: Two-Dimensional Representation of Binding Pocket L-Serine Activation mmpA Module 2 Adenylation domain:
Two-Dimensional Representation of Binding Pocket

Glycine Activation mmpA Module 3 Adenylation domain: Two-Dimensional Representation of Binding Pock

Phenylalanine Activation mmpB Module 1 Adenylation domain: Two-Dimensional Representation of Binding Pocket

Tyrosine Activation mmpB Module 2 Adenylation domain: Two-Dimensional Representation of Binding Pocket Cyclo-arginine Activation

NON-RIBOSOMAL PEPTIDE SYNTHETASES AND ASSOCIATED BIOSYNTHETIC GENES

This application is a Division of U.S. patent application Ser. No. 10/746,795, filed Dec. 23, 2003, now U.S. Pat. No. 7,195,907, which is a Continuation-In-Part of U.S. patent application Ser. No. 10/402,842, filed on Mar. 28, 2003, now abandoned, which claims the benefit of Provisional Patent Application Ser. No. 60/368,713, filed on Mar. 29, 2002, the disclosures of which are herein incorporated by reference in their entirety.

FIELD OF THE INVENTION

The present invention relates to non-ribosomal peptide synthetases and associated biosynthetic genes. The present invention further relates to methods for generating novel compounds, such as antibiotics, with these synthetases and associated genes.

BACKGROUND OF THE INVENTION

Bioactive molecules that are isolated from plants, bacteria, and fungi are often referred to as natural products. These molecules are synthesized by primary or secondary pathways within the organism or may even be degradation products of another molecule. Many of these molecules have shown a variety of therapeutic uses in humans and other animal species. One of the best known examples is taxol, which was originally isolated from the bark of the Pacific Yew tree. Taxol has been shown to have anti-cancer properties and is currently used in the treatment of breast cancer. Actinomycetes are prolific producers of bioactive small molecules. These molecules may be used chemically as immunosuppressants, antibiotics, and cancer therapeutics. Actinomycetes are Gram-positive bacteria that form long, thread-like branched filaments. The term actinomycetes is used to indicate organisms belonging to Actinomycetales, an Order of the domain Bacteria. The Actinomycetales are divided into 34 Families including Streptomyceteae, to which belongs the Genus *Streptomyces* (Bergey's Manual of Systematic Bacteriology, Second Edition, 2001; George M. Garrity, Editor-in-Chief, Springer Verlag, New York).

Natural products derived from microbial sources primarily belong to three metabolic families: peptides, polyketides, and terpenes. Peptide natural products can be further classified based on their mode of synthesis: ribosomal and non-ribosomal. Non-ribosomal peptides are synthesized on enzymatic thiotemplates termed non-ribosomal peptide synthetases (NRPS). The non-ribosomal peptides encompass a wide range of compounds having diverse activities including, but not limited to, immunosupressive (such as cyclosporin), surfactant (such as surfactin), siderophores (such as enterobactin), virulence factors (such as yersinabactin), antibacterial (such as penicillin and vancomycin), and anti-cancer (such as actinomycin and bleomycin) activities (Weber et al., Current Genomics 1994; 26:120-25; Ehmann et al., Proc. Nat. Acad. Sci. 2000; 97:2509-14; Gehring et al., Biochemistry 1998; 37:11637; Kallow et al., Biochemistry 1998; 37:5947-52; Trauger et al., Proc. Nat. Acad. Sci. 2000; 97:3112-17; Schauweker et al., J. Bacteriology 1999; 27:2468-74; and Shen et al., Bioorganic Chem 1999; 27:155-71). Non-ribosomal peptides typically range in size from 1-11 amino acids and are produced by a variety of microbes including cyanobacteria, actinomycetes and fungi.

In many cases the non-ribosomal peptides contain non-proteogenic amino acids such as norleucine, β-alanine, ornithine, etc., for which biogenesis pathways, which are secondary to primary metabolism, are required and are post-synthetically modified (e.g., hydroxylated or methylated) by tailoring enzymes. As used herein, the term "proteogenic" indicates that the amino acid can be incorporated into a protein in a cell through well-known metabolic pathways. The choice of including a (D)- or (L)-amino acid into a peptide of the present invention depends, in part, on the desired characteristics of the peptide. For example, the incorporation of one or more (D)-amino acids can confer increasing stability on the peptide in vitro or in vivo. As used herein, the term "amino acid equivalent" refers to compounds which depart from the structure of the naturally occurring amino acids, but which have substantially the structure of an amino acid, such that they can be substituted within a peptide that retains biological activity. Thus, for example, amino acid equivalents can include amino acids having side chain modifications and/or substitutions, and also include related organic acids, amides or the like. The term "amino acid" is intended to include amino acid equivalents. The term "residues" refers both to amino acids and amino acid equivalents.

The genes required to make a NRPS and the necessary tailoring enzymes have been shown in all cases to be localized to the chromosome of the producing microbe. NRPSs are modular in nature, where a module may be defined as a segment of the NRPS necessary to catalyze the activation of a specific amino acid and result in the incorporation of that amino acid into a non-ribosomal peptide. A minimal module contains three domains: (1) adenylation domains (about 60 kDa), responsible for selecting and activating an amino acid and transferring the aminoacyl adenylate to a peptidyl carrying center; (2) thiolation domains, also referred to as peptidyl carrier proteins (8-10 kDa), containing a serine residue which is post-translationally modified with a 4-phosphopantetheine group (Ppant) which acts as an acceptor for the aminoacyl adenylate; and (3) condensation domains (50-60 kDa) which catalyze peptide bond-forming chain-translocating steps between an upstream peptidyl-s-Ppant and the downstream aminoacyl-Ppant of the adjacent module (Doekel, S. and Marahiel, M. A. 2000; Chem. Biol. 7:373-384). This minimal module for chain extension is typically repeated within a synthetase and a co-linear relationship exists between the number of modules present and the number of amino acids in the final product with the order of the modules in the synthetase determining the order of the amino acids in the peptide.

There is a continuing need in the art to determine the genes encoding NRPS complexes.

SUMMARY OF THE INVENTION

The present invention provides the nucleic acid and amino acid sequences of a non-ribosomal peptide synthetase (NRPS) complex from *Streptomyces hygroscopicus*. The NRPS described herein is comprised of two components, designated MppA (SEQ ID NO:2) and MppB (SEQ ID NO:4), and contains the sequences required for the biosynthesis of the peptide core of lipoglycopeptide antibiotic AC98.

The present invention also provides characterization of MppA (SEQ ID NO:2) and MppB (SEQ ID NO:4), including the number of modules in each component and the functional domains contained within each module. In particular, MppA (SEQ ID NO:2) is comprised of three modules, each containing an adenylation, thiolation, and condensation domain, and MppB (SEQ ID NO:4) is comprised of two modules, two epimerization domains, and a partial module comprised only of a condensation domain and thiolation domain.

Further provided by the present invention are expression vectors comprising the genes encoding MppA (SEQ ID NO:2) and MppB (SEQ ID NO:4), and host cells transfected with such MppA (SEQ ID NO:2) and/or MppB (SEQ ID NO:4)-encoding vectors.

The present invention also provides nucleic acid and amino acid sequences for several open reading frames (ORFs) encoding associated gene products that modify the amino acids of the core peptide post-biosynthesis, as well as host cells comprising the ORFs.

In yet a further embodiment, the present invention provides a method for producing the NRPS described herein, which method comprises culturing an NPRS-transformed host cell under conditions that provide for expression of MppA (SEQ ID NO:2) and MppB (SEQ ID NO:4).

The present invention further provides a method of producing a cyclic peptide synthesized by of the NRPS comprised of MppA (SEQ ID NO:2) and MppB (SEQ ID NO:4), which peptide is an antibiotic. In a preferred embodiment, the antibiotic is AC98.

Also provided by the present invention are methods of modifying the adenylation domains of NRPS in order to produce an antibiotic having a modified peptide core, and a method for evaluating the structural regions of the modified peptide.

BRIEF DESCRIPTION OF DRAWINGS

FIG. 4A shows the serine-specific binding pocket of the adenylation domain of module 1 within MppA (SEQ ID NO:2). FIG. 4B shows the glycine-specific binding pocket of the adenylation domain of module 2 within MppA (SEQ ID NO:2). FIG. 4C shows the phenylalanine-specific binding pocket of the adenylation domain of module 3 within MppA (SEQ ID NO:2). FIG. 4D shows the tyrosine-specific binding pocket of the adenylation domain of module 1 within MppB (SEQ ID NO:4). FIG. 4E shows the cycloarginine-specific binding pocket of the adenylation domain of module 2 within MppB (SEQ ID NO:4).

DETAILED DESCRIPTION OF THE INVENTION

The following definitions are The following definitions are provided for the full understanding of terms and abbreviations used in this specification.

The abbreviations in the specification correspond to units of measure, techniques, properties or compounds as follows: “min” means minutes, “h” means hour(s), “μL” means microliter(s), “mL” means milliliter(s), “mM” means millimolar, “M” means molar, “mmole” means millimole(s), “kb” means kilobase, “bp” means base pair(s), and “IU” means International Units. “Polymerase chain reaction” is abbreviated PCR; “Reverse transcriptase polymerase chain reaction” is abbreviated RT-PCR; “Estrogen receptor” is abbreviated ER; “DNA binding domain” is abbreviated DBD; “Ligand binding domain” is abbreviated LBD; “Untranslated region” is abbreviated UTR; “Sodium dodecyl sulfate” is abbreviated SDS; and “High Pressure Liquid Chromatography” is abbreviated HPLC.

Figure 1A:
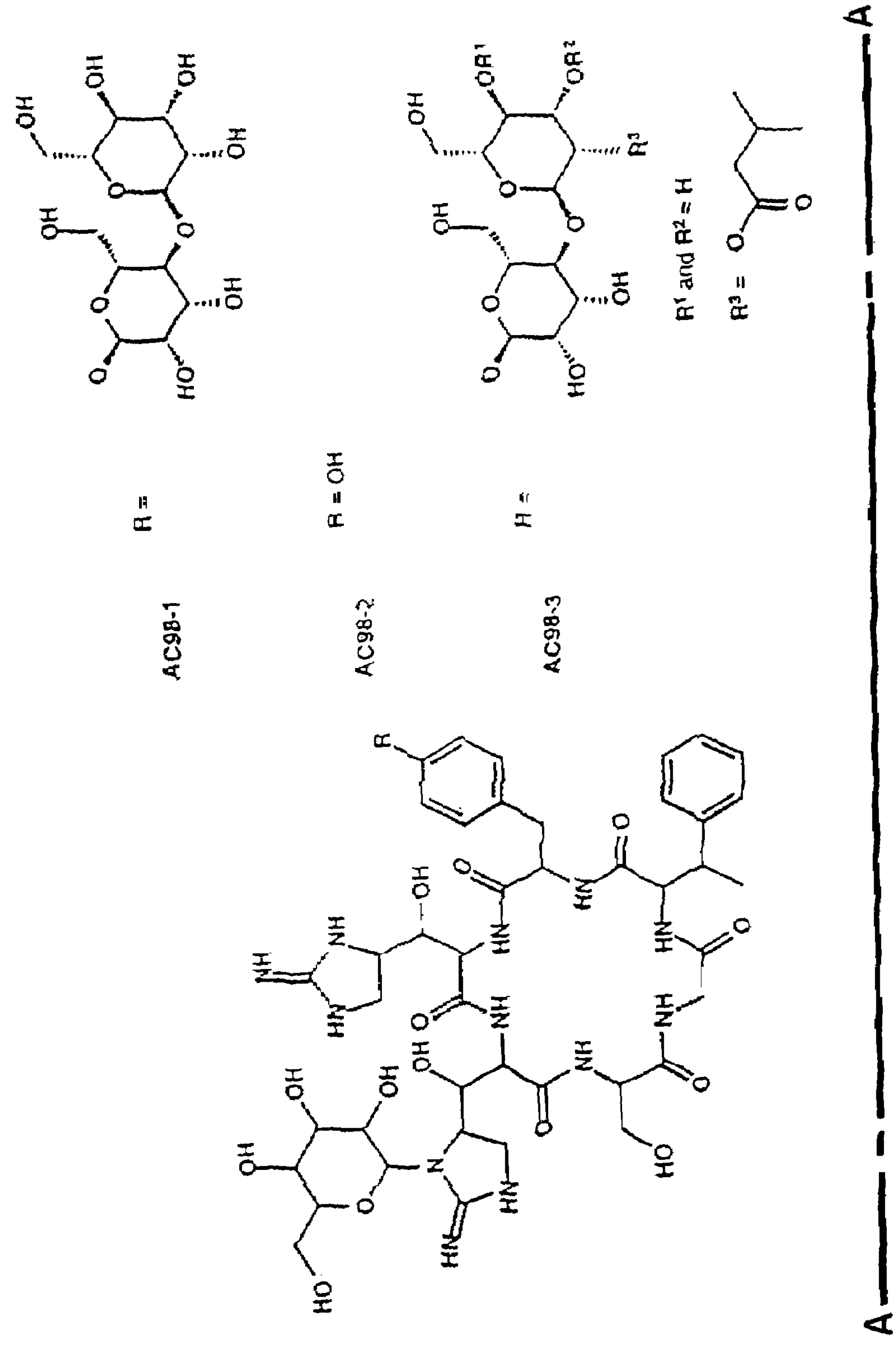
FIGS. 1A-B depict the chemical structures of the lipoglycopeptide antibiotic AC98.
Figure 1:
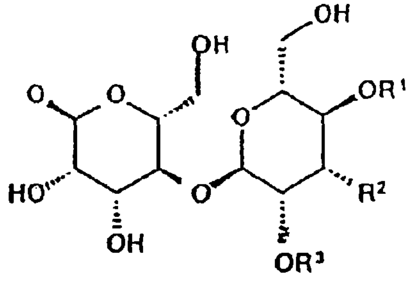
Figure 1:
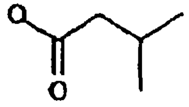
Figure 1:
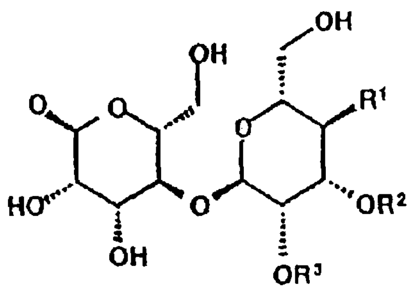
Figure 1:
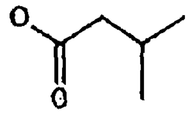
Figure 2:
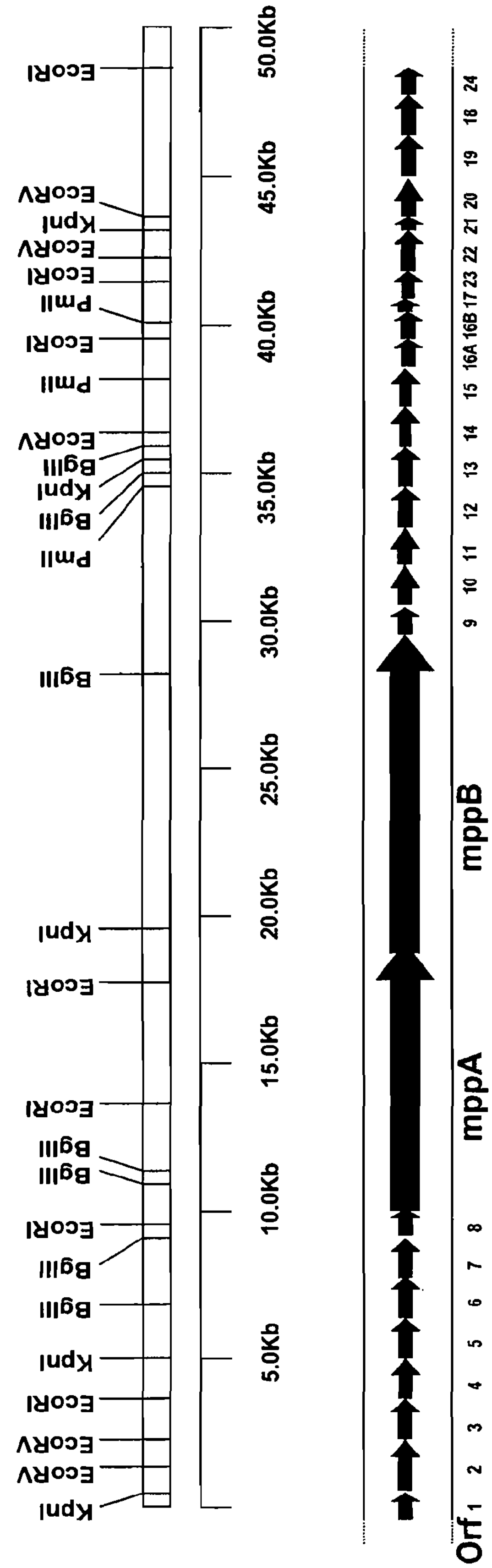
FIG. 2 shows a representation of the NRPS complex from this *Streptomyces hygroscopicus* strain NS17 that is demonstrated to be the minimal biosynthetic machinery responsible for the biosynthesis of the peptide core of AC98.

*Streptomyces hygroscopicus* NS17 is a terrestrial actinomycete which produces a novel lipoglycopeptide antibiotic complex (AC98; See FIG. 1). This strain has been deposited with the Agricultural Research Service Culture Collection, 1815 North University St., Peoria, Ill. 61604, Deposit No. NRRL 30439. This antibiotic has been shown to be active against Gram-positive pathogens including, but not limited to, vancomycin resistant enterococci (VRE), methicillin resistant *Staphlococcus aureus* (MRSA) and *Streptococcus pneumoniae*. The present invention is based on the isolation of the genes encoding a novel NRPS complex from this *Streptomyces* strain that is demonstrated to be the minimal biosynthetic machinery responsible for the biosynthesis of the peptide core of AC98 (see FIG. 2).

Figure 3:
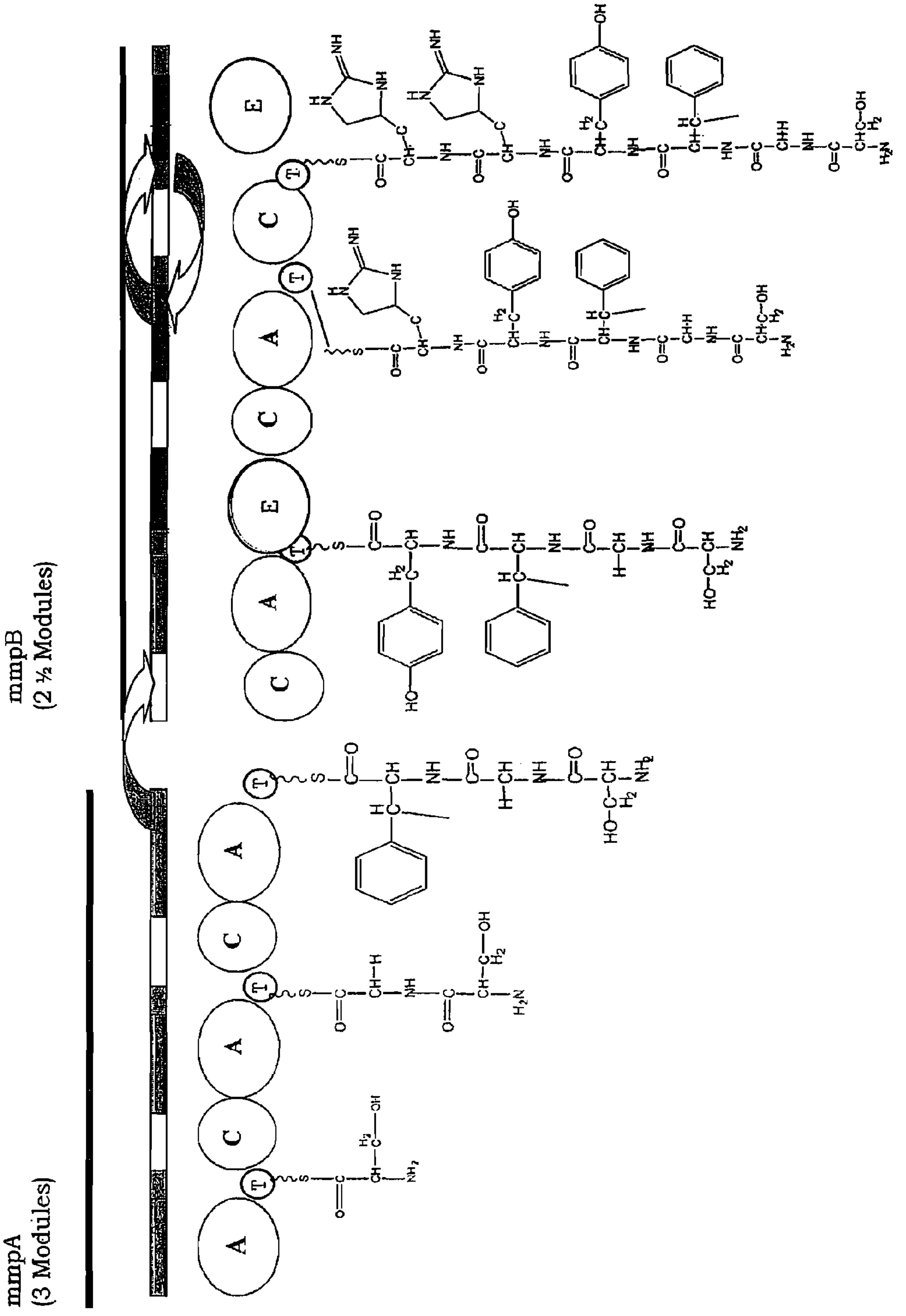
FIG. 3 is a pictorial representation of the biosynthesis of the AC98 peptide core by the novel NRPS described herein.
Figure 4A:
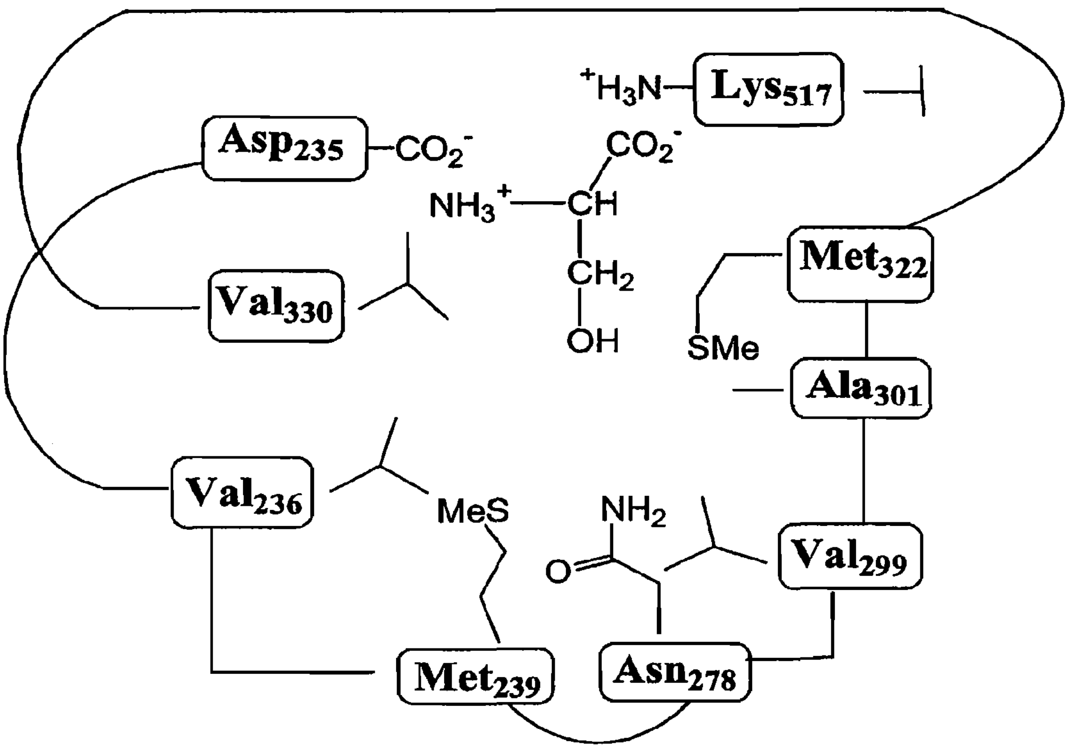
FIG. 4A-E depicts the two-dimensional representation of the binding pockets of adenylation domains within modules of the NRPS of the invention. Amino acid residues 235, 236, 239, 278, 299 & 301, are those that determine the specificity of the binding pocket.
Figure 4B:
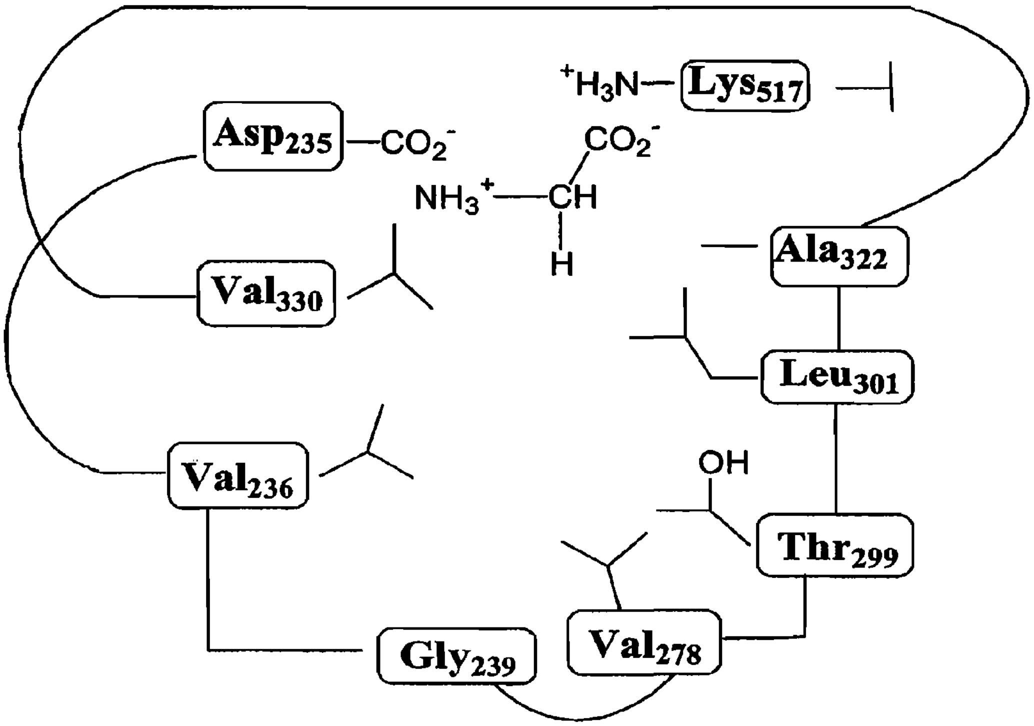
Figure 4C:
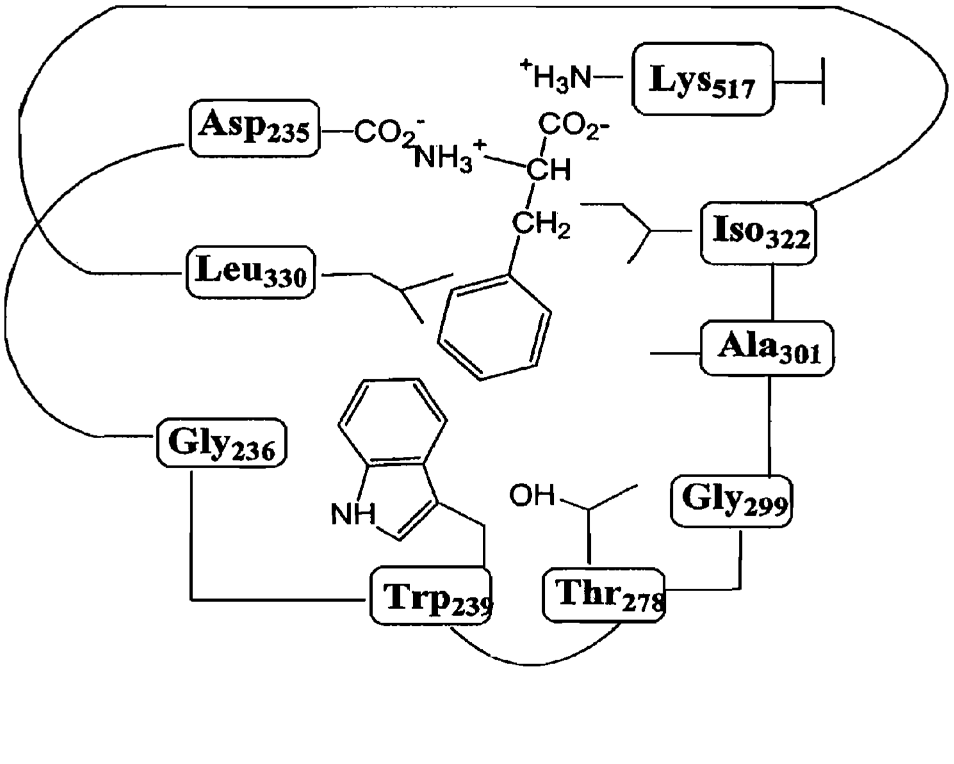
Figure 4D:
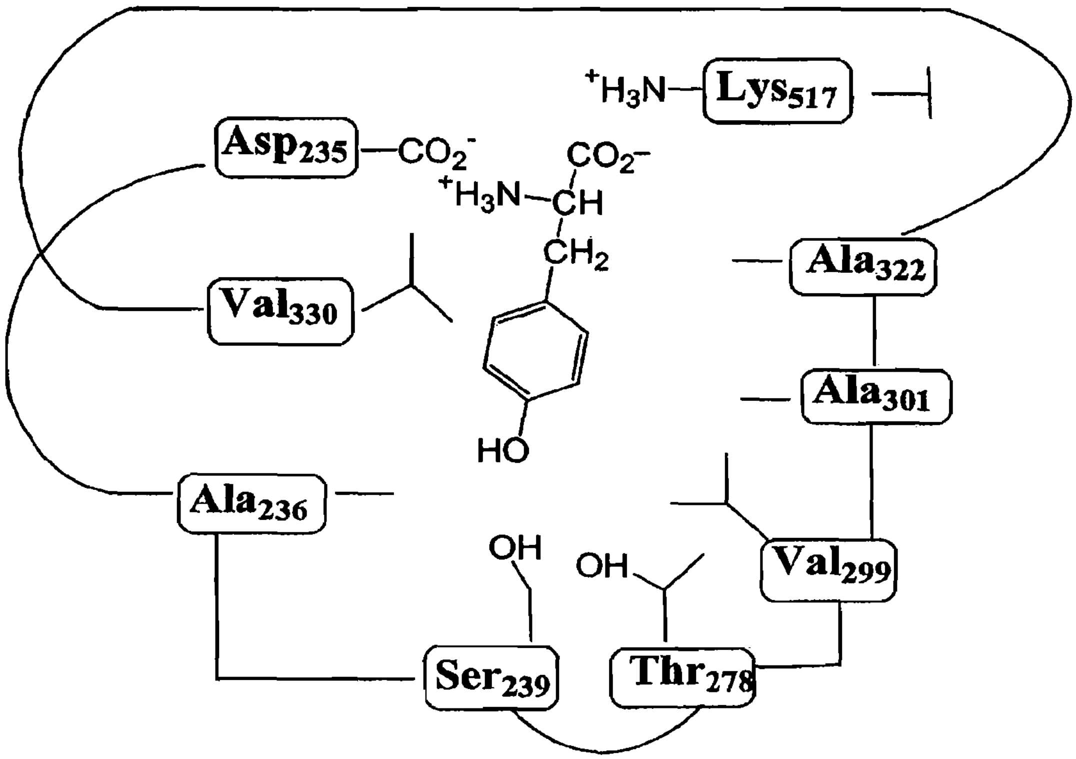
Figure 4E:
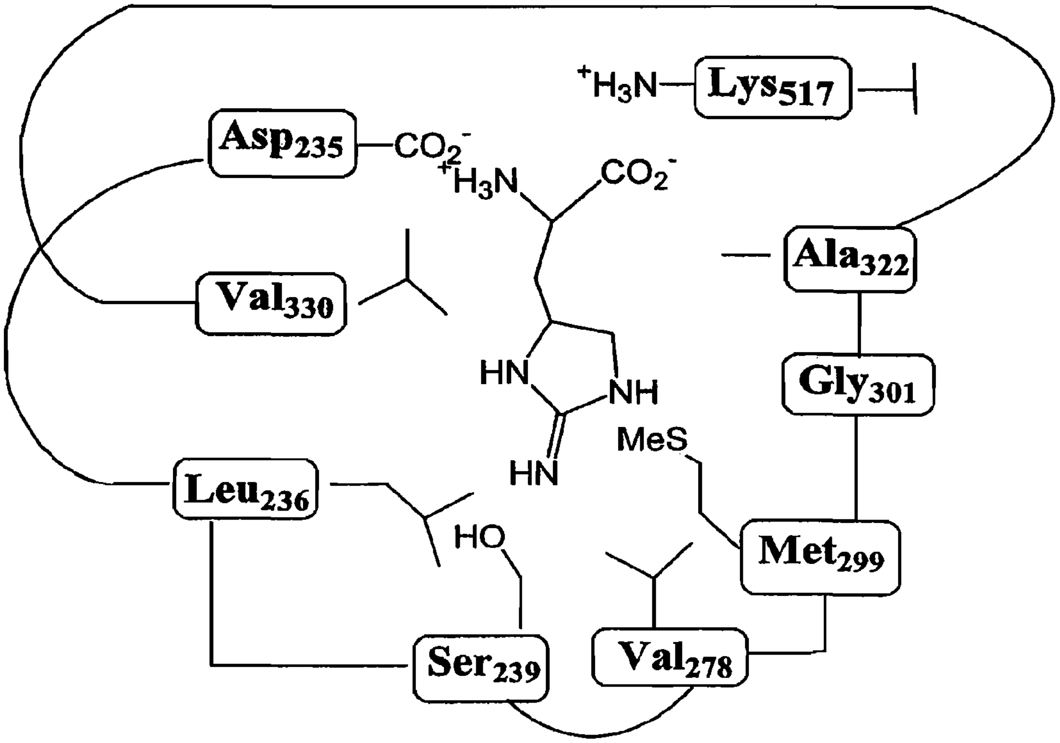

A number of open reading frames (ORFs), that are predicted to play a role in the biosynthesis of AC98, have been isolated and characterized by sequence analysis. Sequence comparisons of specific ORFs indicate that the proteins that are encoded by the ORFs are tailoring enzymes that are involved in such modifications of the peptide core as glycosylation, methylation and acylation. Other ORFs putatively encode enzymes that may be involved in resistance. A detailed description of the NRPS and its function in biosynthesis of the AC98 peptide core is presented in FIG. 3. The genes required to make the NRPS and the necessary tailoring enzymes are localized to the chromosome of the producing microbe.

NRPS

The NRPS enzymes are generally composed of modules where a minimal module contains three domains, an adenylation domain, a thiolation domain, and a condensation domain.

The adenylation domain is typically about 60 kDa. The main function of this domain is to select and activate a specific amino acid as an aminoacyl adenylate. Based on its function, the adenylation domain regulates the sequence of the peptide being produced. Once charged (as an amino acyl adenylate moiety), the amino acid is transferred to a thiolation domain (peptidyl carrying center).

The second domain is the thiolation domain, also referred to as a peptidyl carrier protein. This domain is typically 8-10 kDa and contains a serine residue that is post-translationally modified with a 4-phosphopantetheine group. This group acts as an acceptor for the aminoacyl adenylate moiety on the amino acid. A nucleophilic reaction leads to the release of the aminoacyl adenylate and conjugation of the amino acid to thiolation domain via a thioester bond.

The third domain is the condensation domain. This domain is typically about 50-60 kDa in size. The main function of this domain is to catalyze the formation of a peptide bond between two amino acids. In this reaction an upstream tethered peptidyl group is translocated to the downstream aminoacyl-s-Ppant and linked to the amino acid by peptide bond formation.

This minimal module for chain extension is typically repeated within a synthetase. Additionally, and typically, a co-linear relationship exists between the number of modules present and the number of amino acids in the final product with the order of the modules in the synthetase determining the order of the amino acids in the peptide. This 1:1 relationship, with every amino acid in the product having one module within the enzyme, is referred to as the co-linearity rule. Examples have been found that violate this rule, and in such cases, the NRPS contains more modules than one would expect based on the number of amino acids incorporated in the peptide product (Challis et al., Chem. Biol. 2000; 7:211-24). In some cases the minimal module also is supplemented with additional domains (epimerization, N- or C-methylation, or cyclization domain), with their position in the synthetase determining the substrate upon which they can act. In addition, it has been observed that NRPSs contain inter-domain spacers or linker regions. It has been proposed that these spacers may play a critical role in communication between domains, modules, and even entire synthetases.

There are highly conserved motifs in the catalytic domains of peptide synthetases including: 10 conserved motifs in the adenylation domain; 1 conserved motif in the thiolation domain; 7 conserved motifs in the condensation domain; 1 conserved motif in the thioesterase domain; 7 conserved motifs in the epimerization domains; and 3 conserved motifs in the N-methylation domains. These are detailed in Marahiel et al., Chemical Rev. 1997; 97:2651-73. In addition to modifications such as epimerization, methylation and cyclization during peptide synthesis, post-translational modifications including methylation, hydroxylation, oxidative cross-linking and glycosylation can occur (Walsh et al., Curr. Opin. Chem. Biol. 2001; 5:525-34).

In the present invention, a biosynthetic pathway containing the genes for a NRPS from *Streptomyces hygroscopicus* NS17 has been isolated and characterized (SEQ ID NO:1). The NRPS exists as two separate components that have been termed MppA (SEQ ID NO:2) and MppB (SEQ ID NO:4). These components both are involved in the synthesis of the core of AC98.

MppA (SEQ ID NO:2) is composed of three minimal modules, where each module is comprised of an adenylation, thiolation, and condensation domain. MppA (SEQ ID NO:2) conjugates a serine amino acid to a glycine amino acid to produce a peptide. This peptide is then conjugated (through the glycine) to a phenylalanine amino acid. Each amino acid is incorporated into the peptide chain by a unique module. In one embodiment, MppA (SEQ ID NO:2) is about 295 kDa. In another embodiment, MppA (SEQ ID NO:2) is about 2747 amino acids in length. In one embodiment, MppA has an amino acid sequence as depicted in SEQ ID NO:2. In another embodiment, the MppA protein (SEQ ID NO:2) is encoded by a nucleic acid sequence as depicted in SEQ ID NO:3. After addition of the phenylalanine, the peptide chain is then transferred to the MppB (SEQ ID NO:4) component.

The specificity of each AC98 adenylation domain in the NRPS of the present invention was predicted based on the method described in Challis et al., Chem. Biol. 2000; 7:211-24. Amino acid residues 235, 236, 239, 278, 299 & 301 lining the binding pocket of each adenylation domain were found to define domain specificity (the adenylation domains of MppA (SEQ ID NO:2) and MppB (SEQ ID NO:4) modules are depicted in FIG. 4) and, in turn, the order of amino acid incorporation into the growing AC98 peptide chain (See FIG. 3).

MppB (SEQ ID NO:4) is composed of 2½ modules and two epimerization domains. In other words, MppB (SEQ ID NO:4) is comprised of 2 complete minimal modules (as described above for MppA (SEQ ID NO:2)) and an additional condensation and thiolation domain (which constitutes the ½ module). The peptide chain synthesized by MppA (SEQ ID NO:2) is transferred to MppB (SEQ ID NO:4) where a tyrosine amino acid is added to the chain. Prior to the condensation domain, an epimerization enzyme alters the chirality of the tyrosine residue from an L-amino acid to a D-amino acid. The peptide chain is then transferred to a module where a first cycloarginine moiety is added to the peptide. The module which incorporates the first cycloarginine moiety into the peptide is then reused to incorporate a second cycloarginine moiety. A second epimerization domain then alters the chirality of the second cycloarginine from an L-amino acid to a D-amino acid. The terminal module of MppB (SEQ ID NO:4) is unique in that there is only one adenylation domain used for the addition of two cycloarginine residues to the peptide core.

In one embodiment, MppB (SEQ ID NO:4) is about 394 kDa. In another embodiment, MppB (SEQ ID NO:4) is about 3668 amino acids in length. In one embodiment, mppB has an amino acid sequence as depicted in SEQ ID NO:4. In another embodiment, the MppB (SEQ ID NO:4) protein is encoded by a nucleic acid sequence as depicted in SEQ ID NO: 5. After epimerization, the peptide sequence is then modified by tailoring enzymes including, but not limited to, glycosylation enzymes, methylation enzymes and acylation enzymes.

Tailoring Enzymes

After production of the core of the peptide, the sequence may then be modified by additional enzymes which are herein termed "tailoring enzymes". These enzymes alter the amino acids in the compound without altering the number or the specific amino acids present within the compound. Such tailoring enzymes may include, but are not limited to, arginine cyclase, an O-mannosyltransferase, a phenylalanine C-methyltransferase, a first isovaleryl transferase, and a second isovaleryl transferase.

In the present invention, these tailoring enzymes have been determined to be ORFs present on the AC98 biosynthetic gene cluster and have been termed ORF1-ORF24 (with SEQ ID NOs as described in Table 1). Sequence comparison of these ORFs with homologs provide preliminary information about the function of the enzymes. Table 1 below provides a correlation between the ORF, its location within SEQ ID NO: 1, and its proposed function.

The present invention permits specific changes to be made to the ORFs that encode the tailoring enzymes, either by site directed mutagenesis or replacement, to genetically modify the peptide core. The modifications may be made in a rational manner to improve the biological activity of the antibiotic produced by the bacterial strain or to direct synthesis of compounds that are structurally related to AC98. The invention also allows for the ORFs encoding tailoring enzymes to be isolated and used for biotransformation experiments to produce enzymes to modify and possibly improve other useful compounds.

The determination of the entire biosynthetic pathway of AC98 also enables one of ordinary skill in the art to clone and express the pathway into a heterologous organism. Any organism may be used; preferably a bacterial strain is used. The choice of organism is dependent upon the needs of the skilled artisan. For example, a strain that is amenable to genetic manipulation may be used in order to facilitate modification and production of AC98.

The present invention advantageously permits specific changes to be made to individual modules of NRPS, either by site directed mutagenesis or replacement, to genetically modify the peptide core. Additionally, the NRPS modules can be used to modify other NRPSs that direct the synthesis of other useful peptides through module swapping. For example, the module in NRPS that incorporates tyrosine into the peptide core of the antibiotic may be modified so as to incorporate a serine in its place.

TABLE 1

ORF Correlation

| Orf | Position (bp) | No. Amino Acids | Sequence Homolog Accession No.* | Percent Identity | Proposed Function |
|---|---|---|---|---|---|
| orf1 (SEQ ID NO: 6) | 77-1048 | 323 (SEQ ID NO: 21) | BAB69251<br>Pfam PF00583 | 68% | Acetyltransferase |
| orf2 (SEQ ID NO: 7) | 1045-2460 | 471 (SEQ ID NO: 22) | BAB69250<br>Pfam PF01574 | 61% | ABC transporter |
| orf3 (SEQ ID NO 8) | 2495-3406 | 303 (SEQ ID NO: 23) | BAB69249<br>Pfam PF00528 | 70% | ABC transporter |
| orf4 (SEQ ID NO 9) | 3403-4293 | 296 (SEQ ID NO: 24) | BAB69248<br>Pfam PF00528 | 67% | ABC transporter |
| orf5 (SEQ ID NO: 10) | 4359-5635 | 425 (SEQ ID NO: 25) | G75191<br>Pfam PF00535 | 34% | Dolichol-phosphate mannosyltransferase |
| orf6 (SEQ ID NO: 11) | 5822-7234 | 470 (SEQ ID NO: 26) | AE007470 | 20% | Dolichol-phosphate mannose protein mannosyltransferase |
| orf7 (SEQ ID NO: 12) | 7293-8822 | 509 (SEQ ID NO: 27) | X91736 | 29% | Unknown |
| orf8 (SEQ ID NO: 13) | 9012-10025 | 337 (SEQ ID NO: 28) | X79146<br>Pfam PF00891 | 27% | methyltransferase |
| orf9 (SEQ ID NO: 14) | 29319-30638 | 439 (SEQ ID NO: 29) | Z13972 | 32% | D-aminoacyl hydrolase superfamily |
| orf10 (SEQ ID NO: 15) | 30658-32010 | 450 (SEQ ID NO: 30) | BAB69335 | 29% | efflux protein |
| orf11 (SEQ ID NO: 16) | 32181-33407 | 408 (SEQ ID NO: 31) | AF263245<br>Pfam PF01757 | 38% | isovaleryl transferase |
| orf12 (SEQ ID NO: 17) | 33422-34792 | 456 (SEQ ID NO: 32) | AF263245<br>Pfam PF01757 | 31% | isovaleryl transferase |
| orf13 (SEQ ID NO: 18) | 34905-35930 | 341 (SEQ ID NO: 33) | AF210249 | 45% | enduricydidine synthase |
| orf14 (SEQ ID NO: 34) | 36383-37264 | 293 (SEQ ID NO: 35) | AF110468 | 31% | Transaminase |
| orf15 (SEQ ID NO: 36) | 37264-38514 | 415 (SEQ ID NO: 37) | AE001954 | 30% | Transaminase |
| orf16A (SEQ ID NO: 38) | 38466-39374 | 302 (SEQ ID NO: 39) | ZP_00095168 | 38% | hypothetical protein |
| orf16B (SEQ ID NO: 54) | 39389-40375 | 329 (SEQ ID NO: 55) | NP_629045 | 34% | putative regulatory protein |
| orf17 (SEQ ID NO: 40) | 40440-40655 | 71 SEQ ID NO: 41) | AL035654 | 69% | cda-orfX homolog |
| orf18 (SEQ ID NO: 42) | 46384-47649 | 421 (SEQ ID NO: 43) | NP 823141.1 | 53% | putative secreted protein |
| orf19 (SEQ ID NO: 44) | 44182-45813 | 543 (SEQ ID NO: 45) | ZP 00058556.1 | 29% | hypothetical protein |
| orf20 (SEQ ID NO: 46) | 43248-44168 | 306 (SEQ ID NO: 47) | NP 422360.1 | 42% | ABC transporter |
| orf21 (SEQ ID NO: 48) | 42817-43245 | 142 (SEQ ID NO: 49) | NP 826991.1 | 38% | putative lipoprotein |
| orf22 (SEQ ID NO: 50) | 41586-42758 | 390 (SEQ ID NO: 51) | AAP03102.1 | 34% | two component sensor kinase |
| orf23 (SEQ ID NO: 52) | 40773-41441 | 222 (SEQ ID NO: 53) | AAP03103.1 | 58% | two component response regulator |
| orf24 (SEQ ID NO: 56) | 47770-48180 | 136 (SEQ ID NO: 57) | CAD18970.1 | 60% | putative lactone-dependent transcriptional regulator |
| mppA (SEQ ID NO: 3) | 10069-18309 | 2747 (SEQ ID NO: 2) | AL035640 | | NRPS |
| mppB (SEQ ID NO: 5) | 18309-29312 | 3668 (SEQ ID NO: 4) | AL035640 | | NRPS |

*SeqWeb ™, which uses Wisconsin [GCG] Package version 10

Methods of Modifying Bacterial Proteins

The role of the proteins encoded by mppA (SEQ ID NO:3), mppB (SEQ ID NO:5), or ORF1-ORF24 (as described in Table 1) may be evaluated using any method known in the art. For example, specific modifications to a protein sequence may be produced to alter the final product. Other non-limiting examples of studies that may be conducted with these proteins include (i) evaluation of the biological activity of a protein and (ii) manipulation of a synthetic pathway to alter the final product from bacteria. More detailed discussion of these proposed uses follows.

Genetic manipulations and expression of the proteins discussed herein may be conducted by any method known in the art. For example, the effect of point mutations may be evaluated. The mutations may be produced by any method known in the art. In one specific method the manipulations and protein expression may be conducted using a vector that comprises at least one Gram-negative and at least one Gram-positive origin of replication. The origins of replication allow for replication of the nucleic acid encoded by the vector, in either a Gram-negative or a Gram-positive cell line. In one embodiment, the vector comprises one Gram-negative and one Gram-positive origin of replication. Additionally, the vector comprises a multiple cloning site that allows for the insertion of a heterologous nucleic acid that may be replicated and transcribed by a host cell.

The most evolved mechanism of transfer of nucleic acids is conjugation. As used herein, the term "conjugation" refers to the direct transfer of nucleic acid from one prokaryotic cell to another via direct contact of cells. The origin of transfer is determined by a vector, so that both donor and recipient cells obtain copies of the vector. Transmissibility by conjugation is controlled by a set of genes in the tra region, which also has the ability to mobilize the transfer of chromosomes when the origin of transfer is integrated into them (Pansegrau et al., *J. Mol. Biol.,* 239:623-663, 1994; Fong and Stanisich, *J. Bact.,* 175:448-456, 1993).

Evaluation of the Biological Activity of a Protein

Evaluation of the mechanism of a protein and role the protein plays in the synthesis of a compound has traditionally been determined using sequence homology techniques. However, such techniques may not be accurate and better methods of evaluating novel proteins need to be developed. The vector described previously may be used to assess the biological activity of an unknown protein. The vector may be used to disrupt a protein, either by partial or complete removal of the gene encoding the protein, or by disruption of that gene. Evaluation of the products produced when the altered protein is present is useful in determining the function of the protein.

Manipulation of a Synthetic Pathway to Alter the Final Product

As discussed above, many compounds obtained from organisms have complex stereochemistries. These compounds are not amenable to production or manipulation by conventional synthetic methods. Therefore, new methods are needed to produce altered products.

Specific proteins within the biochemical pathway of the product may be modified to assess the activity of the compounds produced by these altered proteins and to determine which sections of the product are important for activity and function.

The present invention contemplates any method of altering any of the proteins of the present invention. More specifically, the invention contemplates any method that would insert amino acids, delete amino acids or replace amino acids in the proteins of the invention. Additionally, a whole domain in a module in MppA (SEQ ID NO:2) or MppB (SEQ ID NO:4) may be replaced. Therefore, for example, the acylation domain that incorporates tyrosine into the final product may be replaced with a domain that incorporates serine. The modifications may be performed at the nucleic acid level. These modifications are performed by standard techniques and are well known within the art.

Upon production of the nucleic acid encoding the modified protein, the protein can be expressed in a host cell. Then the host cell can be cultured under conditions that permit production of a product of the altered pathway.

Once the product is isolated, the activity of the product may be assessed using any method known in the art. The activity can be compared to the product of the non-modified biosynthetic pathway and to products produced by other modifications. Correlations may be drawn between specific alterations and activity. For example, it may be determined that an active residue at a specific position may increase activity. These types of correlations will allow one of ordinary skill to determine the most preferred product structure for specified activity.

The present invention also contemplates a method for using an intergeneric vector, described infra in the examples, to manipulate, modify, or isolate a protein involved in the synthesis of a specific product. For example, the vector of the present invention may be used to alter an enzyme which is involved in incorporation of an alanine residue into a peptide, so that a tyrosine residue is incorporated instead. The effect of this modification on peptide function may be then be evaluated for biological efficacy. In the above example, modifications to the enzyme may include, but are not limited to, removal of amino acids and/or sequences that specifically recognize alanine and/or incorporation of amino acids and/or sequences that specifically recognize tyrosine.

Therefore, in general terms, the vector of the present invention may be used to alter a gene sequence by insertion of nucleic acid sequences, deletion of nucleic acid sequences, or alteration of specific bases within a nucleic acid sequence to alter the sequence of a protein of interest; thereby producing a modified protein of interest. Preferably, the protein of interest is involved in the synthesis of a compound of interest. The method of modifying a protein comprises (i) transfecting a first bacterial cell with the vector of the present invention, (ii) culturing the first bacterial cell under conditions that allow for replication of the vector, (iii) conjugating the first bacterial cell with a second bacterial cell under conditions that allow for the direct transfer of the vector from the first bacterial cell to the second bacterial cell, and (iv) isolating the second bacterial cell transformed with the vector. In a preferred embodiment, the first cell is a Gram-negative bacterial cell and the second cell is a Gram-positive cell.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

"Amplification" of DNA as used herein denotes the use of polymerase chain reaction (PCR) to increase the concentration of a particular DNA sequence within a mixture of DNA sequences. For a description of PCR see Saiki et al., Science 1988, 239:487.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "promoter" or "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

The terms "vector", "cloning vector" and "expression vector" refer to the vehicle by which DNA can be introduced into a host cell, resulting in expression of the introduced sequence. In one embodiment, vectors comprise a promoter and one or more control elements (e.g., enhancer elements) that are heterologous to the introduced DNA but are recognized and used by the host cell. In another embodiment, the sequence that is introduced into the vector retains its natural promoter that may be recognized and expressed by the host cell (Bormann et al., J. Bacteriol 1996; 178:1216-1218).

An "intergeneric vector" is a vector that permits intergeneric conjugation, i.e., utilizes a system of passing DNA from *E. coli* to actinomycetes directly (Keiser, T. et al., Practical *Streptomyces* Genetics (2000) John Innes Foundation, John Innes Centre (England)). Intergeneric conjugation has fewer manipulations than transformation.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct". A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); F. M. Ausubel et al. (eds.), Current Protocols in Molecular Biology, John Wiley & Sons, Inc. (1994).

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g,. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). For the present invention, host cells include but are not limited to *Streptomyces* species and *E. Coli.*

The term "expression system" means a host cell and compatible vector under suitable conditions, e.g. for the expression of a protein coded for by foreign DNA carried by the vector and introduced to the host cell. In a specific embodiment, the host cell of the present invention is a Gram-negative or Gram-positive bacteria. These bacteria include, but are not limited to, *E. coli* and *Streptomyces* species. An example of a *Streptomyces* species that may be used includes, but is not limited to, *Streptomyces hygroscopicus.*

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. In this context, the heterologous DNA sequence refers to an DNA sequence that is not naturally located within the NRPS sequence. Alternatively, the heterologous DNA sequence may be naturally located within the NRPS sequence, but is found at a location in the NRPS sequence where it does not naturally occur. A heterologous expression regulatory element is such an element is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

The terms "mutant" and "mutation" mean any detectable change in genetic material, e.g. DNA, or any process, mechanism, or result of such a change. This includes gene mutations, in which the structure (e.g. DNA sequence) of a gene is altered, any gene or DNA arising from any mutation process, and any expression product (e.g. protein or enzyme) expressed by a modified gene or DNA sequence.

The term "variant" may also be used to indicate a modified or altered gene, DNA sequence, enzyme, cell, etc., i.e., any kind of mutant. Two specific types of variants are "sequence-conservative variants", a polynucleotide sequence where a change of one or more nucleotides in a given codon position results in no alteration in the amino acid encoded at that position, and "function-conservative variants", where a given amino acid residue in a protein or enzyme has been changed without altering the overall conformation and function of the polypeptide. Amino acids with similar properties are well known in the art. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Clustal Method, wherein similarity is based on the algorithms available in MEGALIGN. A "function-conservative variant" also includes a polypeptide or enzyme which has at least 60% amino acid identity as determined by BLAST or FASTA alignments, preferably at least 75%, more preferably at least 85%, and most preferably at least 90%, and which has the same or substantially similar properties or functions as the native or parent protein or enzyme to which it is compared.

As used herein, the terms "homologous" and "homology" refer to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Accordingly, the term "sequence similarity" refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a specific embodiment, two DNA sequences are "substantially homologous" or "substantially similar" when at least about 80%, and most preferably at least about 90% or 95% of the nucleotides match over the defined length of the DNA sequences, as determined by sequence comparison algorithms, such as BLAST, FASTA, DNA Strider, etc. An example of such a sequence is an allelic or species variant of the specific genes of the invention. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially similar" when greater than 80% of the amino acids are identical, or greater than about 90% are similar. Preferably, the amino acids are functionally identical. Preferably, the similar or homologous sequences are identified by alignment using, for example, the GCG (Genetics Computer Group, Program Manual for the GCG Package, Version 10, Madison, Wis.) pileup program, or any of the programs described above (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligoncucleotide molecules used. Exemplary temperatures may be 37° C. (for 14-base oligonucleotides), 48° C. (for 17-base oligoncucleotides), 55° C. (for 20-base oligonucleotides) and 60° C. (for 23-base oligonucleotides). Exemplary suitable hybridization conditions for oligonucleotides include washing in 6×SSC/0.05% sodium pyrophosphate, or other conditions that afford equivalent levels of hybridization.

EXAMPLES

The present invention will be better understood by reference to the following Examples, which are provided as exemplary of the invention, and not by way of limitation.

Example 1

Identification and Cloning of the Non-Ribosomal Peptide Synthetase Complex Responsible for Antibiotic Production (AC98) in *S. hygroscopicus*

Methods

Isolation of genomic DNA from *S. hygroscopicus. Streptomyces hygroscopicus* strain designated NS17 was cultured by inoculation of 25 ml of sterile tryptone soya broth (TSB) (Oxoid, Ogdensberg, N.Y.) prepared by combining 30 g of TSB in 1 L of distilled water) with 100 μl of a frozen glycerol stock of NS17. Cultures were grown at 28° C. while shaking at 200 rpm for 2 days. Cells were harvested by centrifugation at 3000×g for 10 min, followed by resuspension of the pelleted cells in 2 ml lysis buffer (2% Triton X-200, 1% SDS, 100 mM NaCl, 10 mM Tris, pH 8.0, 1 mm EDTA) and vortexing. After vortexing, 2 ml of phenol/chloroform/isoamyl alcohol (25/24/1 v/v) was added and the suspension was vortexed again for about 1 min to ensure lysis. The sample was then centrifuged for 5 min at 3000×g and the aqueous phase was added to 2 volumes of 95% ethanol to precipitate the genomic DNA. The precipitate was collected by centrifugation or by spooling, washed once with 70% ethanol, and air dried. DNA was resuspended in 100 μl of TE buffer (10 mM Tris, 1 mM EDTA, pH 8.0).

Isolation of a peptide synthetase probe and Southern hybridization. Degenerate PCR primers were designed based on the highly conserved core motifs of peptide synthetase adenylation domains A3 and A8 (Marahiel et al., 1997).

| | |
|---|---|
| forward primer | 5'-ACG/CTCG/CGGCT/ACGCACCGGCCIGCCG/CAAG-3' (SEQ ID NO:19) |
| reverse primer | 5'AGCTCG/CAT/CG/CCGG/CTAGCCG/CCGG/CAT/CCTTG/CACCTG-3' (SEQ ID NO:20) |

G/C or T/A or T/C denote either base at that position

NS17 genomic DNA was used as a template to synthesize a fragment of about 800 bp in length by PCR using a Perkin Elmer DNA Thermal Cycler 480 (Boston, Mass.-30 cycles: 95° C.-1 min, 55° C.-1 min, 72° C.-1 min). This fragment was subjected to end sequencing using an Applied Biosystems, Inc. ABI3700 sequencer (Foster City, Calif.) to determine that it corresponded to a portion of peptide synthetase adenylation domain, and used to as a probe in Southern hybridization of NS17 genomic DNA under standard conditions (Sambrook et al., 1989).

Identification of a functional NS17 peptide synthetase module. A 3 kb fragment containing a putative peptide synthetase module identified from the Southern hybridization was sequenced as described above for confirmation, and used in a biosynthetic assay to determine whether the putative peptide synthetase module was part of the AC98 biosynthetic cluster. Specifically, the method described under Example 2, below, was used to insertionally inactivate the putative peptide synthetase, which was then used to replace the endogenous peptide synthetase in *S. hygroscopicus* NS17, by homologous recombination. If the 3 kb fragment was part of the AC98 biosynthetic gene cluster, replacement of the endogenous gene with the insertionally inactivated 3 kb fragment would inhibit antibiotic production if the peptide synthetase encoded by 3 kb fragment is part of the AC98 biosynthetic cluster.

To evaluate antibiotic production, samples were removed from 50 ml cultures NS17 carrying the disrupted gene. Cultures were grown at 28° C. in PharmaMedia (Chrysalis PharmaMedia, NJ:10 g/L PharmaMedia, 5 g/L $CaCO_3$, 40 g/L glucose) and were analyzed by HPLC. 20 μl aliquots were loaded onto a Waters 4 mm×50 mm YMC ods-a-column (Milford, Mass.) and eluted with a gradient of 10% acetonitrile/90% TFA (20%) in water to 34% acetonitrile/66% TFA in water over 15 minutes. AC98 related compounds were detected by UV-DAD at 226 nm. Chromatograms were compared to chromatograms of samples taken from a similarly treated culture of the parental strain.

Preparation and Screening of an NS17 Cosmid Library. Genomic DNA isolated from NS17 as described above was used for the construction of a cosmid library. Optimal conditions for partial digestion of the DNA by restriction enzymes, to produce DNA fragments of about 35 kb, was determined using published techniques (Sambrook et al., 1989). The digested DNA fragments were dephosphorylated with calf intestinal alkaline phosphatase (New England Biolabs, Beverly, Mass.) according to the protocol provided by the manufacturer, and ligated into the commercial vector, pWE 15 (Stratagene, La Jolla, Calif.) according to the manufacturer's instructions. Packaging of the ligated mixture was accomplished using Gigapack III XL packaging extract (Stratagene), and the resulting library was titered and amplified according to the manufacturer's instructions.

The cosmid library was screened using the 3 kb peptide synthetase fragment, identified as described above, according to standard colony hybridization protocols (Sambrook et al., 1989). One cosmid, designated pNWA117, was selected for further study.

Cosmid analysis and identification of ORFs 1-13 (SEQ ID NOs:6-18). Cosmid pNWA117 was digested with EcoRI, subjected to agarose gel electrophoresis and used in a Southern hybridization with the 3 kb fragment, identified as described above, as a probe. Following confirmation that the pNWA117 contained the 3 kb fragment, the cosmid was sequenced (MWG Biotech, Highpoint, N.C.).

Nucleotide BLAST analysis (SeqWeb™, which uses Wisconsin [GCG]Package version 10) was performed to identify individual ORFs and their putative function, according to their homology with known sequences. Results are presented in Table 1.

Cosmid analysis and identification of ORFs 14-24. Genomic DNA downstream of pNWA117 was isolated from a cosmid library by using a fragment of DNA from ORF12 of the analyzed sequence to select cosmids containing stretches of genomic DNA encoding that region of AC98 biosynthetic pathway. This process is commonly referred to as chromosomal walking. One such cosmid, pNWA105, was selected after restriction analysis indicated that it contained approximately 12 Kb of DNA downstream of ORF13. Nucleotide BLAST analysis of sequence data obtained was performed to identify twelve complete ORFs (ORF14 (SEQ ID NO:34), ORF15 (SEQ ID NO:36), ORF16A (SEQ ID NO:38) and ORF16B (SEQ ID NO:54), ORF17 (SEQ ID NO:40), ORF18 (SEQ ID NO:42), ORF19 (SEQ ID NO:44), ORF20 (SEQ ID NO:46), ORF21 (SEQ ID NO:48), ORF22 (SEQ ID NO:50), ORF23 (SEQ ID NO:52), and ORF24 (SEQ ID NO:56)), and their putative function in AC98 biosynthesis, according to their homology with known sequences. Results are presented in Table 1.

Results

Isolation of an NRPS in NC17 responsible for the production of AC98. Results from the experiments described above demonstrate that cosmid pNWA117 contains the genes encoding a NRPS required for the synthesis of the peptide core of the novel antibiotic complex AC98, which is produced by the terrestrial actinomycete *Streptomyces hygroscopicus*. pNWA117 also contains additional ORFs proposed to be involved in the synthesis of the AC98 complex. PNWA105 contains at least 4 additional ORFs that are proposed to be involved in AC98 biosynthesis. The NRPS complex exists as two separate components, MppA (SEQ ID NO:2) and MppB (SEQ ID NO:4). MppA (SEQ ID NO:2) is encoded within bp 10069 and 18309 of the sequence listed in SEQ ID. NO: 1, and is comprised of about 2747 amino acids (SEQ ID NO: 2). MppB (SEQ ID NO:4) is encoded within bp 18309 and 29312 of the sequence listed in SEQ ID NO: 1, and is comprised of about 3668 amino acids (SEQ ID NO: 3). Additional description and characterization of MppA (SEQ ID NO:2) and MppB (SEQ ID NO:4) is described infra, under the heading DETAILED DESCRIPTION.

Table 1 lists the 24 ORFs and corresponding SEQ ID NO's that were identified and determined to be tailoring enzymes involved in the production of the protein core of AC98 (column 1). Column 2 lists the bp position of each ORF according to the sequence contained within cosmid pNWA117 (SEQ ID NO: 1), along with the number of the amino acids encoded by each ORF (column 3). Column 4 identifies the public sequence with which each ORF is most homologous, according to BLAST analysis, and column 5 lists the proposed function of each polypeptide encoded by the individual ORFs based on the sequence homology.

Example 2

Preparation of an Intergeneric Vector

Materials

DNA restriction and modification enzymes and T4 DNA ligase were obtained from New England Biolabs. Plasmid DNA was isolated using commercial kits (Qiagen) and DNA fragments were purified using commercial kits (Tetra Link International). Competent *E. coli* cells were obtained from Stratagene. All were used according to manufacturer's specifications and with buffers and reagents supplied by the manufacturer. *Streptomyces* chromosomal DNA was prepared according to published protocols (Keisser et al. Practical *Streptomyces* Genetics, John Innes Centre, Norwich, England, 2000). Antibiotics were purchased from Sigma.

Methods pNWA200 vector preparation. A purified PstI fragment containing oriT from the R plasmid, RP4, was ligated to pFD666 (Denis & Brzezinski, *Gene,* 111:115, 1992), which was then linearized by digestion with Pst1 and dephosphorylated with calf intestinal phosphatase. This ligation mixture was transformed into competent XL-10 *E. coli* cells (Stratagene) following manufacturer's directions. The transformed cells were then plated onto nutrient agar plates containing 50 μg/ml kanamycin and incubated at 37° C. for 1 day. The incubation resulted in about 150 colonies. The colonies were replica plated onto a second kanamycin containing agar plate covered by a positively charged nylon filter, and after 6 hours incubation, the nylon filter containing the embedded colonies was treated with 0.5M NaOH (in 1M NaCl) to lyse the bacteria and denature their DNA according to standard Southern blotting procedures (Southern et al., *J Mol Biol.,* 98:503, 1975). The nylon filter was probed with a radioactively labeled 0.76 kb PstI fragment and one colony was selected on the basis of its hybridizing signal. The recombinant plasmid was then extracted from a fresh culture of the original hybridizing colony. Digestion of the plasmid with PstI produced two DNA fragments which electrophoresed to positions of 5.25 kb and 0.76 kb, corresponding to linear pFD666 (5.25 kb) and the 0.76 kb oriT containing Pst1 fragment. This recombinant vector replicated stably in *E coli* strains and did not show genetic rearrangement upon repeated subculturing and further isolation.

Example 3

Methods for the Modification of the NRPS AC98 Peptide Core

Based on the sequence data of MppA (SEQ ID NO:2) and MppB (SEQ ID NO:4) described above, and available data defining the critical binding pocket features, i.e., amino acid residues in the adenylation domain that determine the specificity of the amino acid that is accepted by the domain, those skilled in the art will be able to modify any of the adenylation domains of the NRPS and change the primary amino acid sequence in the peptide core of AC98, thus, modifying the properties of the molecule. This Example provides two methods for modifying the peptide core.

Preparation of an engineered bacterial strain that produces AC98. Preparation of an AC98-producing host strain for use for the production of modified AC98 described by the methods below, is done according to the following steps:

1. Clone a fragment of the adenylation domain from and NRPS of choice (e.g., using *E. coli*).
2. Insert an antibiotic resistance determinant, such as apramycin, within the cloned fragment from step 1, above. This insertion inactivates adenylation domain after it is inserted into a host genome.
3. Clone the construct in an intergeneric conjugation vector, such as pNWA200, which contains a second antibiotic resistance determinant, such as kanamycin.
4. Introduce the vector containing the cloned construct into an AC98-producing strain.
5. Select for a strain that has the construct integrated into the homologous region of the host's genomic DNA by screening for conjugates that are apramycin-resistant and kanamycin-sensitive.
6. Confirm integration of the apramycin resistance determinant at the desired location by southern hybridization and fermentation.

Once the proper host strain is selected, the insertionally inactivated module in the host genome can be replaced by either the same module that has been modified by site-directed mutagenesis, or by a module that has an adenylation domain that specifies acceptance of a different amino acid.

Method 1

Modification of the adenylation domain for the production of modified AC98. The cloned module of choice, e.g., the adenylation domain, is modified by introducing nucleotide changes that will alter the codons that specify the incorporation of the amino acids critical to the biding pocket. The nucleotide changes can be introduced using any method known in the art, such as site-directed mutagenesis. For example, changing the triplet codon for Ser239 in the tyrosine binding pocket of MppB (SEQ ID NO:4) from TCC to TGG, and changing the triplet codon for Valine299 from GTC to ATC, would change the amino acids at those sites to tryptophan and isoleucine, respectively. According to published data, one would expect that these changes would alter the specificity of the module from tyrosine to phenylalanine (Stachelhaus et al., Chemistry and Biol. 1999; 6:493-505).

The mutated module is then introduced, by conjugation, into a host strain that has been modified, as outlined above, to be resistant to an antibiotic, such as apramycin. Selection for the presence of a recombinant strain is two-fold. First, exconjugates are selected that are able to grown in the presence of kanamycin and apramycin. These strains represent those that have taken up the vector construct. Second, clones are selected that have lost resistance to both kanamycin and apramycin. This indicates that the susceptible clones have lost the apramycin resistance due to homologous recombination between the insertionally inactivated host tyrosine domain and the site-directed mutant version of the tyrosine domain. This loss of resistance further indicates that the vector is no longer in the host strain, and the mutated version of the tyrosine domain (i.e., the one specific for phenylalanine) replaced the insertionally inactivated tyrosine domain of the host (engineered as described above). Southern hybridization is then performed to confirm the insertion of the correct construct. Fermentation of the strain will result in the production of modified AC98 products where the cyclic peptide core contains phenylalanine in place of tyrosine.

Method 2

Module replacement or swapping for the production of modified AC98. For this method, two regions of approximately 1 kb flanking the module selected for replacement are cloned by PCR (the "arms"). The two arms are engineered so that the ends closest to the module (i.e., the 3' end on one arm and the 5' arm on the other) have appropriate restriction sites for subsequent insertion of the module in the correct orientation between the flanking arms. Next, the module of choice for insertion from another peptide synthetase (e.g., the threonine module from the CDA NRPS of *S. coelicolor*) is amplified by PCR. This PCR product is also engineered to contain the appropriate restriction sites compatible with those present in the cloned arms, in order for insertion between the two arms. After ligation of the arms and the module, the construct is transferred to the intergeneric conjugation vector, and introduced into a antibiotic-resistant host strain (e.g., the apramycin-resistant strain as described above). Selection of the conjugates is then performed as described above for the mutated module method. Those strains expressing the threonine module from the CDA NRPS instead of the tyrosine module of the AC98 NRPS are identified as being the result of homologous recombination between the arms of the vector and the homologous regions on the host NRPS that flank the insertionally inactivated tyrosine module. Production of the modified AC98, where the cyclic peptide core contains threonine, is achieved by fermentation.

Appropriate steps should be taken to ensure maintenance of the integrity of the ORFs during the processes described above. For example, sequencing of all PCR products is preferred to confirm that no inadvertent mutations are introduced into the sequences that will be used for cloning.

In addition or as an alternative to the peptide synthetase module of the NRPS, tailoring enzymes, such as those indicated in Table 1, may also be modified according to these methods in order to produce antibiotic molecules having a modified peptide core. As one example, inactivation of a methyltransferase enzyme will result in an antibiotic lacking specific methyl groups, which then may be evaluated for improved antibiotic activity.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that values are approximate, and are provided for description.

Patents, patent applications, publications, procedures, and the like are cited throughout this application, the disclosures of which are incorporated herein by reference in their entireties.

What is claimed:

1. An isolated nucleic acid having a nucleotide sequence selected from the group consisting of:

(a) a nucleotide sequence that encodes a polypeptide having the amino acid sequence of SEQ ID NO: 2;

(b) a nucleic acid sequence that hybridizes to a nucleotide sequence having the nucleotide sequence of SEQ ID NO:3, said hybridization being performed under the following stringent conditions: 68° C. in 0.2×SSC; or 42° C. in 50% formamide; wherein the nucleotide sequence encodes an MppA protein capable of forming a non-ribosomal peptide synthase (NRPS) complex with the MppB protein of SEQ ID NO:4; and (c) an isolated nucleic acid fragment having a nucleotide sequence complementary to the full length of nucleotide sequence of (a) or (b).

2. An isolated nucleic acid of claim 1, wherein the nucleic acid has the nucleotide sequence of SEQ ID NO:3.

3. An isolated nucleic acid according to claim 1, wherein the nucleic acid has a nucleotide sequence that is complementary to the sequence of SEQ ID NO: 3.

4. An isolated nucleic acid having the nucleotide sequence of SEQ ID NO:3, or the full-length complement thereof.

5. A chimeric nucleic acid construct comprising a nucleic acid of any one of claims 1, 2, 3, or 4, wherein said nucleic acid is operatively associated with an expression control sequence.

6. An expression vector comprising a nucleic acid sequence having a nucleotide sequence encoding a polypeptide having the amino acid sequence as set forth in SEQ ID NO:2, wherein the nucleic acid sequence is operatively associated with an expression control sequence.

7. An expression vector comprising the nucleic acid of any one of claims 1, 2, 3, or 4, wherein the nucleic acid is operatively associated with an expression control sequence.

8. An isolated host cell genetically modified to express the nucleic acid of any one of claims 1, 2, 3, or 4.

9. An isolated host cell genetically modified to express the nucleic acid of claim 1.

10. An isolated host cell comprising the expression vector of claim 7.

* * * * *

SEQUENCE LISTING

```
<160> NUMBER OF SEQ ID NOS: 57

<210> SEQ ID NO 1
<211> LENGTH: 48200
<212> TYPE: DNA
<213> ORGANISM: Streptomyces hygroscopicus

<400> SEQUENCE: 1

agatcgcgtg tacgccgtcg ccgggatcat gcgtgcgccg tcgccaaggt gccggatttg      60

cggtaagtag tgggcgatgt ccgccacgcc gcgcccgcga cccgttctac ggccgttccg     120

ccccggagac ggccgctcgc tgctggcggc ctggtgccgc agcgccccgg acgatccgat     180

caccgccgcc cgcttccgga cgctgatcct gctcgacccc aatttcgacc cagaggggtt     240

acgggtggcc gatctcgacg ggcaggtggt gggcgccgtc tacgccgtgc gccgccgtac     300

cccgctggcc ggcaccgacc tggagccgga cgtcggctgg atcctgttct tcttcgtcga     360

tccgccgcac cgccgtacgg gcctcggccg ccggctgctc accgatgccc tcgactggct     420

gcgcggacac ggccgcaccc gggtcgactt cgccccgtac gcccccccact acgtgctccc     480

cggcctggac cgggccgcgt acccggaggc cgcccggctg ctggcgagcc tcggcttccg     540

tccccgctac gaggccgcgg cgatggaccg cggcctggtc ggctaccgca tgccggacga     600

ggtacggcgg cacgaggcgg ccctgacggc gcgcggccac cgattcggca ccccgtccga     660

cgacgatctg gtggacctgc tcgggctggc cgaggagttc acccccgact gggcgcgggc     720

gatccggcag tgcctgaccg gcggcgcccc tctggaccgc atcgtcagcg cccgcgcacc     780

cgacgggcgg atggcgggct gggccatgca cggcgcgtac gacggtacgg ccgagcggtt     840

cggccccttc ggcgtacgga aggagctgcg cggcgccggt ctgggcaagg tgctgctgca     900

tctgacgctg gagcggatgc gggcgctcgg cgtgcacggg gcgtggttcc tgtggacggg     960

cgagcagagc ccggcggggc atctctaccg cgcgagcgga ttcaccacga cccggaggtt    1020

cacggtgctg cggtgggagg cgggatgagg cgccgtacat tcacggccgg ggccgcggcg    1080

ggggccgccc tgttggccgg ggccggatgc gacgcgcccg gtggcgccgg gcacggagac    1140

ggagagcacg gagacggaga cggcggtgac ggccggggca gcggcggccg tcgcggcgcc    1200

cccgtcaccc tgaccgtcct cacgcactac gcgagcgaac cgctcgcctc ggcgctgcaa    1260

accgtcgtcg acgcctggaa cgcgacgcac cggcgcatca cggtgcgcac ggccgcggtc    1320

aagttccccg atctgctgac gacttacatg gtgcggcagg ccgcgggcca gggcgccgac    1380
```

-continued

```
atcatccatc cgtactgcct gtggaccggc cagctggtgc gggccggagt actgcgcccg   1440

gtgccgccca cggccacgcg gcagatccgc cgggacttca ccccggcggc cgtggcggcg   1500

tcgtccgtgc acggcacgct ctacggctac cccacggagg tgcagaccta cgcgctctac   1560

tacaacaagc ggctgctgcg gcaggccggt atcgacggac cgccgggtac ctggcaggag   1620

ctggaggacg cggcgtaccg caccgcccgc cgcgaccgcc acggcaacat gctggtgcag   1680

ggcttcgggc tgtcacgggc cgacgatgcg agcgtcgtgg ggcagacgct ggccctgctg   1740

gccgcgcgcg gcggcacatt cctcacctcc gacggacggc ggaccgccat cggctcggcg   1800

gccgggcggg atgtgctcga cctggagcgc cggctcatcg accgcggcgc cgccgactcc   1860

ggtatctcgc tcctgagggc ctttccgtcc ggccaggtgg cgatggcgat caacgccggc   1920

tggtggacgg cgagtctgcg cggcgcgatg ggggcggact accgcgaggt cggggtggcg   1980

ccggtgccgg ggcccgcacc ggacgaccgc ggcacgctcg ccacgggctt cctgctcggc   2040

gtgaacgcga agagcagata tccgggggag gcctgggagt tcctgcactg gctcaacggt   2100

gtgcgggcgc cggccgcccg gccggggcgc agcgcgggag gaggcgtccc ggtgtccagg   2160

atgagcgcgc tccaggtgtc ggtcggttcg atgaccgggc gggcggacga tatgcgggcg   2220

ctgctgggag gcgacggcga gagggacgcc gacggccgtg gtggcggcga ccggaacctc   2280

ggccccttcc tggacgcgct gcgctacgcc gtcccggaac cgaacggtcc gcgcgcgcag   2340

caggccaaat cgctgctgcg caagaacatc gaggacgtct ggacgggccg ggcctcggtc   2400

gatgccgcgc tgcgcaccgc cggccggcag atcgaccagg aactgtcccg gccctactga   2460

gccactcccc catgtcgtcg agaggtggtg ccgaatggct tcagccggcg gtggtcccgt   2520

cagggcggcc cggcggcggc agaccgccgt cgcctatctg ttcctgaccc cggccctgct   2580

gttcttcgcg gtcttcctcg ccctgccgct gctgttcgcc gtgctgctcg cgcagtcgcg   2640

ctgggccggc ttcgacctcg ccgatatcga gccggtcggg atggccaact tcaccgacct   2700

cttcgcccgc ggctcgacct tcctgacgcc cgtcctcacc aatacgctgc tgtacgccgt   2760

cggcaccgtc gcgatcgccc tcatcggcgc gctcaccctc gcgacctgca tcgacaacct   2820

tcgtttccag gggctttggc ggaccctcta tttcctcccg atcgtgacga ccgtggtcgc   2880

cgtcggcaac gtatggaagt acatgtacgc accgggcggg ctgatcaacg gagtgctcaa   2940

cggtctgggt ctgcattccg tggcctttct ccaggacccc ggcacggcgc tgccgtccgt   3000

cgtcgtggtg caggcatggg cctccatggg aaccgcgatc ctgattctca ccgcgggcct   3060

gaagtcgatc cccgaggcct attacgaggc cgccgagctg gacggtgccg gcgccggcac   3120

cgttttccgg cgcatcaccc tgccgctgct ccggccgtcc ctgctcttcg tctgcatcac   3180

ccaattcatc accggattac agtcgttcgc cctgatcaat gtcatgacgg acgacggcgg   3240

accgggcgat gcgacgaatg tcgcggccct ggagatgtat cagcaggcgt tcaggtacgg   3300

cgactgggga atcgccagtg ccgccgcctt tgtgctgttc ctggtcattg tcgcgatcac   3360

ggtggggcag ctctggctgt tccgccggaa aggcggggaa tcgtgagccg gtccgctcgt   3420

cggcgcccgg gccgtcgccg cccctggggc tcgtacgccg tggtcgtcgc cggggccgcc   3480

ctcaccctcg tcccgttcct cgacatgctg ctgacctcgt tcaaggggcc cggcgaatac   3540

gggaaactcc cctaccgatt cctcccccag gcgttcgacc tttccaacta ccgtgccgcg   3600

atggagcagc tggatctgcc cctgcttttc cgcaacagcg tcatcgccac cgccgtcatc   3660

accggatcca tcctggtgac ctccgcgctc gccggatacg cgctggccaa gctgcgcttc   3720

cccggccggg aggtgatctt ccgcctggtc ctgtccacga tgatgttccc gccgttcctc   3780
```

-continued

```
ttcttcatcc cgcactttct gatcctggtg cactggcccg gcgccggcgg caacgacctg   3840
ctgggccgcg gcggggcggg cctcaccgtg agccttgcgg cgctggtcat gccgttcctc   3900
gtatccggtt tcgggatctt tctgatgcgg caattcatgg tctccatccc ggacgaactg   3960
ctggaggcgg cccgtatcga cggcgccggc gaattcgccc tctggtggcg catcgtgctg   4020
ccccagacga aaccggtggc ggtcaccctc gcgctgctca ccttcgtcaa cgcctggaac   4080
gaatacatct gggcgctgct gatctccacc gccaatccgc ggctgatgac gctgccggtg   4140
ggcatccaga tgctgcagag ctatctcgac cccgaccgta tggtcccggt catgatggcc   4200
ggcctggtgc tgagcatcct gccggtcctg ctgctcttcc tgctgctcca gaagcactac   4260
ctgcgcgggg tgatgctcag cggcctcaag tgacgtgcgt cctgggccga tgtggtcccg   4320
cggtgcaccc gccgaggttg acttctccgt aaaacatgat gagttccggt ttctcctggg   4380
ctgttgtggc aactgtggtg agagtttctg accccctcagg aggaaccatg gcttccgact   4440
cgtcgtcccc gacgccgatg ccggccgtgt cgttgatcgt gccgacgttc aacgaggcag   4500
cgaacattga tgagttgctc gacggcgtgt gtgcggcgat cccggcgggt ctggaggtcg   4560
aggtgctgtt cgtcgacgac tcgacggatg acacaccgga agtcatcgag aaggcggccg   4620
cgcgctgtcc gatgccggtg tcggtgctgc accgggaggt tcccgaaggg gggctcggcg   4680
gagcggtggt ggccgggatc gcccgtacga gtgcgccgtg gatcatggtg atggacgccg   4740
atctgcagca tccgccggag ctgctgccgc agttgatcga ggctggtgag cgcgcggcgg   4800
ccgagttggt ggtggccagc agatacgcgg agggcgggag ccgtggcggg ctggccggcg   4860
ggtaccgggt ggccgtgtcg ggggcgtcga ccgcgctgac caagtcgctg ttcccccggc   4920
tgctgcgcgg ggtctccgac ccgatgagcg ggtgcttcgc catccggcgg gaggcggtcg   4980
accgcgccgt acaggagggc gagacccggc aggaaggggg gctgcggccg ctcggctaca   5040
agattctgct ggagctcgcg gtgcgctgcc ggccgcgcgg ggtggtggag gtgccgtacg   5100
agttcgggga gcggttcgcc ggcgagtcga agtcgacggt gcgcgagggg ctgcggttcc   5160
tgcggcatct ggcggagctg cggaccagcg acaagcgggc ccggatggtg gccttcgggc   5220
tgatcggggt gtcgggcttc gtaccgaatc tgctggcgct gtgggcgctg accggtgcca   5280
cgaccctgca ttacgcggtg gcggaggtgc tggccaatca gctcggggtg ctgtggaact   5340
tcgccctgct ggacttcctg gtctaccgga gcgggaaacc ggggcgcggg gccggccggc   5400
tgctggggtt cgcggcgctc agcaacgcgg atctgctggc gcggatcccg ttgatgatgc   5460
tgttcgtgga gcaggccggg atggggccgg tgccggcgac cgtgatcagt ctcgtggtgg   5520
tgttcgcgct gcggttcctg ctggtcgaca cgttgatcta ccggcgcaag gggcgcggctg   5580
ccaagcgcgc ggcggacgcg gcggtcaccg gcgggcaggg cgagcgcgct gcttagctga   5640
caaggcaaac tcgtggcggc ccgcccccggc cggacagcag actccgagcg atgatctcgc   5700
cggattccac ctggacggac agaggcggag aaacgtgctg acagctcccg ttggtgtgga   5760
aacggatccg cgttcggcgg tacggccggc ccggcggccg gcggccgtcg tcgcgggcgc   5820
cgtgaccgtc gtgctgctcg ccctgtccga caggtacggc tacaacgtcg acgagctgta   5880
tttccggctg ctcggcgaac acggctgggc ctggggctac accgaccagc cgccgctggt   5940
gccggcgctg gtgcacgcca ccgcccaggt cctcggcgac tcggtgtggg cgatccgggt   6000
gccggcggcg ctgtgcgcag ggccgtggt gctgctcggg gcgctgatca ccgccgaact   6060
cggcggcacc cgccgggcac agactctttc cgccctgggt ctgggcagct cgttcctggt   6120
```

-continued

```
gctcagcgtc ggccacatca tggtgaccac caccctggac atgctcgcct gggccgcggt   6180
gctgctcttc gtcctgcggg cgctgctgcg ctcggagggc aagtggtggc tgtgggcggg   6240
ggtggtgctg ggcctggcgc tgtacgccaa gtacatcgtg gcgctgctgc cggtggcgct   6300
gctggccggg ctcgcgctgg tcggtccgcg gaaggtgttc cgtgaccggt ggctgtacgc   6360
ggggatcgcg ttggcgctgg ccatcggctc gccgaacctg atctaccagg ccacccatga   6420
cttcccgcag ctgcagatgg ccgatgcgct gggtgccacc gacggcccga tgaaccgggt   6480
catcttcgtg ccgagcctgg tgatcctgct cggtccggtg ctgaccgtgg tgtgggtcgc   6540
ggggctggtg aagctgctgc gtgacccggc atggcggccg gtgcgggcgc tggcaccggc   6600
gttcgtggtc ggggtggcgc tgaccctcta cggcggtggc cggcccgact acgtcggcgg   6660
gttcctgatc gggctgttcg cggccggggc ggtggccgcc gaccggtgga tggggcggcg   6720
tacgtcccgg cgggtgctgc tgtgcgccgg actggccgcc agtgcggtgc tccaggtgct   6780
gatggcgctg ccggtgctgc cgcagagctc cccgttcgtg ccgctgaaca acatctccct   6840
ggagagcgtc ggctggccgc ggctcgccga gcaggtgcgc acggcgtacg aggcgctgcc   6900
gcggcagcag cgggagcggg ccgtggtgct cgccgacaac ctcggggaga tcggcgcgct   6960
ggaccgctac gggcacgggc tgcccgcggt gttcagcggc cacaacgaac tgcacaagtg   7020
gggcccgccg ccggagcgcg ccgatgtggt ggtcgcggtg ggcgtgcccc ggtcccggct   7080
ggccgcgggg ttcacctcgt gcaccgtcgt gggacgggtc gacaacggcg tcggcgtcga   7140
gaacgccgag cagggcagac cgatcacggt gtgccacggc cgcaaggctt cctgggcccg   7200
actgtggccc tcctaccact acttgagcgg ctgatgtgcc cctgcacccc gggccgtgtg   7260
cgaatcgaca actcagcggg aagtgaggcg tgatgacgac atccctcgac agggattcca   7320
gggcggccgc ggccgggccg ggggtgttcc gcccggcgcc gatggcgtgg cggccggtcg   7380
ccgtggtggt ggccgcgctg gccgtgctgt tgttcgcctt cgccggcgaa tacggctacc   7440
acgccgacga gttgtacttc cggctgctcg gggtgcacgg cttcgcctgg ggctatgtgg   7500
accagccgcc gctgctgcca ctggccgtac ggacctcgat ggagatcttc ggcgacagca   7560
tgtgggcgat ccgggtgccc gccgtgctgt gcgcggcggc cgtgaccgcg ctcggcgcga   7620
tgatcgccgc cgagctgggc ggttcccggc gggcccagac gctgaccgcg ttcggggtgg   7680
ccacctcgac gatggtgctc agcttcggcc actggatcct caccaccagc ttcgacaccg   7740
tggcgtgggc cgcggtgctg ctgttcgtga tgcgggtgct gctgcgcggc gagagcaagt   7800
ggtggctgtg ggccggggtg gtggtcggtg tcgcgctgta cgccaagtac atcgtgctgc   7860
tgctgccggt ggcgctgctg gtggggctgg cgctggtcgg tccgcggaag gtcttccgcg   7920
acgggaagct gtacgcgggc acggcgctgg cgctggtcat cggctcgccg aacctgatct   7980
accaggccac ccatgacttc ccgcagctgc agatggcgga ggggctggcg ggcaccgacg   8040
gcgaggcgaa ccgcgccatg ttcgccacga acctgatcct gctgttcggc cccgcgctgt   8100
tcgtgctgtg catgatcggg ctggtcaagc tgttccgggt gccggagtgg aagcccgtac   8160
ggacactggc cgtcggctat ctcgcggcca ccgcggcgtc gtacctcatc gagggcggcc   8220
ggccggacta caccggcgga ctgctgatcg cgctgctggc cgccgggtgt gtgacggccg   8280
accggtgggc gggcgcccgc aagctgcggc tctcggtgct cgcggtctcg ctgacgctca   8340
gcaccgcggt gcagatgctg ctgtcgctgc cggtgatccc caagagctcg ctgcgcgact   8400
tccagatcgc cagcatggcg ctggagacgg tgggctggcc ccgtctggtc cagcagaccg   8460
aggcggccta ccgcgcactg ccggccgcgg accgcgaccg cgcgatcgtg ctcaccgaga   8520
```

-continued

```
acttcggcga ggcgggcgcc ctggaccact acgggcacgg gctgccgaag gtgtacagcg   8580
gccacaacga gctgtaccac tggggcccgc cgccgcagcg cgccgaggtg gtggtcgcgg   8640
tgggcatcga ccggaaccgg ctgtccgccg acttcaccag ctgcaaggtc gtcgaccaca   8700
tcgacaaccg cctgggcatc gacaatccgg aacagggcgt gccgatcacg gtgtgccacg   8760
gccccaagaa gccctggtcc gcgctgtggc cgacctaccg gcactacaac gcctatctgt   8820
agcgcgcctc tcgtccccca ccccgcggcc cggtccgaag caccttcgga ccgggccgtc   8880
cgccgacctg cttcgctgca cggtaaaagt cgtggatcag ccgcggagtt cacccgagac   8940
tggaaatcgc tggactgtgt acgcccatcc aatcgacttc cggacgaccc ctttcggggt   9000
ggaggcgtga tatgagtacc gaggtttccg aggcgcaggc gcgacgcgcc gtggcagaca   9060
tcttcaactc gacgctggct tcttcggcca tcggcgccgc gtgggagctc ggagctcttg   9120
acgagctgcg ggagaacggc aagttggatg tctccgattt cgccgtacgc catgatctgc   9180
acgagccggc ggtggtcggc atgttcaccg cgctggcgag tgtgggaatc gtgcggcgcg   9240
agggcgccac cgtcgtcgtc ggcccgtact tcgacgaggc caatcaccac cgttcactgt   9300
tccactggct caatcagggc agcggcgagc tcttccgccg catgccgcag gtgctgccga   9360
acgagaaccg cacaggaaag ttctaccagc gggacgcggg ggcgatcagc tacgcgtgcc   9420
gcgagatcag cgagcgctat ttcgacccgg cgttctgggc cgcggtcgac ggtctgggtt   9480
acacccccac caccgtcgcc gacctggggt ccggcagcgg tgagcggctg atccagatcg   9540
cccggcggtt ccccggcgtc cgcggcctcg gcgtggacat cgccgacggc gcgatcgcca   9600
tggcggagaa ggaggtggcc gccaagggat tcggcgacca gatctccttc gtgcggggcg   9660
acgcgcgcac catcgaccag gtctcggcgc gcggggaatt cgccgaggtc gatctgctca   9720
cctgcttcat gatggggcac gacttctggc cccgcgagaa ctgtgtgcag acgctgcgaa   9780
agctgcgcgc ggcattcccg aatgtgcgcc ggttcctgct cggcgacgcc acccgcaccg   9840
tcggtatccc cgaccgcgaa ctccccgtat tcaccctggg attcgagttc gggcacgaca   9900
tgatgggcgt ttacctgccg accctcgatg aatgggacgg ggtattcgaa gagggtggct   9960
ggcgctgtgt gaagaagcac gccatcgact cgctgtcggt ctccgtggtc ttcgaactcg  10020
agtaaccgca cacgcgcata tcgatcacgt cggcagaggg ggttttccat gggtgagtgg  10080
cgcgatcgcc gcctggacga attgttcgcc gagcaggccg cgagaacacc ggagcgtacc  10140
gcggtggtct tcgagggccg ggcggtgagt tatcgggaac tcgacgcccg cgccgagcgg  10200
ctggccgctg tgctggccgg ccgcggcgcg ggacccgagc ggttcatcgc gctgctgctg  10260
ccccgctccg ccgaactgat cgtggccatc ctcgccgtac tgaagtccgg cgccggatac  10320
atcccgatcg acccggagta cccggccgac cgcatcgcct acatcctcgg cgacgcgcgc  10380
ccggtggcga cgatcaccac cgccgaggtg cgggacggtc tgccggaccc ggacaccggc  10440
tccgggaccg actggctgat cctggacgag tccgggtacg agcaggagcc ggccggggcg  10500
cgcccgcagc ccgccccggc cgccccgcgg tccgcggaga accccgccta cgtcatctac  10560
acctccggct cgaccggccg gcccaagggc gtggtgatcc cgcacagcaa tgtgggacgg  10620
ctgctgtcgt ccaccgccca ctggtacggc ttcgacgagc aggacgtctg gccgctgttc  10680
cactccttcg ccttcgatgt ctcggtctgg gagatctggg gcgcgctgct gcacggcggc  10740
aagctggtcg tcgtcccgca tgccgtcacc cgcgccccgg ccgacttcct gcggctgctg  10800
gtcgaggaac gggtcaccgt cctgaaccag acgccttcgg cgttctacca gctgatggcc  10860
```

-continued

```
gccgaccggg agaaccccgc gctcggcgcc caactcgccc tgcgttatgt ggtgttcgcg  10920
ggtgaggcgc tggacctggg caagctcgcc gactggtacg agcggcacga tgaccgggcg  10980
ccgacgctgg tcaacatgta cggcatcacc gagaccaccg tgcactcctc gttcctcgca  11040
ctggacaagg agggcgcggc cggcgccacg ggcagcgccg tcggcgtcgc cctccccgac  11100
ctgaccttcc atgtcctcga cgaggacctg cggcccgtcc cggtcggcgc ggagggcgag  11160
ctgtatgtgg ccgggcccgg gctggcacgg aactacgcgg gccggccggg gctgaccgcg  11220
gagcgcttcg tggcctgccc gttcggcccg cccggggccc gtatgtaccg ctcgggcgac  11280
ctggtgcggc cgctgccgga cggcggcctc gaatacctgc ggcgcagcga cgaccaggtc  11340
aagatccgcg gtttccggat cgaactgggt gagatctcgc acgcactggc ccaggacccc  11400
tcggtcgacc aggccacggt ggtggtccgc gacgaggcgt cgggcgagcg caggctggtg  11460
gcgtacgtcg ttccggccgg ctccgcccgt cccaccccgt cccggctgcg tgccgcgctg  11520
gccacccgcc tgcccggcta catggtcccc accgccttcc acgtcatgcc ggccttcccg  11580
ctgaccgcca acggcaagct ggaccgcagg gcgctgcccg cgcccacccg ccaggacagc  11640
gtcgacgccg actacgccgc ccccgagggc gccaccgagg aggcgctggc cgccatctgg  11700
cgcgaggtgc tcggcgtcga acagatcggt gccgacgacg acttcttcga gctcggcggt  11760
gactcgctgt ccgtggtgcg ggcgctgtcg cggatgcgga ccggcctggg gctgcgcctg  11820
acggccgcgg agttcttcgc cacccccacc gtccgggcac tggccgcgcg ccgcgagcgg  11880
ggcacgatcg gcgcgccgga gcagataccg gccgcgccgc gtaccggcgc gctgccgctg  11940
tccttcaccc agcagcggtt ctggctcttc cacgaactcg accccggcga ggtcgagtac  12000
aacgtccact ccgcgctgcg gctgcgcggc accctcgacc tccccgcgct gcgcaccgcg  12060
ctcggcgggc tgatcgcccg ccatgagccg ctgcggacga ccgtggtctc cgacgacggc  12120
cgccccaccg cggtcatcgc cccgcccgag ggcttcccgg tcccgctcac cgtcgaggat  12180
ctctccgcgc tgaccggcga cgaccaggag gccgcccagc ggcgactgct ggccgaggag  12240
gtcgcccggc ccttcgacct ggccgccggc ccggtgctgc gggtgctggt gatccgccgc  12300
ggcgagcgcg atcacgccct ggtgatcggg gtgcatcacc tcgccaccga cggctggtcg  12360
atggggctgc tcaccgacga gctgagcgcg cgctacgacg ccgcgcgccg cggggtgccc  12420
gccgcgctgg agccgctgcc ggtccactac agcgactacg ccgcctggca gcgcgccacc  12480
gtggacgacg gccggctggt gccccagatc gactactggc gcgaccggct ggcggatgtg  12540
gcaccgctgc aactgcccac cgaccggccc cggcccgcgc tgaagacctc ggccggtgcg  12600
gcgcaccgct tcaccctcga ccgccggctg gtcgccgccc tcaaggagct gagcgccgcc  12660
catggcgcca cgctcttcat gaccctgacc gccgcgttgc aggtgctgct cgcccgctac  12720
tccggacagc aggacatcgc gctgggcacc gccgtctccg gccgggacca cccgcaggtg  12780
gagcggctgg tcggcgcgtt catcaacacc gtggtgctcc gctccgacgt gcgcggcgag  12840
ctgcccttcc acgaattcct cggggaggta cgggagacgg tgctgggcgc cttcgcgcac  12900
caggaccttc cgttcgaccg gctcgtggac gcgctgggcg ccgagcgcga cccgagccgt  12960
accccgctgg tccaggcgat gctgctgctg cagaacgccc cggccggtgc ggaggagttc  13020
gccgggctgc gcaccgagac cgtcgcgctg ccgcgcccgg ccgcgatctt cgacctgacg  13080
gtggactgca cggagcgggc cggggcgctg gaggtgatgg tcgagtacaa caccgatctg  13140
ttcgacgcga cgaccatcga gcggctctcg ggccatctgc gggtgctgct ggacgccgta  13200
tgcgcggcac cgcggcgcca ggtgcgcgat ctgccgctgc tgccggcggc cgaacgcgac  13260
```

-continued acgctgctga ccggctggaa cgacaccgcc gccgcactgc cgacgacgct cggggtgcac 13320
cgccagttcg ccgagcgggc ccgcaccacc ccggacgcgc tcgccgtcac acactgcgga 13380
cagaccctca cctacgccca actcgacgcg cgcgccaacc agttggcgca ctacctgggc 13440
gctctcggcg tcggccgggg cacccccgtg gtgctgaacc tggcgcgcaa gccgcagctg 13500
atcgtggcga tgctcgcggt gctcaaggcc ggcggcgcgt acgtaccgac cgcgctggac 13560
accccggcgg cacggctcgg gcatctcctg gaggagaccg gcacccccgt gctgctgacc 13620
accgcgcggc aggccggagc gctgccccg accgaggcga gcgtcatcga cctcgacgcg 13680
gccgggccgg acatcgcccg gcatccggag cacgaccccc aggtggcgac ccggcccgag 13740
gacctcgcgt acatcgtcta cacctccggg tccaccggcc gccccaaggg cgtcgcggtg 13800
ccgcacagcg cgctgaccga ctactgcgcc tggcacaacg acgcgctgga cgtcggcccc 13860
gaggaccgcg ggtcgtccgt ggtcggcctg gccttcgacg tcgcggtcgg cgaggtgtgg 13920
ccgtatctgt gcgcgggcgc ccgcgtggac cagcccgacc aggagacgct ggacgatccg 13980
acggcgctgg tggagtggtt cgccgagaac ggcaccacgg tcgcctatct gccgaccccg 14040
cgcatcgaat ccctgctgga cgtagcggcg atcaccacca cccggctgcg caccgtcctg 14100
gtcatcggcg actcgctgcg ccgcaggccg cagcccggac tgccgttcac cctgctcaac 14160
gcctacgggc ccgcggaggc gacggtggcc gccacccagg cggtggtcga gcccctggga 14220
cccgacgcgc ccgccgggct gccgtccatc ggcgccccgc tgtacaacac cgccgcctat 14280
gtcctcgacg accggctgtg cccggtcccc gtcggggtgc ccggcgagct gtacctcgcc 14340
ggcgcgggtc tggcgcaggg ctatcagggc cgcccgacc tgaccgcgga gcgcttcgtc 14400
ggctgcccct tcgggccgcc cggaacccgg atgtaccgca cgggtgacat cgtgcgatgg 14460
ctaccggacg gcaccctgga cttcctcggc cggatcgaca accaggtcaa actgcgcggc 14520
taccgcatcg aactcggcga gatcgagagc gtgctggccc gccgcgagga gctctcgcag 14580
gtgttcgtca cggtccgcga gccgtccccc ggccgccggt ccctggtcgc ctacctcgtc 14640
gccgaccggg gcaccgcgcc cgacccggag gagctcgccg gatacatcgc ctccgtactc 14700
ccggagtaca tggttccgtc ctccttcgta ctgctcgacg cgctgccgct gaccgcgaac 14760
ggcaagatcg accggcgggc gctgcccgag ccggagccgg ccggcggcga gggcgccgcg 14820
tatgtcgcgc ccggcaacga ggtcgaggag accctggccg ccatctgggc cgaggtgctc 14880
ggcgtcgaac gggtcggcgt gcaggacaac ttcttcgccc tcggcggcga ctcgatcagc 14940
ggtctgcaga ccgccgtacg ggcccgccgg gccgggctgc gactggcctc caaggacctc 15000
ttccagcgcc agaccatcgc ggcgctgagc cccgtggtga cggtggagcg gaccacggcg 15060
gacgccgacc ccgcaccgtc cgaccggccg accgcgccgt tcgcgctcag cggtctggac 15120
cgggtcggtg tggagcggct gaccgcggac ggcggcccgg ccgaggacgc ctacccgctg 15180
accccgatgc agagcgggct gctcttccac accctgatgc acgccgaacg cggcatgtac 15240
atcgagcagt tccacttcgc cctgcacagc atccgcgagc cggagctgct ggccaccgcc 15300
tggcagcggg tcgtcgaccg cacccctgtg ctccgtacgt cactggcctg ggacggcctc 15360
gccgaaccgc tccaggtcgt gcgcaccggc gtccggatac cggtggcaca gctcgactgg 15420
acggcactgg acgaggccgg acagcggcag gccctggagc ggtatctgac cgaggaccgc 15480
acgcgcgggc tcgatctgca caccgcgcca ctcgcccgga tcgccgtcgc ccgcctgggc 15540
ggcgaccagg tccggctggt gtggacgttc caccatctgc tgctggacgg ctggagcgtc 15600

-continued gtacaggtgc tgtccgaggt gctcggcgag tacgccgcgc tcgccgacgg catcccgtac 15660
accccgcaac tgcggcacac ctacgccgag ttcgtcggcc agctggcggg gcaggaccac 15720
accgccgccg agaagtactg gcgtgccgcg ctcaccggcc gtgagtcgcc caccccgctg 15780
ccgtacgacc ggccgcgccc cgacgcccat caggccgccc ccgacgccga gctgaagctg 15840
cggctgccgg ccgcggtgac cggccgactg ggcaccgcgg cgaagcgggc cggggtgacg 15900
atgaacaccg tggtgcaggg cttgtgggcg ctgctgctgg cccgccacag cggtgagcgg 15960
gacgtactgt tcggcgccac ggtcgccggc cggcccgacg atctggcggg cgcggaatcg 16020
gtgatcggcc tgttcatcaa caccettccg gtgcgcgtcg acgtcgatcc ggacgccggt 16080
ctgctgagct ggctgcgccg ggtgcaggac gagcaggccg aggcgcgcgc ccatgagcag 16140
gtctcgctcg cccaggtgca gggctgggcg ccggagcggg cgcacggcgg actgttcgac 16200
agcgtgctgg ccttcgagaa cttcccggcc gacctcggtc ccgccgggaa ctacgggctg 16260
cggctcgacg ccatcgaggc cagcaacacc tccaactacc cgctcaacgc catcgttcag 16320
ctcaacgaag agctgaccgt gctgctgcgc tacgacaccg cgctgttcga cgcggacacc 16380
gtggcgcggc tggccggcca tctgcacacg ctgctggagg agaccgccga gaaccccgac 16440
cgccgggtcg gcgagctgcc cctgctcacc gccgccgagc ggcacaccat cgtgcacacc 16500
tggaccgaca ccgcctcgga ctactcggtc gaccgccggc tggacgcggt catcgccgaa 16560
caggccgcgg cccggccgac cgcgatcgcc gtcgtcgacg gtgaacggca gctgagttac 16620
ggcgagttgg accgccgcgc caaccagctg gcacaccatc tgcgcgccgc gggcgtgggc 16680
cgggacgccc tcgtcgggat cgccgtcgag cgcagcgcgg aggtcgtcgt ggccatcctc 16740
ggcacgctca aggcgggcgc cgcgtatgtg ccgctcgacc ccgaattccc cgcgcagcgg 16800
ctcgccacca tgctgtccga gtcccggccc gcggtcctgc tcacccagga acacctgctg 16860
gcggggctgc cgccgacgga cgcccgggtg gtgtgcgtgg accgggacct ggcggccatc 16920
gaggcgcacc ccaccgccgc gccggtctcc ggcggcgacg ccggcgacct ggcctatgtc 16980
acctacacct cgggctccac cggccgcccc aagggcgtca tggtcgagca ccgctcgctg 17040
ttcaacatca tcaccgaggc cggacggctc tacgacctgg gccccgacag ccggatgctg 17100
cagttctaca caatgagctt cgacggcggc gtctgggagg tcttcctgac gctgaccgcc 17160
ggcgccaccc tcgtcatcgc ggaccccgag gcccgccaga gcccggccca cctcgccgag 17220
cagctgcgcg cggagtcgat caccgcgctg acgctgccgc ccgcggtggc ctcggtgctg 17280
gacgcggcct cgctgcccgg catacgcagc ctggggctcg ccggggatgt gctcgcgccc 17340
gaactcgccc gggagtgggc gcgggggcgc cggctgttca acatctacgg gcccagcgag 17400
gcgaccctgt ccgtcgccct gcaccgcgtc gaccccgggg ccgccgggcg ccaggtgccg 17460
ctcggaccgc cggtgcccaa cacccgtttc catgtgctcg acgagcggct ggccgtggtc 17520
ccggtcgggg tgaccggcga gctctacatc ggcggtgcgg gcctggcccg cggctacctg 17580
ggccgccccg acctgaccgc gcagcgcttc gtcgccgacc cgttcggacc gccgggatcc 17640
cgtctctacc gcaccggtga cctgatccgc tggaccccgc aggggcggct ggagttcgcc 17700
gggcgggtgg acaaccaggt caagatccgc ggctaccgtg tcgagcccgc cgaggtggag 17760
agcgcactgc tgcggcagcc cggcgtcgcg gaggcggtgg tgatcgcccg ggacgacgac 17820
accggccaca agcggctggt cgcctatgtc gtaccggacg ggagcggaac cgccccggaa 17880
cgcgccgccc tgctgcgcgc cctgggcggc caactccccg gctacatggt gccgtcggcc 17940
ctcgtcaccc tgcccgagct accgctcgga ccgaccggca aggtcgatgt gcgggcgctg 18000

-continued

```
ccggcaccgg atccggccgc cggcggcacc gccgaccgca tcccgccccg caccccccacg  18060
gaagaggcac tggccctcat ctgggtggag ctgctcgggc tcgaacacgt cggcgtcgag  18120
gacaacttct tcgacctcgg cggcgactcc atcaccagcc tgcggttgat gtcgcggatg  18180
ggcggcgcgt tcggtgtgga cgtctcaccc cgcgacttct tcgacgcccc caccatcgcc  18240
gcccttgccg agcgcctaga ggaaaagatc ctggcgcagt tggaagaagc cgtcggaggc  18300
ggcgccctat gaccagctct gcagcggacc agcccgacaa cccgaacacc accaccccgg  18360
cgtcgcgtgc cgagcgcacc gccgcgctgc cggcccatgt gcaggagctg ctgcgcgccc  18420
ggctggccgg ccgggccgcc gcgacgggcg gcgcggacac catcccgcgc atcgggcacg  18480
acggccccgt cgcgctctcg cccgcccagg aacgcctctg gtacctgcat gagctcgaac  18540
cggagagcaa cgagtacaac accctgcgcg tcctgcggct gcgcggcgac ctcgaccccg  18600
gcgcgctgtc cgcggcgctg agcgagatcg tcgcccggca cggcgcgctc cgcaccacct  18660
tcggctcccg cgaggggcac gccgagcaga ccgtgcatcc gcccgtaccg acaccgctgc  18720
cgctcgtcga cctgtcggcg gcggacgacg gcgagcggga cgacgcgctg cggaccctgc  18780
tgcagtacga ggcccggcgc cccttcgacc tgcgccgcgg cccggtgctg cgggcgcagc  18840
tgatccggct ggcggccgac gaccatgtcc tcgcgctggc cctgcatcac atcgtcaccg  18900
acggctggtc gatgggcgtg ctcaccggcg agctcaccgc ccactacgcc gcgacgctgc  18960
gcggtgcgcc cgccgtactg cccgaacttc cggtgagcta cctcgatgtc gccgtctggc  19020
agcgtgacca gctgagctcc gcgcggctgc gcgaggggct cgaccactgg cgccgggagc  19080
tggccgggct ggtcccgctc gatctgccga cgacctggca gcggccgccg gtccgcacca  19140
gcgccggagc gctgcactcc ttcgagatcc ccccggcggt cgccgcacgc cttcgggagc  19200
tgggccggga acagggcgcc acgctgttca tggcgctggt cgccgcggtc cagctgctgc  19260
tgtcgcgctg gtcggggcag cgggacatcg cggtgggcac cgccgcggcc gggcgcggcc  19320
ggaccgagac cgagaatctg atcggcttct tcgtcaacaa tctggtcctg cgctcccgga  19380
tcgatgagac gcggtcgttc accgagctgc tgcgggcggt acgcgcgacg gtcctggacg  19440
ccttcgccca cgaggatgtg ccgttccagc gggtcgtcga ggcgctgcat ccggagcgcg  19500
acctcagccg gccgccgctg gccgaggtcg cggtgaatct gcacaacacc ccgcggaccg  19560
acacggagct gcccgggctg cggatcgagg agatgccgcc gccggtgttc gcctccagca  19620
tggacctctc gttcgacttc accgagcgcg acgaccggct cgaagggcac ctcacctaca  19680
acaccgatct gttcgccgcg gacgccgccg cgcggatggc cgcgcagctg gtcaccctgc  19740
tcgaggacct cacccgccgg cccgcggtcc cggtggccgg gctggccgtg ctgccggccg  19800
ccgagcaccg tcgggtgacc gaggagtggc cgcactccgg gcccggccgg gagccgcgta  19860
ccgcaccgga gttgttcgcc gcgcaggtcg cgcggacccc tgatgcggat gcgctggtct  19920
ccgacgagga gacgctcagc tatgccgagc tggacggccg tatcaaccag tgggcgcggc  19980
tgctactggc ccggggtgcc gggccggaga cgctggtggc ggtggcgctg ccccgctccg  20040
cgcagatggt cacggcgatc ctggcgatcc agaagaccgg tgccgcctat ctgccgctgg  20100
acccgaagag ccccgcggaa cgcaaccggc tgatgatcga ggacgcccgc ccgctgctgg  20160
tgctgacctc ggccgggttc ggcgacggcg cggaactcgg cgcgcccgca ctgttcctgg  20220
acgacccgga cacccgcgcc gccgcaggcg agctgtccgc cggcccgctg gcggccgccg  20280
agctgcccgc cccgctgctg cccggccacc cggcctacgt catctacacc tccggttcca  20340
```

-continued ccggccgccc caagggcgtg gtggtcaccc acaccggtgt gcacggcctc gtggcggcgc 20400
agtcggcgca cttccgtacc gggcacggcg cgcgggtgct gtcgttcgcc tcgctcggct 20460
tcgacgcggc cttctccgag ctgggcatgg cgctgctgtc cggcggtgcg ctggtcgtcg 20520
tcgaccagga gcggatcctg cccggacagc cgctggccga cgtgctggcc gagcaccggg 20580
tcacccatgt gacgctgccg cccagcgcgc tgtccgcgct gaccccgggg acgctgccga 20640
aggacctcac cctggtcgtg gccggcgagg cctgcccgcc cgcggtggcc cgcacctggt 20700
ccgcccatca ccgcatgatc aacgcctacg gccccaccga gtccacggtc tgcgccagca 20760
tgagcgccgc gctgaccccg gacaccgtca gcggcgactc ggtccccatc ggccgcccgc 20820
tctccggcgt ccgggtcagc gtcctggacg accggctgcg cccggtgccg gccggcgtcc 20880
ccggcgaggt gtatctctcc ggcgccgcgc tggcccgcgg ctacctcggg cggctcgcgc 20940
tgaccgcgga gcggttcgtc gccgacccgt acggtccgcc gggaagccgg atgtaccgca 21000
ccggcgaccg cgcccgctgg ctggccggcg gcgacctgga ctacctgggc cgcaccgacg 21060
accaggtcaa actgcgcggc ttccggatcg agctcggcga ggtcgaggcc gtactgtcgc 21120
gccacgacgg ggtcggcgcg gtggccgcca cggtgcacaa ggacgagcgg ggcacccgcc 21180
gcctggtggc gtacgtcgtc ccggcgcggg aggacgcggc cgacccggcg cggctgcgcg 21240
agttcgcccg cgaggtgctg cccgagcaca tggtgccctc ggtcttcgtg ccgctggacc 21300
ggctgccgct gaacgccaac ggcaaggtcg accggcgggc gctgcccgca cccgacatcc 21360
ggcgcgacga gggcagcgcc cgtatcgcgc cgcgcacccc ggcggaggag acgctggcgc 21420
gcatctggtc ggaggtgctg ggcgtcacgg acatcggcgt cgaggacaac ttcttcgacc 21480
tcggcggcga ctccatcctc agccttcagg tggtggcgcg ggcccgggcc gccggactgc 21540
ggctgaccgc caagcagacc ttcctgcggc agaccatcgc cgatctcgcc gccgacgccg 21600
tcgccgagac cgaccccgcc gcgcacggtg cggccaacga cggcccggtc accggcgagc 21660
tgccgctcac ccccatccag cactggttct tcaactccct cggcgacagc ctggagcagt 21720
tcaaccagtc gctgtatctg gagctggccg agggccccga cctcccggcg ctgcgcgccg 21780
cactggccgc gctgaccgaa cagcacgacg cactgcggct ccgcgccgta tccgaggacg 21840
ggcagtggcg gctgcaccac gcgcccgccg agaccggtca actcctcgaa cacctcgatc 21900
tgtccggcgt ctcgcccgac gagcaggacg ccgcgatggc ggccgccgtc gacgcggcgc 21960
agcgggactt ccggctgtcc gaggggccgc tgctgcgggc ccggctgttc accctcggcg 22020
acgcccggcc gccccggctg tacctcgtcg cgcaccacct cgtcatcgac ggcatgtcct 22080
ggcgcatcct gctggcggac ctggagaccg gctaccgcct ggcggcggac ggccggccga 22140
tcgacctggg gccccggacc acctcgttcc gcgactggtc gcgccggctg tcgcgccatg 22200
tcgcggacgg cggcctggac gccgaactgc cgtactggaa gggcgtacag gacgcggcgc 22260
gcgagaccgc cccgctcccc gtcgacaccg gcgggctccc cgaccgccag ggcgcccagg 22320
aggagcccgg cgagaacacc gccgggtcgg cccgcaccgt ctccgtacag ctgtccgccg 22380
cgggcaccga ggcgctgctg cggcaggtgc ccgaggccta ccgcacccag atcaacgacg 22440
tcctgctcag cgcgctgggc cgggtgctga ccgactgggc gggcggcgag cgggtgctga 22500
tcgccctgga gggccacggc cgcgaggagc tcttcgacga ggtggacctc acccgcaccg 22560
tcggctggtt caccaccctc ttcccggtcg ccctgcggat gccggccgac cgggactggg 22620
gaacggtcct caagagcgtc aaggaacagc tgcgggcggt gccccacaac ggactcggcc 22680
atggcgcgct gcgtcatctg gcagggccca actcccctct ggaggacggt ccggagcccg 22740

-continued aggtcagctt caactacctc ggccagctgg acgtgtccgc cgaccgcacc ggcctcgccc 22800
gcgccatgct caccagcgag ggcgccgagc gggccgccgg ccagcaccgt gcgcagctgc 22860
tggagatcaa cggcgtggtc accggcggcc ggctggagtt ccactggacg tactcggtga 22920
accggcaccg cgcagagacc gtcgaacggc tcgccgcggg cttcatgacc gcgctggaag 22980
cgatcgtggc gcactgcgcc gcccccggtt ccggcggcgc caccccgtcc gacttcccgc 23040
tggccgccct cgaccaggcc accgtcgaca agatcgccgg cgacggccgc acggtcgagg 23100
acatctaccc gctcaccgcg atgcagagcg gcatgctctt ccacgcgctg agcgagtccg 23160
gacgcgaccc gtacaccggg cacttcggcg tccgcgtgga cggcatcacc gacccggggg 23220
cactggccgc ggcctggcag caggtcgtcg accggacccc cgccctgcgc accgccatcg 23280
tctggcagga cgtcgcggaa ccccttcagg tggtgcacgc ggccgcccgt gtgccggtca 23340
cccatcacga cctgcggtcc ctgaccgagc aggaacggca ggccgccctg gaccggctgt 23400
gggagcggcg cgaggagacc gtcatcgatc tcgccgtcgc gcccgcgctg cggctgaccc 23460
tcgtccggct caccgacagc gccgtccaga tgttctggac ctcgcaccac atcctgatgg 23520
acggctggag cttcgccggg ctgctgtcgg aggtgtgcgc ccagtacacc gcgctgaccg 23580
gcggcccccg cgtggcggcc ccggcccgcc gcccgtaccg cgactatgtc ggctggctgg 23640
ccgaacagga ccagccggcc gccgaggcgc actggcgctc ggtggtcgac gggttcacgg 23700
tgccgacgcc gctgccctac gaccggcagc cggtgaaggc acacggcacc cggtcctcgc 23760
gtgaggtgcg gctgcagctg tccgccgagc gctccgggcg gctgtccgag gccgcccggt 23820
cggcgcggct gaccgtcaac acgctggtgc agggcgcctg ggcgatcctg ctggcgcgct 23880
acggcggggt gcgcgacgtc tgcttcggca ccaccgtctc cggccgtccc gccaccctgc 23940
ccggcgccga gtcgatggcc gggctgttca tcaacaccgt gccggtacgg gcgaccatcg 24000
acggtgccgg tgccggcgac ggcgccgcca ccggcaccgt cgagtggctg cggcggctgc 24060
agagcgagca gctcgactcc cggcagcacg agcatgtctc gctggcgcag atccagcgct 24120
ggagcggcgt accggccggc accaacctct tcgacagcat cgtcgtcttc gagaactacc 24180
cctacgacag cgatgcggcc gccaagtacg ggctgaccct cggcacgttc cagggcgacg 24240
aggtcaccaa ctacgccctc accctgaccg cgtacgtggc cgacgagctg catctcaacc 24300
tcggctacga cccggatctg ttcgacgagg cgaccgtcga gcggatggcc gggcatctgg 24360
cgacgctgct cgacgccgtc gccgccgccc cgcacacccc ggtggacgac ctcccgctgc 24420
tcgatgcggc cgaacaccac cggcttctca ccgagtggaa cgacaccgcc gccggcttcc 24480
cgccgccgcg gccggtccat gagctcttcg ccgagcgggc cgcccgtacc ccggacgcgg 24540
tggcggtcag cgacgccacc cggcagctga ccttcgccga gctggagacc cgcgccaacc 24600
aactggcgca ccacctggcc ggtctgggcg tggcgcccgg cacgctggtc ggggtgtgcg 24660
ccgaccgcgg ggtggacgcc gtggtggcgc tgctgggcgt gctgcgggcc ggcggtgcct 24720
tcgtaccgct ggaccccgcc tatccggcgg agcggctcca ggtcatgctg gaggacgccg 24780
cggtgccggt cgtggtgacc gaggagcggc tgctggaccg gaccgccggg cacgacgcga 24840
cgacggtgtg cctggaccgc gatctgccgc tgctggagga gctgccggcc cgcccgccgt 24900
acaccgccgt ggcaccggac gacctggcgt atgtcgtcta tacgtcgggc accaccgggc 24960
gccccaaggg cgtgatggtc gagcaccggc acgtccacca catggtgcac gcctgggacc 25020
ggcgctacgg gctcgccgcg ctgcaaccgc gcgcgctgtc cgtctccagc atctccgtcg 25080

-continued

```
acctgttctt cagcgacttc ctgctctccg ccctcttcgg cggcacgatg gtgatctgtc  25140
cgcaggacgc cgtcgccgac caggtggcgc tgaccgatct gctgctcaag agccgggccc  25200
agctgatggt gacggtgccg acgctggccc gcgcggtggt cgccgagctc gcctggcgcg  25260
gtgtgacacc ggaggcgctg cgggtgctga tggtgggctc cgagggctgg ccggccgatg  25320
ccgcggccga gatcctggcc ggtctcgcgc cgggcacggt gctggtcaac gcgtacggat  25380
cgaccgagac cacggtcgac tccacggtct tccagctcgg ccgcgacccg ctgggcgacg  25440
ccgccttcgt accggtcggc aggccgctcg ccaacacccg gatctatgtg ctggacgagc  25500
ggatgcgccc ggttcccacc ggcgtcgtcg gcgagtgcta catcggcggc gacggagtgt  25560
cgcgcggcta tctgggccgc ccggagctga ccgccgagcg tttcctcgac gacccgttcg  25620
cgccggagcc gggcgcccgg atgtaccgga ccggtgacct cgcgcgctgg cgggccgacg  25680
gcaacctcga atgcctcggc cgggtcgacg accaggtcaa gatccgcggc ttccgggtgg  25740
aactcggcga ggtggaggcc gcgttggccc gccacccggc gatcgactcg gcggccgccg  25800
cgatccgcaa ggacgacggt gggccggccc gtctggtggg ctatgtcgtg cccgccgccg  25860
gccacacccc cgacctggcc gagctacggg ccttcgccgc cgaacggctg ccgtcgcccg  25920
ccgtccccac cgcgtacatg gtgctggacg cgctgccgat gacgccgagc ggcaccgtcg  25980
cccggcgtgc gctgccggcc ccggccgggg cgcaggacgc cgcccggccc tacaccgcgc  26040
cgggcagcgc caccgagctg ctgctctgcg gtatctggca ggaggtcctg ggcgtcgaac  26100
gggtcggcgt gcacgacaac ttcttcgacc tgggcggcga ctcgatcctc agcatccggg  26160
tcatctcccg gatccgggcc acgctgggcg tcgccccgtc gccccgccag ctcttcgaca  26220
ccccgacggt ggccggtctc gccgccaccc tcggccggga cgacccctcg gcggccgccg  26280
acgtccccct ggagccggcc gaccgcggcg caccgctgcc gctgtcgtcc gcccagcaac  26340
gccagtggtt cctgcacaac ttcgacccgg acagcagcga gtaccacatc gtcaccgggc  26400
tccggctcga cggtgatctg gacgtcgcgg cgctgcgagg ggccctgaac gggctcgtcg  26460
cccggcacga ggcgctgcgt accacctacg cggccaccgg cgagggcgcc gagcagatcg  26520
tgcaccccgc gggcgaggtg gtctgcgagc gtacggatct gtccgaggtg cccgaggacc  26580
agcgcgagga caccctgcgc gggcacatcg accgcgccgc cgcccggccg ttcggcctca  26640
ccgagggccc ggtcctgcgc gccgaactgt tccggctcgg cgcccgtgac catctgctgc  26700
tgctcgtcat ccaccacatc gccaccgacg gtgtctcgat gcaggtgctc accgaggagc  26760
tcggcgtcca ctacgccgcg gcgctcgacg gcacaccgcc cgccctgccg gcgctgccgg  26820
tctcctacgc cgactacgcg gcctggcagc gccggatgct gtccggcccg gcgctggacg  26880
gccatctcgc ctactggcag gagcggctgg ccggtgtccg gccgctggag ctgcccaccg  26940
accggccccg gccggcggtc cgcagctccg cgggccggat gctgctgatc gagatcgagc  27000
cgcgggtggc cgcgggcctc aaggaactgg cccgccgcca tgacgccacc ctgttcatgg  27060
cgctcaccgc ggcggtccag ctgctgctgg cccgctacac cggacagccg gacatcgtcg  27120
tgggcacccc ggccgccggc cggggccggc aagaactcga ggggctcgtc gggctgttcg  27180
tcaacacggt ggcgctgcgg tccaccgtcg acgagagcgg gaccttcgac gccttcctcg  27240
gtgcggtgcg cgacaccgtc ctcgaagcgt ttgtgcacga ggacgtgccg ttcgaccggc  27300
tggtcgaggt gctgcgaccg cgccgcgacc ccagccgtaa cgcactggtg gaggtgttcg  27360
tcggactgga gacggaccgg tcggcgccgc cggcgctgcc cggactgacg gtgaccgagg  27420
tcccgttcgt cagcggcgag gtcagccatg acctcagctt cgacttcgtc gacgggcccg  27480
```

-continued

```
acggcctgaa ggcggccatc ggctacagca ccgcgctgtt cgacgacggc accgtcgagc  27540
ggatggccgg ccagttccag gcgctgctcg ccgcggtcct ggaggaccat cgcgcgctcg  27600
ccgacatcgc acccgcggac gaggccgagg tgcggcggct cgccgaactg cggcaggccg  27660
cgccctcgga gcccgacgcg tcggaaaccg acggcgcgcc ggccgcctac cgcgcgcccg  27720
ggaccgctgc cgagcgggcc ctggcggaga tctgggccgc cgtgctgggg gtgccgcggg  27780
tcgggaccga cgacaacttc ttccagctgg gcggcgactc cctgctcagc atccaggcgg  27840
tgcagcggat gcggcaggcc ggcctggcgg tgaccaccaa ggatctgttc gtccaccaga  27900
gcatcgcccc gctggcggcc ctcgccgagg aacgggcggc ggaccggccg gaggcccccc  27960
aggcgcagca cgacgatgcc gggacggcgg gcgagatacc gctcaccccg atccagcgcg  28020
actacttcgc ggccgggccg ctcgccccgc accacttcac ccagtcggtg ttcctcgaac  28080
tgcacgccga tctcgacgag ccggcgctgc ggcacgcact ggccgcgctg atcggccacc  28140
acgacgccct gcggacccgc ttcgtacgcg aagacggcga ctggcggcag tacgccaccc  28200
cgccggagcc ggtggacatc ctgcgccggc acgacctgtc cgggctgccg gaggctcaac  28260
gggccgccgc catggacgag ttggcggcct cggccgacgc cgggctcgat ctggcggccg  28320
ggccgccggc cgcggcgctg ctgttcgtct tcgggcccgg ggagcggccg gcgctgttcg  28380
tgaccgcgca ccatctcgtc gtcgacggcg tctcctggcg gatcctgctg gaggacctgg  28440
aagccggcta cgtccaggcc cgcgacggga agccggtgtc cctgggcgcc aaaagcacct  28500
cgttcgggca gtgggcgcac cggctcgccc ggcacatcgc cgacggcggc ctcgccgagc  28560
aggccgccta ctggcaggcg ctgcccgacg gcaccgaggt cccgcacgac ggctcggggc  28620
ccgcggtggt ggagtccgtg cagaccgtca cggtggagct gccggaggac accagcgagg  28680
tgctgctgcg ccggtccgcc ggggtcttcc ggacccgctt ccacgaggtg ctgttcgccg  28740
cgctcgccgg caccctggcc cggtggacgg gcgaacgcca ggtcgtgttc gacaccgagg  28800
gccacggccg ggaggacctc ttcgacgacg tcgatctctc ccggaccgtc ggctggttca  28860
ccaccgagta ccccgtcgcc cttgaggtgg ccggcgaccg ggacgactgg ccggcgctca  28920
tcaggtcggt acgcggacag ctgcggtcgc tgcccggcaa cggcttcggt tacggcgcgc  28980
tgcggcatct gagcccggcc ggcaccccgg gtgccgcact cgccgaacgg gccccggccc  29040
aggtggtgtt caactaccac ggccaggccg acgaggcgca gcgcgcggcg gagagcgacc  29100
tctaccacgc gttcggcgac ccgatcggcc gggagcagcg gcccgacgag ctgaccgggc  29160
acccggtgga ggtggtgggc gccgtgcact ccgggcggct ccgcttcacc tggtacttct  29220
cgcgcaatgt tcatcacagg gccaccatcg acaaggtggc cgaggacttc gccgacgcgc  29280
tgcgcgccat cgcccggcac atcacggagc ggtgagccat ggaccacgaa agcctgcaca  29340
gcaccctgac cgaactggcg gcccgccatc gggtgcccgg cgcgcagctc gccgtcatcc  29400
acgagggga acggttcctg gtgcacaccg gagtgtgtga caccgcctcc ggagcccccg  29460
tggagcggca caccgccttc cccgtcggct cgctgaccaa gccgttcacc gccgccctcg  29520
cgatgatcct ggtggccgac ggggacgtgg acctggacga gccgctgagg gggcagctgc  29580
cggagttcgg ggcgggcgaa ctcgtcaccc tccggcagtt gctcagccac acctcgggcc  29640
tgccctccga tgtgccggag ggcagcgacg aggccggcgg cggcgaccgt gcccgctggg  29700
tggcccggta ctgccgtacg gcggatctca cgcatgcgcc cgggacggtc ttctcgtact  29760
ccaacatcgg ctatgtcgtc gtgggccggc tcatcgaggc ggtcaccggc atgagctggc  29820
```

-continued

```
aggaggcgat cagcgcgatc ctgctcgaac ccctgggcac ccggcccgcg ttcgtcgtcg  29880
gagcccccgc cacccgtccg gtggccaccg ggcacgccgt ccaggcggtc cgcgaccggg  29940
tggtgccgat accggaccag gatcttcccg aggtcgagat gcccaacggg gcgctggcgc  30000
tgagcgccga ggacctggtc ggcttcgccc ggctgtactt cgccggctgc ccggaccctc  30060
agccgctgga ccgggcgacc gccgacgaca tgtgcttcga ccagctggcc tcgatcgcca  30120
tcggcccgta cggcatggcc gacggctggg gcctgggctg ggcgaggttc gacgacggtg  30180
cggcggacgt ctacggccac aacggcaccg gcgacggcac ctcctgtcat ctgcgcttcg  30240
acccggccaa cggctccgcg gtcgcgctga ccgccaacgc caacaccggc gcccagctgt  30300
gggacgccct ggtgccccgg ctgcgggcca tgggtctggc ggtcggcgac cgcccggcgc  30360
ccgagccgcc caccaccccg ccgccggtcc cggacgactg tccgggccgc tacaccaacg  30420
gcgacaccga gttcgtggtg cagcccggcg ccgacggcgg gctgctgctg agcttcggcg  30480
gggcgccgca ctcggagctg ctgtgctccc ccgatctgcg cttcaccatg cgggagctgg  30540
gcagcggtgc ccggtccccg ggccgcttcg tgaccgatcc cgccaccggg cggatcggct  30600
acctccagat caccgggcga ctcgcccccc gacgctgaga cagggacggc ccccgggatg  30660
accacggccc ccacggacgc ggagacggca cgcggcagcg cggccgtccc gctgtcccgc  30720
aaccgcgact acaacatcct gtggtccagc cagctgatgt ccgaactcgc catggagatg  30780
gccgcggtag ccgtgccgct gctgatcctc gcccggcacg gctcaccgct ccagctgggc  30840
ctggcctcct ccgcgatggc ggccgcgcac atgatctcgg tggtgccggc cggggtgatc  30900
gcggaccgct gggaccgccg ccggctgatg ctgggctgcc aggtgctacg ggtgctgggc  30960
atggtgagcc tggccggcgc gctgctgctg gaccggtacg cgttctggca tgtgctgctg  31020
gtcgtggtgc tggagggctt cctcggctcg gtcttcgacc ccgcggaaca tgccgcgctg  31080
ccccaggtgg tgccgcccga ccagctctcc acggcggtgg ccagaaacgc ggcgcgcccc  31140
tacatcgcca ccctcgtggg gccgggcgtc gccggtttcc tcttcagcgc cctgccgctc  31200
gggccgttcg cgaccaatgc ggtgatgttc gcgctgtcgt ccgtggcgct gtgctttctg  31260
cggctgcccc gggggcggtc cgccgtggtc cggaccggcg acgggcccga cagcgccgga  31320
gcggaccacg acaggccgga ccacgacgga cgggacgacg cgaacgacga cactgcgccg  31380
cggcccgggg gcgccgccca ggacttcgct gccggcttcc gctgggtgct ggggcagccg  31440
gtgatccgca ccacgatggc ctggatgatg atcacgaacc tggtcttcag ctcgctgctg  31500
atcgtgctgc tcgcgctctc gggcgaggac aaggtcggcg ccggtgagct gggtctgacg  31560
atggcctgct tcggcgccgg cggactgctc ggcgggctct tcgcggcccg gatgcacgcc  31620
gccgcccggc caccggtgat cctcctcggc ttcacctgga ccgccgccct gggcgccgcc  31680
ctgatggcgg tggtgcccac cggtctgccc cagggagcgc tgctcggcct gatggcgctc  31740
ttcgccccgc tcgccaacac caccgtgctg acctaccagt tgaccgtcac cccggacgag  31800
ctgcggggcc ggatgagcgg cgtcgccggg ttctgctcgg ggggcgccgg tgtcctgggg  31860
cccgcgctcg gcggtgcgct gacgggggcg gccggcgggg gcgtgacccc cgtactcatc  31920
tgcgccggct gcctggtcct ggtcgctgtc gcggccaccg cgagccccac gctgcggcgg  31980
tttcccgaca tcgcggaccg gcagccctga cctgctgcga cacggcccgt gaccggccaa  32040
cttaactcca cagtcaagga catggaacgc ccggacgaat ccgacgatgc tcgtgtatca  32100
actggagatt tccgcgcgtc ctcggtgcgg gggctggtgc ctgtccggcg gtgtgccgcg  32160
cggtcggcga aaggtcccgt atgcagaccc cccacacacc gagccaggca cagtcccagc  32220
```

-continued cacggcaaaa gccgcagccg ccgtcgcagt cgcagtcgca gtcgcagccg aatctgaggt 32280
ccctgaccgg attacggttc ctgggcttat tacccgtctt cctcacccat gccgcgttcg 32340
agggcgtctt cagcgacgcg gacgtgagct ggggcttcct cgacgcgatg gggaacaccg 32400
gctatgccgc ggtctcgttc ttcttcgtgc tgagcggctt tgtgatcacc tggtcctacc 32460
gctcccgcga caccacccgc acgttctggc gccgacgcgc cttccgggtc ttccccaacc 32520
atctcgtggc ctatgtgttc gcgctggctc tgatgctcgc ggcgggcgcc gccttcgacg 32580
cccccgccct gatctcccag atgttcctgg tgcacgcatg ggtgcccgac ccgctgttca 32640
tcgacaccgg caacacggtg acctggtccc tcggggtcga tgtggtgttc tacgggctct 32700
tcccggtgct gctcgtgctg gtgaacaaga tcaagccaac ccgtttgtgg tactgggccg 32760
gtgctgccgt gctcatggtg atcgccatcc ccacagtggc gctgaccctg ctcccggaca 32820
ccccggccat gtcggtgggc gatgtctccc gcagccagta ctggttcacc tacttcttcc 32880
cgctctcccg aaccgtggag tgcgtgctgg gcatgctgat ggcgcggatc gtgctgtccg 32940
gcaagtggat aggcctgcgg gtgctgcccg cctcggccct ggtggtcgtg gggtatgtcg 33000
tcgcacagca actccccttc ctctaccggc tcagcgcggt gctgatcgtg ccgatcgtgc 33060
tgctcaccgc ctccgtggcg gtggccgacg ccgagggccg ggggaccccg ctcggcggca 33120
aggtcatggt ccggctcggt gaactctcct tcgccttcta cctcgtgcac caggcgctcc 33180
tggcgtacgg gcacatcctg atcagcccga agaacgccca gggcgaggtg ctgccccgta 33240
cctgggacac gcctggcggc atcgcggtga tcgtcctgtc gttcgtggtg tccctgggac 33300
tcgcgtggct gctgcacaac ggggtggaga agccggtgat gcgccgttgg tcccggtcca 33360
ggcgccgcgt cacccagcag ccgccggcaa aggtgccggc aacttagctg cgaagtgaaa 33420
cgtgtggagt gcgcgaaaga tctcggccaa actccggcgc aacgggggag taaggctgac 33480
cgctgccaga agtccgcgcg cgccgtggat gtccggtgcc ggcgaccacg cccggatcat 33540
ccatcagccg acagtggtgc ggccgccgtt gcggcgcacc gagccgcacc gcctgtcgcg 33600
catctggcga gaggtccgca tgcagacaag acaatccaac ccgaacctga gatccctgac 33660
cggtttgcgg ttcgtggcga tgctgccggt cttcctcacc catgcggcgt tcgagggcgt 33720
cttcagcgac gcgaaggtga gctggggctt cctcgacgcg atggggagca ccggctatat 33780
ggccgtctcg ttcttcttcg tgctcagcgg ctttgtgatc acgtggtcgt accggcccac 33840
cgacaccgcg cgcaagttct ggcgccggcg cttcttccgg gtcttcccca accacgtcgt 33900
gacctatgcg ctcgccctcg ggctgatcgc tgcggtgggg ctgagtgtcg gcgtactgcc 33960
ctcggtcacc cagctcttcc tcgtccagtc ctgggtgccc gacccggcgt tcaccgacac 34020
cggcaacagc gtgagctggt cgctcgcggt ggatgtggtg ttctacgcgc tcttcccggt 34080
gctgctcacg ctggtgaaca agatcaagcc gaatcggctc tggtactggg tcggtggctc 34140
cgtcatcggt gtggccgtgg taccggccat cgcgctcgcc gcgctcccga gcacccccga 34200
gatgccgctc ggcggggtgt ccgtcagcca gtactggttc acctacttct tcccgctctt 34260
ccggctgctg gagtgtgtgc tcggcatgct gatggcgcgg atcgtgctgt ccggcaagtg 34320
gatacgcctg cgggtgctgc ccgccgccgt cctcgtggtg atcgcgtact acttcgccca 34380
gcaggtcccg tacctctacc ggctgagtgc ggtgacggtg ctgccggtcg cgctgctgac 34440
ggcggcggcc gcggtggcgg actccgaggg ccggggcacc ctgttcggca gcaaggtcat 34500
ggtctggttc ggcgaactct ccttcgcctt ctacctgctg cacaacctcg tcctgaagta 34560

-continued

```
cggccatctg ctgctcggcc acaccgagga ggagggcgag ctggtgggcc acacctgggg  34620
cgtgcccgag ggaatcgccc tgatcgccgc cgccttcgcg gtgtccctgc tgctggcctg  34680
gctgctgcac aacggagtgg agaagcaggc gatgcgccgc tggtcccgac gcaagccggc  34740
tccagtggct gaagtaacca gtgggttcta tgcgaaggac ggggcaattt agctaggaag  34800
taaaggttat ggaacgggct gtcgaaagac ggcaagatct ccactgatca ggcgttcggc  34860
accggattcg atcaatcagg tgccctatct ggagggacgt gtacgtgctg acgctccacc  34920
tgcaggatga cgacgtcgcc gcgatcgacg ctgtggctga cgaactcagc cggcgatacg  34980
actccgtgga gtccacggag ttccaggccg agagccgcct ctacgcggac gagttgccac  35040
gtcgcgtgcg acgagcgctg cacgaatacc gcagcaccga gaagtccggc atcctggtcg  35100
tcaccggcct gcccgtggac gactcggcgc tcggggcgac cccggccgac cgcccggcaca  35160
agccggtgcc gtccacgtca ctgcgccagg acatcgcctt ctacctcata gccaatctgc  35220
tgggcgaccc catcggctgg gccacccagc aggacggctt catcatgcat gacgtctacc  35280
ccgtccaggg cttcgagcac gaacagatcg gctggggcag cgaggagacg ctcacctggc  35340
acaccgagga cgccttccat ccgctgcgca cggactatct cggactgatg tgtctgcgca  35400
atccggacgg cgtcgagacc accgcctgcg atatcgccga tgtcgagatc gacgacgaga  35460
cccgggagac cctctcgcag gagcgcttcc ggatcctgcc ggacgacgcg caccgcatcc  35520
acggcaaggc cccgggggac gagagcgcac gcgagagtgc gctgcgtgag cgcagccggc  35580
agcgggtggc ctcggccctg gagtcgcccg acccggtggc cgtgctcttc ggggaccgcg  35640
acgacccgta tctgcggatc gacccgcact acatgcaggg cgtccagggc gagaccgagc  35700
agcgggcgct ggagaccatc ggcgccgcga tcgacgacgc catgtccggt gtcgtgctca  35760
gccccggtga catcgttttc atcgacaact accgcgtcgt ccacggacgt aagccgttcc  35820
gtgcccgctt cgacggtacg gaccgctggc tgcggcggct caacatcgcc cgggacctgc  35880
gcaagtcgcg cgaggccagg ctcgccgcca ccacccgcgt catctactga ccggctgccg  35940
ccgatcagtt agcgcaggca ccggccgaac caccgggcgc ctgcgcccag atcgcgccgc  36000
tcaacacacg gcaccgacgg ggaccgccgt catggcggtc ggccgctgtg tgcccatgcc  36060
ctcccgcatc tggggaaccc tttacgtctc tgcgaggtac ctgtgtccgg aacgcagcaa  36120
gtaaaagccg ctttggggga ttccgaaggt gacaccggaa acctcaccca actggagttc  36180
ctggctctga acagcgagtt caacatcgct gacggccacg cccggcaggc gctcacgccg  36240
ggccaaagca agatcgtcga cgatctgccg ctgctcttcg ccgagggcga gaagcggccc  36300
gtcgaagagc tcgaacgcga ggcgcaccac gccttcttca cctgccctcg gccagcacag  36360
ctacccctcg gcccccggcc gggtgctgag ctgctactcc tcctcggtcg cgatggagat  36420
cctctcccgc tcgctgtccg agacgatcga gtcggtggcc ctggtccacc cgaccttcga  36480
caacatcgcc gacctgctgc gcggcaacgg cctgaagctg gtgccgctgg cggaggaccc  36540
gctgcacggc gacgacctcg acgtgagcct gctgaagtcg gtgggctgtg tcttcctcac  36600
cacgcccaac aaccccaccg gcaaggtcgt ctcccgggag cggctgaccc ggctggccga  36660
gcagtgcgcc gagcacggcg tcatcctcgc gctggacacg tccttccgcg gcttcgacac  36720
ccgcgcccac tacgaccact acgaggtgct caacgccagt ggtgtgcgct gggtggtgat  36780
cgaggacacc ggcaagctgt ggccgaccct cgacctcaag gtcggcatgc tcgtccactc  36840
cgagaacctc gcgctgccgg tcgagaagat ctactccgac atcctgctcg gtgtctcccc  36900
gctgatcctc gcgatggtcc gccgcttctc cgaggacgcc gcggccggcg gtctggagga  36960
```

-continued

```
tctgcaccgc ttcatcgccg ccaaccgtgc catggtgcgc gcggaactcg ccggtctgcc  37020
gggcgtcacg gtccccgacc ccgacagccg ggccagcgtc gagcgggtcg ccatcgatga  37080
cctgacgggc acgcaggtct gggcgaagct gcgggagcac aacgtctacg cgctcccgtg  37140
ccgcccgttc cactgggcca acccgtccga gggtgaccac accctgcggc tcgcgctggc  37200
ccggtccacg gacccgctcg cccagtccgt gcgcgccctg cgccacgtgc tgaaacagcg  37260
ttgatgacgc ctgtcgcaga aggaggactc ccgcacggct ccgtgccctc gctgtcgcac  37320
acgcggcagt ggcggcccgg ggtcgtgcag gaggtcgccc cggccggcgt cctcgacctg  37380
ggccccggct acatcgagcc ggcactcctg cccgtacgcc tgctgcgggg cgcgtacgag  37440
caagcgctgg cggagtacgg cgccgcggcg ctgggctacg gtcacgaccc gggcgcgcag  37500
ccgctgcgcg accggctggc cgcccgcgcc gccgcggcgg acggcctccc ctgcgacccg  37560
gaccaggtgc tgctgacctc cggcacgtcc caggccctct atctgctggc gacctcgctc  37620
gcggccccgg gcgacacagt gctgacggag gagctctgtt acgacctggg acagcggata  37680
ttccgggact gctcactgcg gctccgccag gtcgccatgg acgggtcggg gatgctgccc  37740
gacgcgctgg accgcgccct gaccgagggc gcgcgagcgg gcgcgaaaac cgctttcgtc  37800
tacctcaccc ccacccacca caaccccacg ggccacacga tgccgctggc gcgccgccgc  37860
ctgctgctcg aagtggccgc ccggcacgat gtgctgatcg tggaggacga cgcctacacg  37920
gaactgtccc tgatccctga ccgcactccc ccgccctcgc tggccgccct ggccggctac  37980
cggcgggtgg tgcggctgtg cagcttctcc aagaccctcg gccccggact gcggctgggc  38040
tggctgctcg ccgaccggga actggccggc cggctggcca cgcacggcct gttcgtcagc  38100
gggggttcgc tcaaccacac cacctcgctc gccgtgagca ccctgctcgc gagcggcgcg  38160
tacgaccgtc atctcgacgc gttccgggcg cagttgcgtg ctcgtaggga cgcgctcgtg  38220
ggcgctctac gcgcgatgct ggacgacggg gtggagctgc gcaccccgga gggcggattc  38280
ttcctgtggc tgcgggccgg ggacggggcc gacgagcgtg agctgctcga cggcgccgcc  38340
cgggcgggcg tcaggatcgc cgccggatcg cgcttcggca caacccaggg ggccggcttg  38400
cgcctggcct tcagcttcaa cccgcccgcg ttactggagc aggccgccaa gcggctgacc  38460
accgcatggt ccggcagcac gccggacctc gagatcggag tgagatcgtg acgaccagca  38520
ccgggaccaa cggccggcac acggtggccg gtccaggcag cgccggtccc gtcgggtaca  38580
gcctgccgct ctcgccgacg ggcgagtcgg cgatgctcac accaccgccg tggcacttct  38640
ccggcgaggt cgtcatggtc gactaccgcg tcgacccgga cgcggcccga cggttcctgc  38700
cgccgggcct ggagccgggt gccgacccgg gcgccgcggc ggcggtgttc gcgacctggc  38760
agtggtgttc gcaggacgga gcggagctga ccgaccccgg tcgctgccag ttcggggagt  38820
tcctgatcct gctcagctgc gagttcgagg gccgtcccat ggcgcgctgc ccgtacgcct  38880
gggtggacca ggccgtgccc atgatgcgcg gctgggtgca ggggatgccc aagcagttcg  38940
gcgtgattca ccagagccgg cccgtcacgg tcggcaaggc gggctcccgg ctggcgcccg  39000
gcggtcgttt cgacggcgcg ctgtccgtgc acggacgacg cgtcgtggag gcctcggtca  39060
ccgtggacag gtcgacggac cagccgccgg cgctgcacga tgttcccctg gcgcacaccc  39120
tggtgttccc ggagtgggtg ccctccggcg gcgggccgcg accacggctg gtcgcctccg  39180
aggtaagcga tgtggaattc tccccgatct ggaccggatc gggtgatctc acgttctttg  39240
acggactggg ggatgatttc ggggcgctcg caccgttgga agtaggtagc ggccacgtgt  39300
```

-continued

```
tctcgtacgg ggagaccttg cacggcggcc ggctgctcag cgactactcg gtatcagaac  39360
gacatcagcc atgaccacgg gggacaaagt gctgaggatc cacttcacag ttgaggacat  39420
agcaaatacg cgcatgctgg cgaccctcgg gccgctggcc gagagcgctt tcgcgctcta  39480
tctgttcggc cgtaacggcg atgtcgcctt tcacgagtgg cgtcgcagtg tccgcgccga  39540
actcggcaag gacgcggccc gcttcacggc cttgtcccag cagttccgga ccctggagga  39600
attacctgcc gccttcgccg acgccttcac gccgggggcg gaccccgacc aggttccgtc  39660
cggcgaggac cggcgcggcg ccaggctgct ggccgacctg tgccgggtgg ccgtgctgcc  39720
gcactggagc ctgatccgca gtcatctcga cggtgcgcgc gagggctggg gcagggtggc  39780
catctcgcac ggtgtcgagc ggctgctggg ctccgtgcac cccaaggtcc gctggcgggc  39840
gccggtcctc gaactgcggc acgggcccaa ccgcgacatc catctggacg gtcgcgggtt  39900
gctgctgtgc ccgtcgttct tcctgtcgga gcagtcctgt tcgttcgtga cggcggtcgg  39960
caaggacgcc atgcccgccc ttgtcttccc cgtgaaggcc tcgtccaggg tggacatctg  40020
gggtacctcg gaacacgacg agcaggcgct gggcgcactg gtcgggcaca ccagggcggc  40080
cgccctggaa gcgctcgccg agggctgctc cacgggcgaa ctcgccgacc ggctggggat  40140
ctcgctggcc ggtgccagca agcatgccgc ggtgctgcga cgatccgggc tggtgaccac  40200
ctcccgtaac cgcaacaccg cgctgcacgc gctcacccct ctgggcaccg ccctgctccg  40260
cagcagcgac cgcttcatct cgccgcctac cgcccccggta tcgcgcgtgc cggcgcaacg  40320
catgcggccc ttgcagctca acggcatcgg ccccggcacc aaccgggcgg cggtctgacc  40380
gcccccgcgg acggccaccg ccacgactta cggcacccct gacaggagag gacacgacag  40440
tgggcacaaa ccccttcgac gaccccgacg gccggtatct ggtgctggtc aacgaggaag  40500
accagcattc actctggccg gctttcgccg aggtgcccca gggctggacg gtggcgctcg  40560
cggaaaccga ccgtcagtcc gcgctcgact tcatcaccga gcactggacc gacatgcggc  40620
cgcgcagcct ggtgcgggcg atggaagagg cttagaccag ccttgccgta tcaggcgatt  40680
tctccgggac cggcggttct ttctcaaaga tcgctgccgg ccccggggaa gaagccccca  40740
cccgcccccg ccgtacggca gaattcctgc ccgtgactat tcgcttgctg atcgccgacg  40800
accaggagat ggtccgccgc ggaatacgcc gcatcgtgga gagccagccc gacatggaag  40860
tggtcggcga ggcggcaaac ggcgtggacg cggtggagat ggggcgcacg ctcaaacccg  40920
atgtggcgct ggtcgacatc cggatgccgc ggatggacgg cctggaggtg acccgcctgc  40980
tggccgaccc cgccgcggcc aacccggtcc gggtcgtcgt ggtgacgacc ttcgacctgg  41040
acgagtacgt gtaccccgcg ctgcgcttcg gcgcctcggg gttcctgctc aagcgctcgg  41100
ggccgacgct gctggtcgag gcggtccggg cggcgatggc cggcgacagc ctgatcagcc  41160
cgtcgatcac tgtccggctg ctccagcatg tcaccggccc cacgaccggc cgccgccccc  41220
gccgccgtga ctcggtgctg accgagcggg aggtggagat cgccgggaag gtcgccgagg  41280
gcaagaccaa ttccgatatc gcccgcgagt tgttcatctc cgcgggcacg gtcaagaccc  41340
atgtcgcgag cattcagcga aagctacagg tacgcaatcg cgtcggggtc gcggtgcggg  41400
cctgggagct cggatatgcc accgggcaga ccccggggtg aaaacccgcg gccggcatcg  41460
ggcagcacgc cacccggcag aaaccccgat gccgtcccgc ggaaatctgc cgtccggcag  41520
atgcggtaat ttccgcgctg tgcttgccgc cgcgcaaccc ggggaatgtg cgtagcctcg  41580
ccctcatgga ttacgacgtt cctccccggc aaaagcgccg ccggtggtgc ggggtggccg  41640
cggcaatgat gctcgccccc gccgtcatag cgccaccgag cgcctatctg ctggcggtca  41700
```

-continued

```
tggccgcatt gacgctggcc gtatcgatac ttgcctggcc gaccggccgg atctccctgg  41760
cccaggcggc gggcggcgtc gcgctgctct ccctcgccgc ggacgtcggc tacttcgggc  41820
agcccggcct ggtgatcctc tggtacccgt tcgagacggt cgcgctgctc gttctcctgg  41880
agcgggtggt acgtcatgtg cccagccccc gggtgggcat cgtcgccccg ctgaccggcg  41940
cagccgtcat cctgctgccc ctgcgcttca ccctgcacgc ccccaccgcc gggctcaagg  42000
aatcggtctt cgcggccttg ctggccctga tcccggcggc ctgcgcgacg ggtgtggggc  42060
tctatctgcg gtcgctggac aaccgccggg cgtatgccgt ggtgctggcg cgccgtgaac  42120
agcgcctcga agtcgcccgc gatctgcatg acttcgtcgc ccacgaggtg accggcatcg  42180
ttctggaggc ccaggccgcc caagtcagcg aggacgccgg gcccgaggag caccgcgccc  42240
ttctgcagcg catcgagaag gccgggctac gggcgctgga ctccatggac cagacggtga  42300
cgacgctgcg cgaggcggac ggccgcaagt ggggcgagcc gccgcccacc cggctctacg  42360
gcttggccga cctccccgag ctcgtcggcc gcttctcctc catggccgcc gccgaggtgg  42420
cgctgtccct ggaggacgag gtcgccggca ccctctcgcg ggaggccgag gacaccgcgt  42480
accgggtggt acttgaatcg ttgaccaatg tccgtcggca tgcgccgcag gccggccggg  42540
tccaggtgtt cgccggacgg accgccgacc gggccgtgga ggtctcggtc gccgacaacg  42600
cagggccggg ggcgtccgcc ggcacccggc agggcggcgg tacgggcctg gcgggcctcg  42660
gcgaacgcgt cagcgccctg ggcggctccc tggaggcggg cccgtacgag aacgggtggc  42720
gggtcaggtg cctgctgccg gcgcccgcca tccgctgagc ggatatctgc cgatcggcag  42780
atgtgccggc cgcccgggcc cgggatcctc ataggagtgc accaccccgt gactctggag  42840
gaaccgatgt tctcaggcac catctcgaag cggcccgcca cactcgtcgt cgcggtggcg  42900
gccgtcgccg ccaccctcgg cctctccggc tgctccgtgg acgcctcgaa ggcgaagccc  42960
gaatcgaagt cgttcacgta ctcgggcaag tccctgaagg tgacgacgca cgaggtcgcc  43020
accaaggtgg tcgccgccga ccgcaaggac atcaaggtca cccgctggtt cgactcggcc  43080
gcgggcaccg agcacctgaa gtggaccctc aagggcgaca ccctggacat cgacgccggc  43140
tgcagcggta tcgcgatctg cgacgccaag ttcaaggtcg aggtccccaa gggcatcgcg  43200
gtgaccaagg acggcgagaa gaccgacctg accgggaaga gctgaccgtg ctcgacctcg  43260
tcaacatcac caaggtctac aagggcggca agcacgccgt ggacgacctg acgatgcgtc  43320
tggaacccgg catgctcggc ctgctgggcc ccaacggcgc cggcaagtcg tccctcatgc  43380
ggatcgcctc cacggtcacc cggcccacca gcggaaaggt cctcttccac ggagaggacg  43440
cggtcgccaa gcccaacgcg ctgcgccggg ccctcggtta cctcccgcag gacttcggcg  43500
tctacccgaa cctgacctcc cgcgagttcc tcaggtatct ggcggcggcc aagggcgtct  43560
cggccaagac cgccaaggcc cgtatcgatg agctcctgga gctcgtcaac ctcaccgaag  43620
cggtcaagcg tcccctgggc aagtactccg gcggcatgct gcgccgggtc ggcatcgccc  43680
aggtgctgct cgccgacccg caggtgatca tcgtggacga gccgaccgcg gggctggacc  43740
ccgaggagcg ggtcaggttc cgcaatctgc tcagcgatct ggcggccgac aaggtcgtga  43800
tgctctccac ccacatcgtc tccgacgtcg agtcggtggc ctccgacatc gcggtgatgg  43860
ccggcggccg gctgcagcgc cgcggcaccc ccgaggacct gctgcgctcg gtggacggcc  43920
aggtgtggga ggtgctggtc gacccctcgt ccgtagcggc ggtgcaggcg cagtacaccg  43980
tcagccgcct ggtccgcacg accgagggcg tccgtatccg gctgctctcg cgcgagctgc  44040
```

-continued

```
cgtacgaggg cgccgtccag ctgacgcccg acctggaaga cgcctacctc gccatcatcc  44100
gtggggtcga cggcggccgg gccgcccagg gcttcggcga acggccgctc caggcacggg  44160
tggtgtgagg caatgatgcg catgctcacc ggtcttgcgg tggccgactt ccgcgaccgg  44220
gtacgccggc ccgcgtatgt cgtgatcctg gccgcggccg tcgccctcgg ttacgtggcg  44280
gtgcccgact cggacgccaa atggatgatc atgcagatcg gtgatcaccg cgggatctac  44340
aacagcgcct acgtcggcat ggtgacggcc ctggccagcg gtctgtggat caccctcggc  44400
ggcttctaca tcgtccgcaa ctccatcgaa cgcgaccgca gcacccgcgt cggccagctg  44460
ctcgccgcca ccccgctgcg caccaccgcg tacatgctcg gcaagttcct cagcaacctc  44520
atgctgctgt cctccatgct cgtggtgctc gcgctcaccg ccctggtcat gcaactggcc  44580
cgcggcgagt cgcacgacat cgacctgatc gccctctggc agcccttcct cctcatcgcg  44640
ctgccgctgg tcgcgctgac cgccgccctc gcgctcctct tcgaatcgct gccgctgctg  44700
cgcaccggcc tgggcaacat cctgtggttc tgcatctgga tggtcgtctc gacggccggc  44760
cagggccccg gtctgcccct cgacggcatc ggcgtcaaca gcgtcgtccg gtcgatgtat  44820
gacgacatgg tcgcccagca catcgatgtc accggcgcgt tcagcctcgg tctgacctac  44880
ctcgacaagc ccctcgggct cttcacctgg gacggcttca cgcccaccgc cggctatgtc  44940
ctcggccggg tgacgctgct gctgatcgcc gtcgtgatcg ccatgctccc cgcgctgtgg  45000
ttcggccgct tcgaccccgc gcgaacctgg ctgggccagg ggcgcacccc cgagcaggcc  45060
ccggccgacg gtgtcgtcca gccggtcttc atcgacgagg tcggcccggg gacgcctccg  45120
ctgtccgttc agggccatgg gggagcttcc ccgtcccggc ccaccgtcgc cacgctgctg  45180
cgcacccgcc cggagccggg cgccgtgacc ctgcgcgtct gggccggcga ggtccgcatc  45240
ctgctgcaag gtgtgcgctg gtggtggtgg accggtgccg cattcctcat gatcgccgcg  45300
ctctcctccc cggggatcca cggcatcatc cgcgtgatgc tgccgctgtc ctggatctgg  45360
ccggtgctga tctggtcgcg gctgggcacc cagcgccacg agtaccacgt cgacggcatg  45420
ctcggcgcct accccgcggt gcgccgccgg gtcttcgccg aatgggccgc gggcctgacc  45480
atcaccgccg tggccggcat cggtcccctg atccgcctgg tggccgccgc cgactggttc  45540
ggtctggccg gctgggtcgg cggggccctg ttcatcccgt ccctggccct caccctgggc  45600
acgctcagcc gtacccatcg cctcttccag gcggtctacc tgccgctctg gtacagcgtc  45660
gccaacggac tgccgatctt cgacttcatg ggcgcgctgc gcgacagcag cgaactggcc  45720
gccgtgcagc cgtcggtgac cgtcgtggtt tccgcggccc tgatggccat cgtcttcatg  45780
accggcgtac tccgccgctt cggccgcgac tgacccaccg accccgtcgg cgccgcggct  45840
gccgacgggt tcggggccgc gcggcaccgg tgcccccgag agaggaacac gccatgaccg  45900
accccatccg aacccccgac acgctcgccg tcgaccacac ccggcacaca cggccgctgc  45960
aggccgagcg ccggatcgcg gaactggaaa acgagttgga cgagctgcgc agcgccaacg  46020
agatcctctt atcggtggcc acctacttcg gccaggccaa cgtcctgccc acccggccgg  46080
ggatacccgg cccacccgcc gccgagcgct gacgcccgac gtaagcgccc cggcacacac  46140
aaagccaacg gggtgaagc accgactcga tccgaacaga cccgaggaac tcctatgcga  46200
ctgtggcccc ggcacaaagc cggccgaccc gaaaccgacc ggcacgaaac cgacccgcac  46260
acggccgagc agcacacggc cgacgcaccc gaggccggcc ggcccgcacc cggccgcacc  46320
acgaagggga gcccgcgctc gctccccgcg acgatcgtca tgacgctgtc cgtggccctg  46380
gccgtgaccc tgaccgcggc gctgaccggg gcgttcgccc ccgcccgccc gtccctcagg  46440
```

-continued agcgagaagg ccgcccccgc cgccccccac tccccccagt ggacagccac ctggggagcc 46500
gccatgcagc aggcgacgaa cgaggccacg gaggacaccc cgaactggtc ccggcaggga 46560
ttcaagaacg agaccctgcg ccaggtgatc cggctcagcg tcggcggccc cgagctccgt 46620
atccgcctct ccaacgccta cggcaccaag cccctccaca tcgccggcgc caccgtcgcc 46680
aggtccgacg gcgaggccaa ggcgcgcccc ggcaccgtac gcaccctcac cttccgccat 46740
gcgcccgccc tcaccatccc cgcgggccgc gacaccgtca gcgacgcggt ggccatgccg 46800
accgccaacc tcgaaaaact caccgtcacc ctgcgcttca ccgcccccac cggcccggcc 46860
accatgcacc gcttcaccac ggccacgtcc taccgcgccc ccggcgaccg gctacgcagc 46920
cccgccgccg atgacttcaa ccgccgtgcc tcgcacgcct ggtactacct gacggccgtc 46980
gatgtgaccc aggagccgcc ccgttcggcc gactccctca tggtcttcgg cgactccctc 47040
atggacggcg tcggcaccag ccccgacacc gacaaccgct tctccgacaa actcgccgaa 47100
cgcctcatcg ccgccggccg cccccaggga atgaccaacg ccggcctggc gggtgacccc 47160
ctgctgcacg attccccctg cttcggcgag aagggcaccg cccgcttcgc caaggaactg 47220
cgcgatcgcg ccgccctgcg caccgtcttc atccacctcg gcgccaatga cctcgcccag 47280
tcccagcagg acgacccctg caccaggaac cgcccccccgg tgaccgccca acagctcatc 47340
gacggccacc gcgccctggt ccgcgcggcc cacgcccgcg gtatcaaggc catcggtgtg 47400
acgatcctcc ccctcaggag cgccgtcttc cccttcacca cccccgccgg tgacaagatc 47460
cgccggcagc tcaaccactg gatccgcacc agccacacct acgacgccgt cctcgacgcc 47520
gaccgcgtcc tgaccgaccc cgcgaacccc aaccgccccc gccccggcta catctcccag 47580
gacggcctcc accccagcga cgccggctac ctggccctcg cctccgccgt cgacctgaac 47640
gccctctgac cccactcccc ccacccccag acagccccga ccaggtgccc cccgtccctg 47700
gtcggggcgc acgtccgtca cgagggcaac gtccgtctgt acgcgggcga gtgcggcccc 47760
gaggcagaag tgcgggccgt gtgcgaagtc ctggccggcc tcgccgagcg cacccccccag 47820 ccgccgcccc cggcgtccgg ccgcaccgcc caggaagccc tgggcgcgtt cgcccgcgca 47880
tgggtcgccc ggctcccgct cgccaccgat gagcaccggg cggccgggat cggcatggtc 47940
ctgatgccgg agatcctcgc cgacgcacga acccgcctgc cgttcgccca actgatgaag 48000
ctcaacgcga tcctgctcgg actcgccccg gagcgtctgc accggcccga agcctccgcc 48060
ccccgcctgg tacgcgtcgc ggaagccacc tcaccaccct gcacggcgcg agccaactgg 48120
ccgacgccgc acccggcttc accgaaccct tcgacatcgt cagcgcctgc gagcggctga 48180
ccggcctcga tctgggcgac 48200

<210> SEQ ID NO 2
<211> LENGTH: 2747
<212> TYPE: PRT
<213> ORGANISM: Streptomyces hygroscopicus

<400> SEQUENCE: 2

Met Gly Glu Trp Arg Asp Arg Arg Leu Asp Glu Leu Phe Ala Glu Gln
1 5 10 15

Ala Ala Arg Thr Pro Glu Arg Thr Ala Val Val Phe Glu Gly Arg Ala
20 25 30

Val Ser Tyr Arg Glu Leu Asp Ala Arg Ala Glu Arg Leu Ala Ala Val
35 40 45

Leu Ala Gly Arg Gly Ala Gly Pro Glu Arg Phe Ile Ala Leu Leu Leu

-continued

```
    50                  55                  60

Pro Arg Ser Ala Glu Leu Ile Val Ala Ile Leu Ala Val Leu Lys Ser
65                  70                  75                  80

Gly Ala Gly Tyr Ile Pro Ile Asp Pro Glu Tyr Pro Ala Asp Arg Ile
                85                  90                  95

Ala Tyr Ile Leu Gly Asp Ala Arg Pro Val Ala Thr Ile Thr Thr Ala
            100                 105                 110

Glu Val Arg Asp Gly Leu Pro Asp Pro Asp Thr Gly Ser Gly Thr Asp
        115                 120                 125

Trp Leu Ile Leu Asp Glu Ser Gly Tyr Glu Gln Glu Pro Ala Gly Ala
    130                 135                 140

Arg Pro Gln Pro Ala Pro Ala Ala Pro Arg Ser Ala Glu Asn Pro Ala
145                 150                 155                 160

Tyr Val Ile Tyr Thr Ser Gly Ser Thr Gly Arg Pro Lys Gly Val Val
                165                 170                 175

Ile Pro His Ser Asn Val Gly Arg Leu Leu Ser Ser Thr Ala His Trp
            180                 185                 190

Tyr Gly Phe Asp Glu Gln Asp Val Trp Pro Leu Phe His Ser Phe Ala
        195                 200                 205

Phe Asp Val Ser Val Trp Glu Ile Trp Gly Ala Leu Leu His Gly Gly
    210                 215                 220

Lys Leu Val Val Val Pro His Ala Val Thr Arg Ala Pro Ala Asp Phe
225                 230                 235                 240

Leu Arg Leu Leu Val Glu Glu Arg Val Thr Val Leu Asn Gln Thr Pro
                245                 250                 255

Ser Ala Phe Tyr Gln Leu Met Ala Ala Asp Arg Glu Asn Pro Ala Leu
            260                 265                 270

Gly Ala Gln Leu Ala Leu Arg Tyr Val Val Phe Ala Gly Glu Ala Leu
        275                 280                 285

Asp Leu Gly Lys Leu Ala Asp Trp Tyr Glu Arg His Asp Asp Arg Ala
    290                 295                 300

Pro Thr Leu Val Asn Met Tyr Gly Ile Thr Glu Thr Thr Val His Ser
305                 310                 315                 320

Ser Phe Leu Ala Leu Asp Lys Glu Gly Ala Ala Gly Ala Thr Gly Ser
                325                 330                 335

Ala Val Gly Val Ala Leu Pro Asp Leu Thr Phe His Val Leu Asp Glu
            340                 345                 350

Asp Leu Arg Pro Val Pro Val Gly Ala Glu Gly Glu Leu Tyr Val Ala
        355                 360                 365

Gly Pro Gly Leu Ala Arg Asn Tyr Ala Gly Arg Pro Gly Leu Thr Ala
    370                 375                 380

Glu Arg Phe Val Ala Cys Pro Phe Gly Pro Pro Gly Ala Arg Met Tyr
385                 390                 395                 400

Arg Ser Gly Asp Leu Val Arg Pro Leu Pro Asp Gly Gly Leu Glu Tyr
                405                 410                 415

Leu Arg Arg Ser Asp Asp Gln Val Lys Ile Arg Gly Phe Arg Ile Glu
            420                 425                 430

Leu Gly Glu Ile Ser His Ala Leu Ala Gln Asp Pro Ser Val Asp Gln
        435                 440                 445

Ala Thr Val Val Val Arg Asp Glu Ala Ser Gly Glu Arg Arg Leu Val
    450                 455                 460

Ala Tyr Val Val Pro Ala Gly Ser Ala Arg Pro Thr Pro Ser Arg Leu
465                 470                 475                 480
```

-continued

```
Arg Ala Ala Leu Ala Thr Arg Leu Pro Gly Tyr Met Val Pro Thr Ala
                485                 490                 495

Phe His Val Met Pro Ala Phe Pro Leu Thr Ala Asn Gly Lys Leu Asp
            500                 505                 510

Arg Arg Ala Leu Pro Ala Pro Thr Arg Gln Asp Ser Val Asp Ala Asp
        515                 520                 525

Tyr Ala Ala Pro Glu Gly Ala Thr Glu Glu Ala Leu Ala Ala Ile Trp
    530                 535                 540

Arg Glu Val Leu Gly Val Glu Gln Ile Gly Ala Asp Asp Asp Phe Phe
545                 550                 555                 560

Glu Leu Gly Gly Asp Ser Leu Ser Val Val Arg Ala Leu Ser Arg Met
                565                 570                 575

Arg Thr Gly Leu Gly Leu Arg Leu Thr Ala Ala Glu Phe Phe Ala Thr
            580                 585                 590

Pro Thr Val Arg Ala Leu Ala Ala Arg Arg Glu Arg Gly Thr Ile Gly
        595                 600                 605

Ala Pro Glu Gln Ile Pro Ala Ala Pro Arg Thr Gly Ala Leu Pro Leu
    610                 615                 620

Ser Phe Thr Gln Gln Arg Phe Trp Leu Phe His Glu Leu Asp Pro Gly
625                 630                 635                 640

Glu Val Glu Tyr Asn Val His Ser Ala Leu Arg Leu Arg Gly Thr Leu
                645                 650                 655

Asp Leu Pro Ala Leu Arg Thr Ala Leu Gly Gly Leu Ile Ala Arg His
            660                 665                 670

Glu Pro Leu Arg Thr Thr Val Val Ser Asp Asp Gly Arg Pro Thr Ala
        675                 680                 685

Val Ile Ala Pro Pro Glu Gly Phe Pro Val Pro Leu Thr Val Glu Asp
    690                 695                 700

Leu Ser Ala Leu Thr Gly Asp Asp Gln Glu Ala Ala Gln Arg Arg Leu
705                 710                 715                 720

Leu Ala Glu Glu Val Ala Arg Pro Phe Asp Leu Ala Ala Gly Pro Val
                725                 730                 735

Leu Arg Val Leu Val Ile Arg Arg Gly Glu Arg Asp His Ala Leu Val
            740                 745                 750

Ile Gly Val His His Leu Ala Thr Asp Gly Trp Ser Met Gly Leu Leu
        755                 760                 765

Thr Asp Glu Leu Ser Ala Arg Tyr Asp Ala Ala Arg Arg Gly Val Pro
    770                 775                 780

Ala Ala Leu Glu Pro Leu Pro Val His Tyr Ser Asp Tyr Ala Ala Trp
785                 790                 795                 800

Gln Arg Ala Thr Val Asp Asp Gly Arg Leu Val Pro Gln Ile Asp Tyr
                805                 810                 815

Trp Arg Asp Arg Leu Ala Asp Val Ala Pro Leu Gln Leu Pro Thr Asp
            820                 825                 830

Arg Pro Arg Pro Ala Leu Lys Thr Ser Ala Gly Ala Ala His Arg Phe
        835                 840                 845

Thr Leu Asp Arg Arg Leu Val Ala Ala Leu Lys Glu Leu Ser Ala Ala
    850                 855                 860

His Gly Ala Thr Leu Phe Met Thr Leu Thr Ala Ala Leu Gln Val Leu
865                 870                 875                 880

Leu Ala Arg Tyr Ser Gly Gln Gln Asp Ile Ala Leu Gly Thr Ala Val
                885                 890                 895
```

-continued

```
Ser Gly Arg Asp His Pro Gln Val Glu Arg Leu Val Gly Ala Phe Ile
            900                 905                 910

Asn Thr Val Val Leu Arg Ser Asp Val Arg Gly Glu Leu Pro Phe His
        915                 920                 925

Glu Phe Leu Gly Glu Val Arg Glu Thr Val Leu Gly Ala Phe Ala His
    930                 935                 940

Gln Asp Leu Pro Phe Asp Arg Leu Val Asp Ala Leu Gly Ala Glu Arg
945                 950                 955                 960

Asp Pro Ser Arg Thr Pro Leu Val Gln Ala Met Leu Leu Leu Gln Asn
                965                 970                 975

Ala Pro Ala Gly Ala Glu Glu Phe Ala Gly Leu Arg Thr Glu Thr Val
            980                 985                 990

Ala Leu Pro Arg Pro Ala Ala Ile  Phe Asp Leu Thr Val  Asp Cys Thr
        995                 1000                 1005

Glu Arg  Ala Gly Ala Leu Glu  Val Met Val Glu Tyr  Asn Thr Asp
    1010                 1015                 1020

Leu Phe  Asp Ala Thr Thr Ile  Glu Arg Leu Ser Gly  His Leu Arg
    1025                 1030                 1035

Val Leu  Leu Asp Ala Val Cys  Ala Ala Pro Arg Arg  Gln Val Arg
    1040                 1045                 1050

Asp Leu  Pro Leu Leu Pro Ala  Ala Glu Arg Asp Thr  Leu Leu Thr
    1055                 1060                 1065

Gly Trp  Asn Asp Thr Ala Ala  Ala Leu Pro Thr Thr  Leu Gly Val
    1070                 1075                 1080

His Arg  Gln Phe Ala Glu Arg  Ala Arg Thr Thr Pro  Asp Ala Leu
    1085                 1090                 1095

Ala Val  Thr His Cys Gly Gln  Thr Leu Thr Tyr Ala  Gln Leu Asp
    1100                 1105                 1110

Ala Arg  Ala Asn Gln Leu Ala  His Tyr Leu Gly Ala  Leu Gly Val
    1115                 1120                 1125

Gly Arg  Gly Thr Pro Val Val  Leu Asn Leu Ala Arg  Lys Pro Gln
    1130                 1135                 1140

Leu Ile  Val Ala Met Leu Ala  Val Leu Lys Ala Gly  Gly Ala Tyr
    1145                 1150                 1155

Val Pro  Thr Ala Leu Asp Thr  Pro Ala Ala Arg Leu  Gly His Leu
    1160                 1165                 1170

Leu Glu  Glu Thr Gly Thr Pro  Val Leu Leu Thr Thr  Ala Arg Gln
    1175                 1180                 1185

Ala Gly  Ala Leu Pro Pro Thr  Glu Ala Ser Val Ile  Asp Leu Asp
    1190                 1195                 1200

Ala Ala  Gly Pro Asp Ile Ala  Arg His Pro Glu His  Asp Pro Gln
    1205                 1210                 1215

Val Ala  Thr Arg Pro Glu Asp  Leu Ala Tyr Ile Val  Tyr Thr Ser
    1220                 1225                 1230

Gly Ser  Thr Gly Arg Pro Lys  Gly Val Ala Val Pro  His Ser Ala
    1235                 1240                 1245

Leu Thr  Asp Tyr Cys Ala Trp  His Asn Asp Ala Leu  Asp Val Gly
    1250                 1255                 1260

Pro Glu  Asp Arg Gly Ser Ser  Val Val Gly Leu Ala  Phe Asp Val
    1265                 1270                 1275

Ala Val  Gly Glu Val Trp Pro  Tyr Leu Cys Ala Gly  Ala Arg Val
    1280                 1285                 1290

Asp Gln  Pro Asp Gln Glu Thr  Leu Asp Asp Pro Thr  Ala Leu Val
```

-continued

```
    1295                1300                1305

Glu Trp  Phe Ala Glu Asn Gly  Thr Thr Val Ala Tyr  Leu Pro Thr
    1310                1315                1320

Pro Arg  Ile Glu Ser Leu Leu  Asp Val Ala Ala Ile  Thr Thr Thr
    1325                1330                1335

Arg Leu  Arg Thr Val Leu Val  Ile Gly Asp Ser Leu  Arg Arg Arg
    1340                1345                1350

Pro Gln  Pro Gly Leu Pro Phe  Thr Leu Leu Asn Ala  Tyr Gly Pro
    1355                1360                1365

Ala Glu  Ala Thr Val Ala Ala  Thr Gln Ala Val Val  Glu Pro Leu
    1370                1375                1380

Gly Pro  Asp Ala Pro Ala Gly  Leu Pro Ser Ile Gly  Ala Pro Leu
    1385                1390                1395

Tyr Asn  Thr Ala Ala Tyr Val  Leu Asp Asp Arg Leu  Cys Pro Val
    1400                1405                1410

Pro Val  Gly Val Pro Gly Glu  Leu Tyr Leu Ala Gly  Ala Gly Leu
    1415                1420                1425

Ala Gln  Gly Tyr Gln Gly Arg  Pro Asp Leu Thr Ala  Glu Arg Phe
    1430                1435                1440

Val Gly  Cys Pro Phe Gly Pro  Pro Gly Thr Arg Met  Tyr Arg Thr
    1445                1450                1455

Gly Asp  Ile Val Arg Trp Leu  Pro Asp Gly Thr Leu  Asp Phe Leu
    1460                1465                1470

Gly Arg  Ile Asp Asn Gln Val  Lys Leu Arg Gly Tyr  Arg Ile Glu
    1475                1480                1485

Leu Gly  Glu Ile Glu Ser Val  Leu Ala Arg Arg Glu  Glu Leu Ser
    1490                1495                1500

Gln Val  Phe Val Thr Val Arg  Glu Pro Ser Pro Gly  Arg Arg Ser
    1505                1510                1515

Leu Val  Ala Tyr Leu Val Ala  Asp Arg Gly Thr Ala  Pro Asp Pro
    1520                1525                1530

Glu Glu  Leu Ala Gly Tyr Ile  Ala Ser Val Leu Pro  Glu Tyr Met
    1535                1540                1545

Val Pro  Ser Ser Phe Val Leu  Leu Asp Ala Leu Pro  Leu Thr Ala
    1550                1555                1560

Asn Gly  Lys Ile Asp Arg Arg  Ala Leu Pro Glu Pro  Glu Pro Ala
    1565                1570                1575

Gly Gly  Glu Gly Ala Ala Tyr  Val Ala Pro Gly Asn  Glu Val Glu
    1580                1585                1590

Glu Thr  Leu Ala Ala Ile Trp  Ala Glu Val Leu Gly  Val Glu Arg
    1595                1600                1605

Val Gly  Val Gln Asp Asn Phe  Phe Ala Leu Gly Gly  Asp Ser Ile
    1610                1615                1620

Ser Gly  Leu Gln Thr Ala Val  Arg Ala Arg Arg Ala  Gly Leu Arg
    1625                1630                1635

Leu Ala  Ser Lys Asp Leu Phe  Gln Arg Gln Thr Ile  Ala Ala Leu
    1640                1645                1650

Ser Pro  Val Val Thr Val Glu  Arg Thr Thr Ala Asp  Ala Asp Pro
    1655                1660                1665

Ala Pro  Ser Asp Arg Pro Thr  Ala Pro Phe Ala Leu  Ser Gly Leu
    1670                1675                1680

Asp Arg  Val Gly Val Glu Arg  Leu Thr Ala Asp Gly  Gly Pro Ala
    1685                1690                1695
```

-continued

```
Glu Asp  Ala Tyr Pro Leu Thr  Pro Met Gln Ser Gly  Leu Leu Phe
    1700                 1705                 1710

His Thr  Leu Met His Ala Glu  Arg Gly Met Tyr Ile  Glu Gln Phe
    1715                 1720                 1725

His Phe  Ala Leu His Ser Ile  Arg Glu Pro Glu Leu  Leu Ala Thr
    1730                 1735                 1740

Ala Trp  Gln Arg Val Val Asp  Arg Thr Pro Val Leu  Arg Thr Ser
    1745                 1750                 1755

Leu Ala  Trp Asp Gly Leu Ala  Glu Pro Leu Gln Val  Val Arg Thr
    1760                 1765                 1770

Gly Val  Arg Ile Pro Val Ala  Gln Leu Asp Trp Thr  Ala Leu Asp
    1775                 1780                 1785

Glu Ala  Gly Gln Arg Gln Ala  Leu Glu Arg Tyr Leu  Thr Glu Asp
    1790                 1795                 1800

Arg Thr  Arg Gly Leu Asp Leu  His Thr Ala Pro Leu  Ala Arg Ile
    1805                 1810                 1815

Ala Val  Ala Arg Leu Gly Gly  Asp Gln Val Arg Leu  Val Trp Thr
    1820                 1825                 1830

Phe His  His Leu Leu Leu Asp  Gly Trp Ser Val Val  Gln Val Leu
    1835                 1840                 1845

Ser Glu  Val Leu Gly Glu Tyr  Ala Ala Leu Ala Asp  Gly Ile Pro
    1850                 1855                 1860

Tyr Thr  Pro Gln Leu Arg His  Thr Tyr Ala Glu Phe  Val Gly Gln
    1865                 1870                 1875

Leu Ala  Gly Gln Asp His Thr  Ala Ala Glu Lys Tyr  Trp Arg Ala
    1880                 1885                 1890

Ala Leu  Thr Gly Arg Glu Ser  Pro Thr Pro Leu Pro  Tyr Asp Arg
    1895                 1900                 1905

Pro Arg  Pro Asp Ala His Gln  Ala Ala Pro Asp Ala  Glu Leu Lys
    1910                 1915                 1920

Leu Arg  Leu Pro Ala Ala Val  Thr Gly Arg Leu Gly  Thr Ala Ala
    1925                 1930                 1935

Lys Arg  Ala Gly Val Thr Met  Asn Thr Val Val Gln  Gly Leu Trp
    1940                 1945                 1950

Ala Leu  Leu Leu Ala Arg His  Ser Gly Glu Arg Asp  Val Leu Phe
    1955                 1960                 1965

Gly Ala  Thr Val Ala Gly Arg  Pro Asp Asp Leu Ala  Gly Ala Glu
    1970                 1975                 1980

Ser Val  Ile Gly Leu Phe Ile  Asn Thr Leu Pro Val  Arg Val Asp
    1985                 1990                 1995

Val Asp  Pro Asp Ala Gly Leu  Leu Ser Trp Leu Arg  Arg Val Gln
    2000                 2005                 2010

Asp Glu  Gln Ala Glu Ala Arg  Ala His Glu Gln Val  Ser Leu Ala
    2015                 2020                 2025

Gln Val  Gln Gly Trp Ala Pro  Glu Arg Ala His Gly  Gly Leu Phe
    2030                 2035                 2040

Asp Ser  Val Leu Ala Phe Glu  Asn Phe Pro Ala Asp  Leu Gly Pro
    2045                 2050                 2055

Ala Gly  Asn Tyr Gly Leu Arg  Leu Asp Ala Ile Glu  Ala Ser Asn
    2060                 2065                 2070

Thr Ser  Asn Tyr Pro Leu Asn  Ala Ile Val Gln Leu  Asn Glu Glu
    2075                 2080                 2085
```

-continued

```
Leu Thr  Val Leu Leu Arg Tyr  Asp Thr Ala Leu Phe  Asp Ala Asp
    2090                 2095                 2100

Thr Val  Ala Arg Leu Ala Gly  His Leu His Thr Leu  Leu Glu Glu
    2105                 2110                 2115

Thr Ala  Glu Asn Pro Asp Arg  Arg Val Gly Glu Leu  Pro Leu Leu
    2120                 2125                 2130

Thr Ala  Ala Glu Arg His Thr  Ile Val His Thr Trp  Thr Asp Thr
    2135                 2140                 2145

Ala Ser  Asp Tyr Ser Val Asp  Arg Arg Leu Asp Ala  Val Ile Ala
    2150                 2155                 2160

Glu Gln  Ala Ala Ala Arg Pro  Thr Ala Ile Ala Val  Val Asp Gly
    2165                 2170                 2175

Glu Arg  Gln Leu Ser Tyr Gly  Glu Leu Asp Arg Arg  Ala Asn Gln
    2180                 2185                 2190

Leu Ala  His His Leu Arg Ala  Ala Gly Val Gly Arg  Asp Ala Leu
    2195                 2200                 2205

Val Gly  Ile Ala Val Glu Arg  Ser Ala Glu Val Val  Val Ala Ile
    2210                 2215                 2220

Leu Gly  Thr Leu Lys Ala Gly  Ala Ala Tyr Val Pro  Leu Asp Pro
    2225                 2230                 2235

Glu Phe  Pro Ala Gln Arg Leu  Ala Thr Met Leu Ser  Glu Ser Arg
    2240                 2245                 2250

Pro Ala  Val Leu Leu Thr Gln  Glu His Leu Leu Ala  Gly Leu Pro
    2255                 2260                 2265

Pro Thr  Asp Ala Arg Val Val  Cys Val Asp Arg Asp  Leu Ala Ala
    2270                 2275                 2280

Ile Glu  Ala His Pro Thr Ala  Ala Pro Val Ser Gly  Gly Asp Ala
    2285                 2290                 2295

Gly Asp  Leu Ala Tyr Val Thr  Tyr Thr Ser Gly Ser  Thr Gly Arg
    2300                 2305                 2310

Pro Lys  Gly Val Met Val Glu  His Arg Ser Leu Phe  Asn Ile Ile
    2315                 2320                 2325

Thr Glu  Ala Gly Arg Leu Tyr  Asp Leu Gly Pro Asp  Ser Arg Met
    2330                 2335                 2340

Leu Gln  Phe Tyr Thr Met Ser  Phe Asp Gly Gly Val  Trp Glu Val
    2345                 2350                 2355

Phe Leu  Thr Leu Thr Ala Gly  Ala Thr Leu Val Ile  Ala Asp Pro
    2360                 2365                 2370

Glu Ala  Arg Gln Ser Pro Ala  His Leu Ala Glu Gln  Leu Arg Ala
    2375                 2380                 2385

Glu Ser  Ile Thr Ala Leu Thr  Leu Pro Pro Ala Val  Ala Ser Val
    2390                 2395                 2400

Leu Asp  Ala Ala Ser Leu Pro  Gly Ile Arg Ser Leu  Gly Leu Ala
    2405                 2410                 2415

Gly Asp  Val Leu Ala Pro Glu  Leu Ala Arg Glu Trp  Ala Arg Gly
    2420                 2425                 2430

Arg Arg  Leu Phe Asn Ile Tyr  Gly Pro Ser Glu Ala  Thr Leu Ser
    2435                 2440                 2445

Val Ala  Leu His Arg Val Asp  Pro Gly Ala Ala Gly  Arg Gln Val
    2450                 2455                 2460

Pro Leu  Gly Pro Pro Val Pro  Asn Thr Arg Phe His  Val Leu Asp
    2465                 2470                 2475

Glu Arg  Leu Ala Val Val Pro  Val Gly Val Thr Gly  Glu Leu Tyr
```

-continued

```
    2480                2485                2490

Ile Gly  Gly Ala Gly Leu Ala  Arg Gly Tyr Leu Gly  Arg Pro Asp
    2495                2500                2505

Leu Thr  Ala Gln Arg Phe Val  Ala Asp Pro Phe Gly  Pro Pro Gly
    2510                2515                2520

Ser Arg  Leu Tyr Arg Thr Gly  Asp Leu Ile Arg Trp  Thr Pro Gln
    2525                2530                2535

Gly Arg  Leu Glu Phe Ala Gly  Arg Val Asp Asn Gln  Val Lys Ile
    2540                2545                2550

Arg Gly  Tyr Arg Val Glu Pro  Ala Glu Val Glu Ser  Ala Leu Leu
    2555                2560                2565

Arg Gln  Pro Gly Val Ala Glu  Ala Val Val Ile Ala  Arg Asp Asp
    2570                2575                2580

Asp Thr  Gly His Lys Arg Leu  Val Ala Tyr Val Val  Pro Asp Gly
    2585                2590                2595

Ser Gly  Thr Ala Pro Glu Arg  Ala Ala Leu Leu Arg  Ala Leu Gly
    2600                2605                2610

Gly Gln  Leu Pro Gly Tyr Met  Val Pro Ser Ala Leu  Val Thr Leu
    2615                2620                2625

Pro Glu  Leu Pro Leu Gly Pro  Thr Gly Lys Val Asp  Val Arg Ala
    2630                2635                2640

Leu Pro  Ala Pro Asp Pro Ala  Ala Gly Gly Thr Ala  Asp Arg Ile
    2645                2650                2655

Pro Pro  Arg Thr Pro Thr Glu  Glu Ala Leu Ala Leu  Ile Trp Val
    2660                2665                2670

Glu Leu  Leu Gly Leu Glu His  Val Gly Val Glu Asp  Asn Phe Phe
    2675                2680                2685

Asp Leu  Gly Gly Asp Ser Ile  Thr Ser Leu Arg Leu  Met Ser Arg
    2690                2695                2700

Met Gly  Gly Ala Phe Gly Val  Asp Val Ser Pro Arg  Asp Phe Phe
    2705                2710                2715

Asp Ala  Pro Thr Ile Ala Ala  Leu Ala Glu Arg Leu  Glu Glu Lys
    2720                2725                2730

Ile Leu  Ala Gln Leu Glu Glu  Ala Val Gly Gly Gly  Ala Leu
    2735                2740                2745
```

<210> SEQ ID NO 3
<211> LENGTH: 8244
<212> TYPE: DNA
<213> ORGANISM: Streptomyces hygroscopicus

<400> SEQUENCE: 3

```
atgggtgagt ggcgcgatcg ccgcctggac gaattgttcg ccgagcaggc cgcgagaaca     60

ccggagcgta ccgcggtggt cttcgagggc cgggcggtga gttatcggga actcgacgcc    120

cgcgccgagc ggctggccgc tgtgctggcc ggccgcggcg cgggacccga gcggttcatc    180

gcgctgctgc tgccccgctc cgccgaactg atcgtggcca tcctcgccgt actgaagtcc    240

ggcgccggat acatcccgat cgacccggag tacccggccg accgcatcgc ctacatcctc    300

ggcgacgcgc gcccggtggc gacgatcacc accgccgagg tgcgggacgg tctgccggac    360

ccggacaccg gctccgggac cgactggctg atcctggacg agtccgggta cgagcaggag    420

ccggccgggg cgcgcccgca gcccgccccg gccgccccgc ggtccgcgga gaaccccgcc    480

tacgtcatct acacctccgg ctcgaccggc cggcccaagg gcgtggtgat cccgcacagc    540
```

-continued

```
aatgtgggac ggctgctgtc gtccaccgcc cactggtacg gcttcgacga gcaggacgtc    600
tggccgctgt tccactcctt cgccttcgat gtctcggtct gggagatctg ggcgcgcgctg    660
ctgcacggcg gcaagctggt cgtcgtcccg catgccgtca cccgcgcccc ggccgacttc    720
ctgcggctgc tggtcgagga acgggtcacc gtcctgaacc agacgccttc ggcgttctac    780
cagctgatgg ccgccgaccg ggagaacccc gcgctcggcg cccaactcgc cctgcgttat    840
gtggtgttcg cgggtgaggc gctggacctg ggcaagctcg ccgactggta cgagcggcac    900
gatgaccggg cgccgacgct ggtcaacatg tacggcatca ccgagaccac cgtgcactcc    960
tcgttcctcg cactggacaa ggagggcgcg gccggcgcca cgggcagcgc cgtcggcgtc   1020
gccctccccg acctgacctt ccatgtcctc gacgaggacc tgcggcccgt cccggtcggc   1080
gcggagggcg agctgtatgt ggccgggccc gggctggcac ggaactacgc gggccggccg   1140
gggctgaccg cggagcgctt cgtggcctgc ccgttcggcc cgcccggggc ccgtatgtac   1200
cgctcgggcg acctggtgcg gccgctgccg gacggcggcc tcgaatacct gcggcgcagc   1260
gacgaccagg tcaagatccg cggtttccgg atcgaactgg gtgagatctc gcacgcactg   1320
gcccaggacc cctcggtcga ccaggccacg gtggtggtcc gcgacgaggc gtcgggcgag   1380
cgcaggctgg tggcgtacgt cgttccggcc ggctccgccc gtcccacccc gtcccggctg   1440
cgtgccgcgc tggccacccg cctgcccggc tacatggtcc ccaccgcctt ccacgtcatg   1500
ccggccttcc cgctgaccgc caacggcaag ctggaccgca gggcgctgcc cgcgcccacc   1560
cgccaggaca gcgtcgacgc cgactacgcc gcccccgagg gcgccaccga ggaggcgctg   1620
gccgccatct ggcgcgaggt gctcggcgtc gaacagatcg gtgccgacga cgacttcttc   1680
gagctcggcg gtgactcgct gtccgtggtg cgggcgctgt cgcggatgcg gaccggcctg   1740
gggctgcgcc tgacggccgc ggagttcttc gccaccccca ccgtccgggc actggccgcg   1800
cgccgcgagc ggggcacgat cggcgcgccg gagcagatac cggccgcgcc gcgtaccggc   1860
gcgctgccgc tgtccttcac ccagcagcgg ttctggctct tccacgaact cgaccccggc   1920
gaggtcgagt acaacgtcca ctccgcgctg cggctgcgcg gcaccctcga cctccccgcg   1980
ctgcgcaccg cgctcggcgg gctgatcgcc cgccatgagc cgctgcggac gaccgtggtc   2040
tccgacgacg gccgccccac cgcggtcatc gccccgcccg agggcttccc ggtcccgctc   2100
accgtcgagg atctctccgc gctgaccggc gacgaccagg aggccgccca gcggcgactg   2160
ctggccgagg aggtcgcccg gcccttcgac ctggccgccg gcccggtgct gcgggtgctg   2220
gtgatccgcc gcggcgagcg cgatcacgcc ctggtgatcg gggtgcatca cctcgccacc   2280
gacggctggt cgatggggct gctcaccgac gagctgagcg cgcgctacga cgccgcgcgc   2340
cgcggggtgc ccgccgcgct ggagccgctg ccggtccact acagcgacta cgccgcctgg   2400
cagcgcgcca ccgtggacga cggccggctg gtgccccaga tcgactactg gcgcgaccgg   2460
ctggcggatg tggcaccgct gcaactgccc accgaccggc cccggcccgc gctgaagacc   2520
tcggccggtg cggcgcaccg cttcaccctc gaccgccggc tggtcgccgc cctcaaggag   2580
ctgagcgccg cccatggcgc cacgctcttc atgaccctga ccgccgcgtt gcaggtgctg   2640
ctcgcccgct actccggaca gcaggacatc gcgctgggca ccgccgtctc cggccgggac   2700
cacccgcagg tggagcggct ggtcggcgcg ttcatcaaca ccgtggtgct ccgctccgac   2760
gtgcgcggcg agctgccctt ccacgaattc ctcggggagg tacgggagac ggtgctgggc   2820
gccttcgcgc accaggacct tccgttcgac cggctcgtgg acgcgctggg cgccgagcgc   2880
gacccgagcc gtaccccgct ggtccaggcg atgctgctgc tgcagaacgc cccggccggt   2940
```

-continued gcggaggagt tcgccgggct gcgcaccgag accgtcgcgc tgccgcgccc ggccgcgatc 3000
ttcgacctga cggtggactg cacggagcgg gccggggcgc tggaggtgat ggtcgagtac 3060
aacaccgatc tgttcgacgc gacgaccatc gagcggctct cgggccatct gcgggtgctg 3120
ctggacgccg tatgcgcggc accgcggcgc caggtgcgcg atctgccgct gctgccggcg 3180
gccgaacgcg acacgctgct gaccggctgg aacgacaccg ccgccgcact gccgacgacg 3240
ctcggggtgc accgccagtt cgccgagcgg gcccgcacca ccccggacgc gctcgccgtc 3300
acacactgcg gacagaccct cacctacgcc caactcgacg cgcgcgccaa ccagttggcg 3360
cactacctgg gcgctctcgg cgtcggccgg ggcacccccg tggtgctgaa cctggcgcgc 3420
aagccgcagc tgatcgtggc gatgctcgcg gtgctcaagg ccggcggcgc gtacgtaccg 3480
accgcgctgg acaccccggc ggcacggctc gggcatctcc tggaggagac cggcaccccc 3540
gtgctgctga ccaccgcgcg gcaggccgga gcgctgcccc cgaccgaggc gagcgtcatc 3600
gacctcgacg cggccgggcc ggacatcgcc cggcatccgg agcacgaccc ccaggtggcg 3660
acccggcccg aggacctcgc gtacatcgtc tacacctccg ggtccaccgg ccgccccaag 3720
ggcgtcgcgg tgccgcacag cgcgctgacc gactactgcg cctggcacaa cgacgcgctg 3780
gacgtcggcc ccgaggaccg cgggtcgtcc gtggtcggcc tggccttcga cgtcgcggtc 3840
ggcgaggtgt ggccgtatct gtgcgcgggc gcccgcgtgg accagcccga ccaggagacg 3900
ctggacgatc cgacggcgct ggtggagtgg ttcgccgaga acggcaccac ggtcgcctat 3960
ctgccgaccc cgcgcatcga atccctgctg gacgtagcgg cgatcaccac cacccggctg 4020
cgcaccgtcc tggtcatcgg cgactcgctg cgccgcaggc cgcagcccgg actgccgttc 4080
accctgctca acgcctacgg gcccgcggag gcgacggtgg ccgccaccca ggcggtggtc 4140
gagcccctgg gacccgacgc gcccgccggg ctgccgtcca tcggcgcccc gctgtacaac 4200
accgccgcct atgtcctcga cgaccggctg tgcccggtcc ccgtcggggt gcccggcgag 4260
ctgtacctcg ccggcgcggg tctggcgcag ggctatcagg gccgccccga cctgaccgcg 4320
gagcgcttcg tcggctgccc cttcgggccg cccggaaccc ggatgtaccg cacgggtgac 4380
atcgtgcgat ggctaccgga cggcaccctg gacttcctcg gccggatcga caaccaggtc 4440
aaactgcgcg gctaccgcat cgaactcggc gagatcgaga gcgtgctggc ccgccgcgag 4500
gagctctcgc aggtgttcgt cacggtccgc gagccgtccc ccggccgccg gtccctggtc 4560
gcctacctcg tcgccgaccg gggcaccgcg cccgacccgg aggagctcgc cggatacatc 4620
gcctccgtac tcccggagta catggttccg tcctccttcg tactgctcga cgcgctgccg 4680
ctgaccgcga acggcaagat cgaccggcgg gcgctgcccg agccggagcc ggccggcggc 4740
gagggcgccg cgtatgtcgc gcccggcaac gaggtcgagg agaccctggc cgccatctgg 4800
gccgaggtgc tcggcgtcga acgggtcggc gtgcaggaca acttcttcgc cctcggcggc 4860
gactcgatca gcggtctgca gaccgccgta cgggcccgcc gggccgggct gcgactggcc 4920
tccaaggacc tcttccagcg ccagaccatc gcggcgctga gccccgtggt gacggtggag 4980
cggaccacgg cggacgccga ccccgcaccg tccgaccggc cgaccgcgcc gttcgcgctc 5040
agcggtctgg accgggtcgg tgtggagcgg ctgaccgcgg acggcggccc ggccgaggac 5100
gcctacccgc tgaccccgat gcagagcggg ctgctcttcc acaccctgat gcacgccgaa 5160
cgcggcatgt acatcgagca gttccacttc gccctgcaca gcatccgcga gccggagctg 5220
ctggccaccg cctggcagcg ggtcgtcgac cgcacccctg tgctccgtac gtcactggcc 5280

-continued

```
tgggacggcc tcgccgaacc gctccaggtc gtgcgcaccg gcgtccggat accggtggca   5340
cagctcgact ggacggcact ggacgaggcc ggacagcggc aggccctgga gcggtatctg   5400
accgaggacc gcacgcgcgg gctcgatctg cacaccgcgc cactcgcccg gatcgccgtc   5460
gcccgcctgg gcggcgacca ggtccggctg gtgtggacgt tccaccatct gctgctggac   5520
ggctggagcg tcgtacaggt gctgtccgag gtgctcggcg agtacgccgc gctcgccgac   5580
ggcatcccgt acaccccgca actgcggcac acctacgccg agttcgtcgg ccagctggcg   5640
gggcaggacc acaccgccgc cgagaagtac tggcgtgccg cgctcaccgg ccgtgagtcg   5700
cccaccccgc tgccgtacga ccggccgcgc cccgacgccc atcaggccgc ccccgacgcc   5760
gagctgaagc tgcggctgcc ggccgcggtg accggccgac tgggcaccgc ggcgaagcgg   5820
gccggggtga cgatgaacac cgtggtgcag ggcttgtggg cgctgctgct ggcccgccac   5880
agcggtgagc gggacgtact gttcggcgcc acggtcgccg gccggcccga cgatctggcg   5940
ggcgcggaat cggtgatcgg cctgttcatc aacacccttc cggtgcgcgt cgacgtcgat   6000
ccggacgccg gtctgctgag ctggctgcgc cgggtgcagg acgagcaggc cgaggcgcgc   6060
gcccatgagc aggtctcgct cgcccaggtg cagggctggg cgccggagcg ggcgcacggc   6120
ggactgttcg acagcgtgct ggccttcgag aacttcccgg ccgacctcgg tcccgccggg   6180
aactacgggc tgcggctcga cgccatcgag gccagcaaca cctccaacta cccgctcaac   6240
gccatcgttc agctcaacga agagctgacc gtgctgctgc gctacgacac cgcgctgttc   6300
gacgcggaca ccgtggcgcg gctggccggc catctgcaca cgctgctgga ggagaccgcc   6360
gagaaccccg accgccgggt cggcgagctg cccctgctca ccgccgccga gcggcacacc   6420
atcgtgcaca cctggaccga caccgcctcg gactactcgg tcgaccgccg gctggacgcg   6480
gtcatcgccg aacaggccgc ggcccggccg accgcgatcg ccgtcgtcga cggtgaacgg   6540
cagctgagtt acggcgagtt ggaccgccgc gccaaccagc tggcacacca tctgcgcgcc   6600
gcgggcgtgg gccgggacgc cctcgtcggg atcgccgtcg agcgcagcgc ggaggtcgtc   6660
gtggccatcc tcggcacgct caaggcgggc gccgcgtatg tgccgctcga ccccgaattc   6720
cccgcgcagc ggctcgccac catgctgtcc gagtcccggc ccgcggtcct gctcacccag   6780
gaacacctgc tggcggggct gccgccgacg gacgcccggg tggtgtgcgt ggaccgggac   6840
ctggcggcca tcgaggcgca ccccaccgcc gcgccggtct ccggcggcga cgccggcgac   6900
ctggcctatg tcacctacac ctcgggctcc accggccgcc ccaagggcgt catggtcgag   6960
caccgctcgc tgttcaacat catcaccgag gccggacggc tctacgacct gggccccgac   7020
agccggatgc tgcagttcta cacaatgagc ttcgacggcg gcgtctggga ggtcttcctg   7080
acgctgaccg ccggcgccac cctcgtcatc gcggaccccg aggcccgcca gagcccggcc   7140
cacctcgccg agcagctgcg cgcggagtcg atcaccgcgc tgacgctgcc gcccgcggtg   7200
gcctcggtgc tggacgcggc ctcgctgccc ggcatacgca gcctggggct cgccggggat   7260
gtgctcgcgc ccgaactcgc ccgggagtgg gcgcgggggc gccggctgtt caacatctac   7320
gggcccagcg aggcgaccct gtccgtcgcc ctgcaccgcg tcgaccccgg ggccgccggg   7380
cgccaggtgc cgctcggacc gccggtgccc aacacccgtt tccatgtgct cgacgagcgg   7440
ctggccgtgg tcccggtcgg ggtgaccggc gagctctaca tcggcggtgc gggcctggcc   7500
cgcggctacc tgggccgccc cgacctgacc gcgcagcgct tcgtcgccga cccgttcgga   7560
ccgccgggat cccgtctcta ccgcaccggt gacctgatcc gctggacccc gcaggggcgg   7620
ctggagttcg ccgggcgggt ggacaaccag gtcaagatcc gcggctaccg tgtcgagccc   7680
```

-continued

```
gccgaggtgg agagcgcact gctgcggcag cccggcgtcg cggaggcggt ggtgatcgcc   7740

cgggacgacg acaccggcca caagcggctg gtcgcctatg tcgtaccgga cgggagcgga   7800

accgccccgg aacgcgccgc cctgctgcgc gccctgggcg gccaactccc cggctacatg   7860

gtgccgtcgg ccctcgtcac cctgcccgag ctaccgctcg gaccgaccgg caaggtcgat   7920

gtgcgggcgc tgccggcacc ggatccggcc gccggcggca ccgccgaccg catcccgccc   7980

cgcacccca cggaagaggc actggccctc atctgggtgg agctgctcgg gctcgaacac   8040

gtcggcgtcg aggacaactt cttcgacctc ggcggcgact ccatcaccag cctgcggttg   8100

atgtcgcgga tgggcggcgc gttcggtgtg gacgtctcac cccgcgactt cttcgacgcc   8160

cccaccatcg ccgcccttgc cgagcgccta gaggaaaaga tcctggcgca gttggaagaa   8220

gccgtcggag gcggcgccct atga                                          8244
```

<210> SEQ ID NO 4
<211> LENGTH: 3668
<212> TYPE: PRT
<213> ORGANISM: Streptomyces hygroscopicus

<400> SEQUENCE: 4

```
Met Thr Ser Ser Ala Ala Asp Gln Pro Asp Asn Pro Asn Thr Thr Thr
1               5                   10                  15

Pro Ala Ser Arg Ala Glu Arg Thr Ala Ala Leu Pro Ala His Val Gln
            20                  25                  30

Glu Leu Leu Arg Ala Arg Leu Ala Gly Arg Ala Ala Ala Thr Gly Gly
        35                  40                  45

Ala Asp Thr Ile Pro Arg Ile Gly His Asp Gly Pro Val Ala Leu Ser
    50                  55                  60

Pro Ala Gln Glu Arg Leu Trp Tyr Leu His Glu Leu Glu Pro Glu Ser
65                  70                  75                  80

Asn Glu Tyr Asn Thr Leu Arg Val Leu Arg Leu Arg Gly Asp Leu Asp
                85                  90                  95

Pro Gly Ala Leu Ser Ala Ala Leu Ser Glu Ile Val Ala Arg His Gly
            100                 105                 110

Ala Leu Arg Thr Thr Phe Gly Ser Arg Glu Gly His Ala Glu Gln Thr
        115                 120                 125

Val His Pro Pro Val Pro Thr Pro Leu Pro Leu Val Asp Leu Ser Ala
    130                 135                 140

Ala Asp Asp Gly Glu Arg Asp Asp Ala Leu Arg Thr Leu Leu Gln Tyr
145                 150                 155                 160

Glu Ala Arg Arg Pro Phe Asp Leu Arg Arg Gly Pro Val Leu Arg Ala
                165                 170                 175

Gln Leu Ile Arg Leu Ala Ala Asp Asp His Val Leu Ala Leu Ala Leu
            180                 185                 190

His His Ile Val Thr Asp Gly Trp Ser Met Gly Val Leu Thr Gly Glu
        195                 200                 205

Leu Thr Ala His Tyr Ala Ala Thr Leu Arg Gly Ala Pro Ala Val Leu
    210                 215                 220

Pro Glu Leu Pro Val Ser Tyr Leu Asp Val Ala Val Trp Gln Arg Asp
225                 230                 235                 240

Gln Leu Ser Ser Ala Arg Leu Arg Glu Gly Leu Asp His Trp Arg Arg
                245                 250                 255

Glu Leu Ala Gly Leu Val Pro Leu Asp Leu Pro Thr Thr Trp Gln Arg
            260                 265                 270
```

-continued

```
Pro Pro Val Arg Thr Ser Ala Gly Ala Leu His Ser Phe Glu Ile Pro
        275                 280                 285

Pro Ala Val Ala Ala Arg Leu Arg Glu Leu Gly Arg Glu Gln Gly Ala
    290                 295                 300

Thr Leu Phe Met Ala Leu Val Ala Ala Val Gln Leu Leu Leu Ser Arg
305                 310                 315                 320

Trp Ser Gly Gln Arg Asp Ile Ala Val Gly Thr Ala Ala Ala Gly Arg
                325                 330                 335

Gly Arg Thr Glu Thr Glu Asn Leu Ile Gly Phe Phe Val Asn Asn Leu
            340                 345                 350

Val Leu Arg Ser Arg Ile Asp Glu Thr Arg Ser Phe Thr Glu Leu Leu
        355                 360                 365

Arg Ala Val Arg Ala Thr Val Leu Asp Ala Phe Ala His Glu Asp Val
    370                 375                 380

Pro Phe Gln Arg Val Val Glu Ala Leu His Pro Glu Arg Asp Leu Ser
385                 390                 395                 400

Arg Pro Pro Leu Ala Glu Val Ala Val Asn Leu His Asn Thr Pro Arg
                405                 410                 415

Thr Asp Thr Glu Leu Pro Gly Leu Arg Ile Glu Glu Met Pro Pro Pro
            420                 425                 430

Val Phe Ala Ser Ser Met Asp Leu Ser Phe Asp Phe Thr Glu Arg Asp
        435                 440                 445

Asp Arg Leu Glu Gly His Leu Thr Tyr Asn Thr Asp Leu Phe Ala Ala
    450                 455                 460

Asp Ala Ala Ala Arg Met Ala Ala Gln Leu Val Thr Leu Leu Glu Asp
465                 470                 475                 480

Leu Thr Arg Arg Pro Ala Val Pro Val Ala Gly Leu Ala Val Leu Pro
                485                 490                 495

Ala Ala Glu His Arg Arg Val Thr Glu Glu Trp Pro His Ser Gly Pro
            500                 505                 510

Gly Arg Glu Pro Arg Thr Ala Pro Glu Leu Phe Ala Ala Gln Val Ala
        515                 520                 525

Arg Thr Pro Asp Ala Asp Ala Leu Val Ser Asp Glu Glu Thr Leu Ser
    530                 535                 540

Tyr Ala Glu Leu Asp Gly Arg Ile Asn Gln Trp Ala Arg Leu Leu Leu
545                 550                 555                 560

Ala Arg Gly Ala Gly Pro Glu Thr Leu Val Ala Val Ala Leu Pro Arg
                565                 570                 575

Ser Ala Gln Met Val Thr Ala Ile Leu Ala Ile Gln Lys Thr Gly Ala
            580                 585                 590

Ala Tyr Leu Pro Leu Asp Pro Lys Ser Pro Ala Glu Arg Asn Arg Leu
        595                 600                 605

Met Ile Glu Asp Ala Arg Pro Leu Leu Val Leu Thr Ser Ala Gly Phe
    610                 615                 620

Gly Asp Gly Ala Glu Leu Gly Ala Pro Ala Leu Phe Leu Asp Asp Pro
625                 630                 635                 640

Asp Thr Arg Ala Ala Ala Gly Glu Leu Ser Ala Gly Pro Leu Ala Ala
                645                 650                 655

Ala Glu Leu Pro Ala Pro Leu Leu Pro Gly His Pro Ala Tyr Val Ile
            660                 665                 670

Tyr Thr Ser Gly Ser Thr Gly Arg Pro Lys Gly Val Val Val Thr His
        675                 680                 685
```

-continued

```
Thr Gly Val His Gly Leu Val Ala Ala Gln Ser Ala His Phe Arg Thr
    690                 695                 700

Gly His Gly Ala Arg Val Leu Ser Phe Ala Ser Leu Gly Phe Asp Ala
705                 710                 715                 720

Ala Phe Ser Glu Leu Gly Met Ala Leu Leu Ser Gly Gly Ala Leu Val
                725                 730                 735

Val Val Asp Gln Glu Arg Ile Leu Pro Gly Gln Pro Leu Ala Asp Val
            740                 745                 750

Leu Ala Glu His Arg Val Thr His Val Thr Leu Pro Pro Ser Ala Leu
        755                 760                 765

Ser Ala Leu Thr Pro Gly Thr Leu Pro Lys Asp Leu Thr Leu Val Val
    770                 775                 780

Ala Gly Glu Ala Cys Pro Pro Ala Val Ala Arg Thr Trp Ser Ala His
785                 790                 795                 800

His Arg Met Ile Asn Ala Tyr Gly Pro Thr Glu Ser Thr Val Cys Ala
                805                 810                 815

Ser Met Ser Ala Ala Leu Thr Pro Asp Thr Val Ser Gly Asp Ser Val
            820                 825                 830

Pro Ile Gly Arg Pro Leu Ser Gly Val Arg Val Ser Val Leu Asp Asp
        835                 840                 845

Arg Leu Arg Pro Val Pro Ala Gly Val Pro Gly Glu Val Tyr Leu Ser
    850                 855                 860

Gly Ala Ala Leu Ala Arg Gly Tyr Leu Gly Arg Leu Ala Leu Thr Ala
865                 870                 875                 880

Glu Arg Phe Val Ala Asp Pro Tyr Gly Pro Pro Gly Ser Arg Met Tyr
                885                 890                 895

Arg Thr Gly Asp Arg Ala Arg Trp Leu Ala Gly Gly Asp Leu Asp Tyr
            900                 905                 910

Leu Gly Arg Thr Asp Asp Gln Val Lys Leu Arg Gly Phe Arg Ile Glu
        915                 920                 925

Leu Gly Glu Val Glu Ala Val Leu Ser Arg His Asp Gly Val Gly Ala
    930                 935                 940

Val Ala Ala Thr Val His Lys Asp Glu Arg Gly Thr Arg Arg Leu Val
945                 950                 955                 960

Ala Tyr Val Val Pro Ala Arg Glu Asp Ala Ala Asp Pro Ala Arg Leu
                965                 970                 975

Arg Glu Phe Ala Arg Glu Val Leu Pro Glu His Met Val Pro Ser Val
            980                 985                 990

Phe Val Pro Leu Asp Arg Leu Pro  Leu Asn Ala Asn Gly  Lys Val Asp
        995                 1000                1005

Arg Arg  Ala Leu Pro Ala Pro  Asp Ile Arg Arg Asp  Glu Gly Ser
    1010                1015                1020

Ala Arg  Ile Ala Pro Arg Thr  Pro Ala Glu Glu Thr  Leu Ala Arg
    1025                1030                1035

Ile Trp  Ser Glu Val Leu Gly  Val Thr Asp Ile Gly  Val Glu Asp
    1040                1045                1050

Asn Phe  Phe Asp Leu Gly Gly  Asp Ser Ile Leu Ser  Leu Gln Val
    1055                1060                1065

Val Ala  Arg Ala Arg Ala Ala  Gly Leu Arg Leu Thr  Ala Lys Gln
    1070                1075                1080

Thr Phe  Leu Arg Gln Thr Ile  Ala Asp Leu Ala Ala  Asp Ala Val
    1085                1090                1095

Ala Glu  Thr Asp Pro Ala Ala  His Gly Ala Ala Asn  Asp Gly Pro
```

-continued

```
    1100                1105                1110

Val Thr  Gly Glu Leu Pro Leu  Thr Pro Ile Gln His  Trp Phe Phe
    1115                1120                1125

Asn Ser  Leu Gly Asp Ser Leu  Glu Gln Phe Asn Gln  Ser Leu Tyr
    1130                1135                1140

Leu Glu  Leu Ala Glu Gly Pro  Asp Leu Pro Ala Leu  Arg Ala Ala
    1145                1150                1155

Leu Ala  Ala Leu Thr Glu Gln  His Asp Ala Leu Arg  Leu Arg Ala
    1160                1165                1170

Val Ser  Glu Asp Gly Gln Trp  Arg Leu His His Ala  Pro Ala Glu
    1175                1180                1185

Thr Gly  Gln Leu Leu Glu His  Leu Asp Leu Ser Gly  Val Ser Pro
    1190                1195                1200

Asp Glu  Gln Asp Ala Ala Met  Ala Ala Ala Val Asp  Ala Ala Gln
    1205                1210                1215

Arg Asp  Phe Arg Leu Ser Glu  Gly Pro Leu Leu Arg  Ala Arg Leu
    1220                1225                1230

Phe Thr  Leu Gly Asp Ala Arg  Pro Pro Arg Leu Tyr  Leu Val Ala
    1235                1240                1245

His His  Leu Val Ile Asp Gly  Met Ser Trp Arg Ile  Leu Leu Ala
    1250                1255                1260

Asp Leu  Glu Thr Gly Tyr Arg  Leu Ala Ala Asp Gly  Arg Pro Ile
    1265                1270                1275

Asp Leu  Gly Pro Arg Thr Thr  Ser Phe Arg Asp Trp  Ser Arg Arg
    1280                1285                1290

Leu Ser  Arg His Val Ala Asp  Gly Gly Leu Asp Ala  Glu Leu Pro
    1295                1300                1305

Tyr Trp  Lys Gly Val Gln Asp  Ala Ala Arg Glu Thr  Ala Pro Leu
    1310                1315                1320

Pro Val  Asp Thr Gly Gly Leu  Pro Asp Arg Gln Gly  Ala Gln Glu
    1325                1330                1335

Glu Pro  Gly Glu Asn Thr Ala  Gly Ser Ala Arg Thr  Val Ser Val
    1340                1345                1350

Gln Leu  Ser Ala Ala Gly Thr  Glu Ala Leu Leu Arg  Gln Val Pro
    1355                1360                1365

Glu Ala  Tyr Arg Thr Gln Ile  Asn Asp Val Leu Leu  Ser Ala Leu
    1370                1375                1380

Gly Arg  Val Leu Thr Asp Trp  Ala Gly Gly Glu Arg  Val Leu Ile
    1385                1390                1395

Ala Leu  Glu Gly His Gly Arg  Glu Glu Leu Phe Asp  Glu Val Asp
    1400                1405                1410

Leu Thr  Arg Thr Val Gly Trp  Phe Thr Thr Leu Phe  Pro Val Ala
    1415                1420                1425

Leu Arg  Met Pro Ala Asp Arg  Asp Trp Gly Thr Val  Leu Lys Ser
    1430                1435                1440

Val Lys  Glu Gln Leu Arg Ala  Val Pro His Asn Gly  Leu Gly His
    1445                1450                1455

Gly Ala  Leu Arg His Leu Ala  Gly Pro Asn Ser Pro  Leu Glu Asp
    1460                1465                1470

Gly Pro  Glu Pro Glu Val Ser  Phe Asn Tyr Leu Gly  Gln Leu Asp
    1475                1480                1485

Val Ser  Ala Asp Arg Thr Gly  Leu Ala Arg Ala Met  Leu Thr Ser
    1490                1495                1500
```

-continued

```
Glu Gly  Ala Glu Arg Ala Ala  Gly Gln His Arg Ala  Gln Leu Leu
    1505                 1510                 1515

Glu Ile  Asn Gly Val Val Thr  Gly Gly Arg Leu Glu  Phe His Trp
    1520                 1525                 1530

Thr Tyr  Ser Val Asn Arg His  Arg Ala Glu Thr Val  Glu Arg Leu
    1535                 1540                 1545

Ala Ala  Gly Phe Met Thr Ala  Leu Glu Ala Ile Val  Ala His Cys
    1550                 1555                 1560

Ala Ala  Pro Gly Ser Gly Gly  Ala Thr Pro Ser Asp  Phe Pro Leu
    1565                 1570                 1575

Ala Ala  Leu Asp Gln Ala Thr  Val Asp Lys Ile Ala  Gly Asp Gly
    1580                 1585                 1590

Arg Thr  Val Glu Asp Ile Tyr  Pro Leu Thr Ala Met  Gln Ser Gly
    1595                 1600                 1605

Met Leu  Phe His Ala Leu Ser  Glu Ser Gly Arg Asp  Pro Tyr Thr
    1610                 1615                 1620

Gly His  Phe Gly Val Arg Val  Asp Gly Ile Thr Asp  Pro Gly Ala
    1625                 1630                 1635

Leu Ala  Ala Ala Trp Gln Gln  Val Val Asp Arg Thr  Pro Ala Leu
    1640                 1645                 1650

Arg Thr  Ala Ile Val Trp Gln  Asp Val Ala Glu Pro  Leu Gln Val
    1655                 1660                 1665

Val His  Ala Ala Ala Arg Val  Pro Val Thr His His  Asp Leu Arg
    1670                 1675                 1680

Ser Leu  Thr Glu Gln Glu Arg  Gln Ala Ala Leu Asp  Arg Leu Trp
    1685                 1690                 1695

Glu Arg  Arg Glu Glu Thr Val  Ile Asp Leu Ala Val  Ala Pro Ala
    1700                 1705                 1710

Leu Arg  Leu Thr Leu Val Arg  Leu Thr Asp Ser Ala  Val Gln Met
    1715                 1720                 1725

Phe Trp  Thr Ser His His Ile  Leu Met Asp Gly Trp  Ser Phe Ala
    1730                 1735                 1740

Gly Leu  Leu Ser Glu Val Cys  Ala Gln Tyr Thr Ala  Leu Thr Gly
    1745                 1750                 1755

Gly Pro  Arg Val Ala Ala Pro  Ala Arg Arg Pro Tyr  Arg Asp Tyr
    1760                 1765                 1770

Val Gly  Trp Leu Ala Glu Gln  Asp Gln Pro Ala Ala  Glu Ala His
    1775                 1780                 1785

Trp Arg  Ser Val Val Asp Gly  Phe Thr Val Pro Thr  Pro Leu Pro
    1790                 1795                 1800

Tyr Asp  Arg Gln Pro Val Lys  Ala His Gly Thr Arg  Ser Ser Arg
    1805                 1810                 1815

Glu Val  Arg Leu Gln Leu Ser  Ala Glu Arg Ser Gly  Arg Leu Ser
    1820                 1825                 1830

Glu Ala  Ala Arg Ser Ala Arg  Leu Thr Val Asn Thr  Leu Val Gln
    1835                 1840                 1845

Gly Ala  Trp Ala Ile Leu Leu  Ala Arg Tyr Gly Gly  Val Arg Asp
    1850                 1855                 1860

Val Cys  Phe Gly Thr Thr Val  Ser Gly Arg Pro Ala  Thr Leu Pro
    1865                 1870                 1875

Gly Ala  Glu Ser Met Ala Gly  Leu Phe Ile Asn Thr  Val Pro Val
    1880                 1885                 1890
```

-continued

```
Arg Ala  Thr Ile Asp Gly Ala  Gly Ala Gly Asp Gly  Ala Ala Thr
    1895                 1900                 1905

Gly Thr  Val Glu Trp Leu Arg  Arg Leu Gln Ser Glu  Gln Leu Asp
    1910                 1915                 1920

Ser Arg  Gln His Glu His Val  Ser Leu Ala Gln Ile  Gln Arg Trp
    1925                 1930                 1935

Ser Gly  Val Pro Ala Gly Thr  Asn Leu Phe Asp Ser  Ile Val Val
    1940                 1945                 1950

Phe Glu  Asn Tyr Pro Tyr Asp  Ser Asp Ala Ala Ala  Lys Tyr Gly
    1955                 1960                 1965

Leu Thr  Leu Gly Thr Phe Gln  Gly Asp Glu Val Thr  Asn Tyr Ala
    1970                 1975                 1980

Leu Thr  Leu Thr Ala Tyr Val  Ala Asp Glu Leu His  Leu Asn Leu
    1985                 1990                 1995

Gly Tyr  Asp Pro Asp Leu Phe  Asp Glu Ala Thr Val  Glu Arg Met
    2000                 2005                 2010

Ala Gly  His Leu Ala Thr Leu  Leu Asp Ala Val Ala  Ala Ala Pro
    2015                 2020                 2025

His Thr  Pro Val Asp Asp Leu  Pro Leu Leu Asp Ala  Ala Glu His
    2030                 2035                 2040

His Arg  Leu Leu Thr Glu Trp  Asn Asp Thr Ala Ala  Gly Phe Pro
    2045                 2050                 2055

Pro Pro  Arg Pro Val His Glu  Leu Phe Ala Glu Arg  Ala Ala Arg
    2060                 2065                 2070

Thr Pro  Asp Ala Val Ala Val  Ser Asp Ala Thr Arg  Gln Leu Thr
    2075                 2080                 2085

Phe Ala  Glu Leu Glu Thr Arg  Ala Asn Gln Leu Ala  His His Leu
    2090                 2095                 2100

Ala Gly  Leu Gly Val Ala Pro  Gly Thr Leu Val Gly  Val Cys Ala
    2105                 2110                 2115

Asp Arg  Gly Val Asp Ala Val  Val Ala Leu Leu Gly  Val Leu Arg
    2120                 2125                 2130

Ala Gly  Gly Ala Phe Val Pro  Leu Asp Pro Ala Tyr  Pro Ala Glu
    2135                 2140                 2145

Arg Leu  Gln Val Met Leu Glu  Asp Ala Ala Val Pro  Val Val Val
    2150                 2155                 2160

Thr Glu  Glu Arg Leu Leu Asp  Arg Thr Ala Gly His  Asp Ala Thr
    2165                 2170                 2175

Thr Val  Cys Leu Asp Arg Asp  Leu Pro Leu Leu Glu  Glu Leu Pro
    2180                 2185                 2190

Ala Arg  Pro Pro Tyr Thr Ala  Val Ala Pro Asp Asp  Leu Ala Tyr
    2195                 2200                 2205

Val Val  Tyr Thr Ser Gly Thr  Thr Gly Arg Pro Lys  Gly Val Met
    2210                 2215                 2220

Val Glu  His Arg His Val His  His Met Val His Ala  Trp Asp Arg
    2225                 2230                 2235

Arg Tyr  Gly Leu Ala Ala Leu  Gln Pro Arg Ala Leu  Ser Val Ser
    2240                 2245                 2250

Ser Ile  Ser Val Asp Leu Phe  Phe Ser Asp Phe Leu  Leu Ser Ala
    2255                 2260                 2265

Leu Phe  Gly Gly Thr Met Val  Ile Cys Pro Gln Asp  Ala Val Ala
    2270                 2275                 2280

Asp Gln  Val Ala Leu Thr Asp  Leu Leu Leu Lys Ser  Arg Ala Gln
```

-continued

```
    2285                2290                2295

Leu Met  Val Thr Val Pro Thr  Leu Ala Arg Ala Val  Val Ala Glu
    2300                2305                2310

Leu Ala  Trp Arg Gly Val Thr  Pro Glu Ala Leu Arg  Val Leu Met
    2315                2320                2325

Val Gly  Ser Glu Gly Trp Pro  Ala Asp Ala Ala Ala  Glu Ile Leu
    2330                2335                2340

Ala Gly  Leu Ala Pro Gly Thr  Val Leu Val Asn Ala  Tyr Gly Ser
    2345                2350                2355

Thr Glu  Thr Thr Val Asp Ser  Thr Val Phe Gln Leu  Gly Arg Asp
    2360                2365                2370

Pro Leu  Gly Asp Ala Ala Phe  Val Pro Val Gly Arg  Pro Leu Ala
    2375                2380                2385

Asn Thr  Arg Ile Tyr Val Leu  Asp Glu Arg Met Arg  Pro Val Pro
    2390                2395                2400

Thr Gly  Val Val Gly Glu Cys  Tyr Ile Gly Gly Asp  Gly Val Ser
    2405                2410                2415

Arg Gly  Tyr Leu Gly Arg Pro  Glu Leu Thr Ala Glu  Arg Phe Leu
    2420                2425                2430

Asp Asp  Pro Phe Ala Pro Glu  Pro Gly Ala Arg Met  Tyr Arg Thr
    2435                2440                2445

Gly Asp  Leu Ala Arg Trp Arg  Ala Asp Gly Asn Leu  Glu Cys Leu
    2450                2455                2460

Gly Arg  Val Asp Asp Gln Val  Lys Ile Arg Gly Phe  Arg Val Glu
    2465                2470                2475

Leu Gly  Glu Val Glu Ala Ala  Leu Ala Arg His Pro  Ala Ile Asp
    2480                2485                2490

Ser Ala  Ala Ala Ala Ile Arg  Lys Asp Asp Gly Gly  Pro Ala Arg
    2495                2500                2505

Leu Val  Gly Tyr Val Val Pro  Ala Ala Gly His Thr  Pro Asp Leu
    2510                2515                2520

Ala Glu  Leu Arg Ala Phe Ala  Ala Glu Arg Leu Pro  Ser Pro Ala
    2525                2530                2535

Val Pro  Thr Ala Tyr Met Val  Leu Asp Ala Leu Pro  Met Thr Pro
    2540                2545                2550

Ser Gly  Thr Val Ala Arg Arg  Ala Leu Pro Ala Pro  Ala Gly Ala
    2555                2560                2565

Gln Asp  Ala Ala Arg Pro Tyr  Thr Ala Pro Gly Ser  Ala Thr Glu
    2570                2575                2580

Leu Leu  Leu Cys Gly Ile Trp  Gln Glu Val Leu Gly  Val Glu Arg
    2585                2590                2595

Val Gly  Val His Asp Asn Phe  Phe Asp Leu Gly Gly  Asp Ser Ile
    2600                2605                2610

Leu Ser  Ile Arg Val Ile Ser  Arg Ile Arg Ala Thr  Leu Gly Val
    2615                2620                2625

Ala Pro  Ser Pro Arg Gln Leu  Phe Asp Thr Pro Thr  Val Ala Gly
    2630                2635                2640

Leu Ala  Ala Thr Leu Gly Arg  Asp Asp Pro Ser Ala  Ala Ala Asp
    2645                2650                2655

Val Pro  Leu Glu Pro Ala Asp  Arg Gly Ala Pro Leu  Pro Leu Ser
    2660                2665                2670

Ser Ala  Gln Gln Arg Gln Trp  Phe Leu His Asn Phe  Asp Pro Asp
    2675                2680                2685
```

-continued

```
Ser Ser Glu Tyr His Ile Val Thr Gly Leu Arg Leu Asp Gly Asp
    2690                2695                2700

Leu Asp Val Ala Ala Leu Arg Gly Ala Leu Asn Gly Leu Val Ala
    2705                2710                2715

Arg His Glu Ala Leu Arg Thr Thr Tyr Ala Ala Thr Gly Glu Gly
    2720                2725                2730

Ala Glu Gln Ile Val His Pro Ala Gly Glu Val Val Cys Glu Arg
    2735                2740                2745

Thr Asp Leu Ser Glu Val Pro Glu Asp Gln Arg Glu Asp Thr Leu
    2750                2755                2760

Arg Gly His Ile Asp Arg Ala Ala Ala Arg Pro Phe Gly Leu Thr
    2765                2770                2775

Glu Gly Pro Val Leu Arg Ala Glu Leu Phe Arg Leu Gly Ala Arg
    2780                2785                2790

Asp His Leu Leu Leu Leu Val Ile His His Ile Ala Thr Asp Gly
    2795                2800                2805

Val Ser Met Gln Val Leu Thr Glu Glu Leu Gly Val His Tyr Ala
    2810                2815                2820

Ala Ala Leu Asp Gly Thr Pro Pro Ala Leu Pro Ala Leu Pro Val
    2825                2830                2835

Ser Tyr Ala Asp Tyr Ala Ala Trp Gln Arg Arg Met Leu Ser Gly
    2840                2845                2850

Pro Ala Leu Asp Gly His Leu Ala Tyr Trp Gln Glu Arg Leu Ala
    2855                2860                2865

Gly Val Arg Pro Leu Glu Leu Pro Thr Asp Arg Pro Arg Pro Ala
    2870                2875                2880

Val Arg Ser Ser Ala Gly Arg Met Leu Leu Ile Glu Ile Glu Pro
    2885                2890                2895

Arg Val Ala Ala Gly Leu Lys Glu Leu Ala Arg Arg His Asp Ala
    2900                2905                2910

Thr Leu Phe Met Ala Leu Thr Ala Ala Val Gln Leu Leu Leu Ala
    2915                2920                2925

Arg Tyr Thr Gly Gln Pro Asp Ile Val Val Gly Thr Pro Ala Ala
    2930                2935                2940

Gly Arg Gly Arg Gln Glu Leu Glu Gly Leu Val Gly Leu Phe Val
    2945                2950                2955

Asn Thr Val Ala Leu Arg Ser Thr Val Asp Glu Ser Gly Thr Phe
    2960                2965                2970

Asp Ala Phe Leu Gly Ala Val Arg Asp Thr Val Leu Glu Ala Phe
    2975                2980                2985

Val His Glu Asp Val Pro Phe Asp Arg Leu Val Glu Val Leu Arg
    2990                2995                3000

Pro Arg Arg Asp Pro Ser Arg Asn Ala Leu Val Glu Val Phe Val
    3005                3010                3015

Gly Leu Glu Thr Asp Arg Ser Ala Pro Pro Ala Leu Pro Gly Leu
    3020                3025                3030

Thr Val Thr Glu Val Pro Phe Val Ser Gly Glu Val Ser His Asp
    3035                3040                3045

Leu Ser Phe Asp Phe Val Asp Gly Pro Asp Gly Leu Lys Ala Ala
    3050                3055                3060

Ile Gly Tyr Ser Thr Ala Leu Phe Asp Asp Gly Thr Val Glu Arg
    3065                3070                3075
```

-continued

```
Met Ala  Gly Gln Phe Gln Ala  Leu Leu Ala Ala Val  Leu Glu Asp
    3080                 3085                 3090

His Arg  Ala Leu Ala Asp Ile  Ala Pro Ala Asp Glu  Ala Glu Val
    3095                 3100                 3105

Arg Arg  Leu Ala Glu Leu Arg  Gln Ala Ala Pro Ser  Glu Pro Asp
    3110                 3115                 3120

Ala Ser  Glu Thr Asp Gly Ala  Pro Ala Ala Tyr Arg  Ala Pro Gly
    3125                 3130                 3135

Thr Ala  Ala Glu Arg Ala Leu  Ala Glu Ile Trp Ala  Ala Val Leu
    3140                 3145                 3150

Gly Val  Pro Arg Val Gly Thr  Asp Asp Asn Phe Phe  Gln Leu Gly
    3155                 3160                 3165

Gly Asp  Ser Leu Leu Ser Ile  Gln Ala Val Gln Arg  Met Arg Gln
    3170                 3175                 3180

Ala Gly  Leu Ala Val Thr Thr  Lys Asp Leu Phe Val  His Gln Ser
    3185                 3190                 3195

Ile Ala  Pro Leu Ala Ala Leu  Ala Glu Glu Arg Ala  Ala Asp Arg
    3200                 3205                 3210

Pro Glu  Ala Pro Gln Ala Gln  His Asp Asp Ala Gly  Thr Ala Gly
    3215                 3220                 3225

Glu Ile  Pro Leu Thr Pro Ile  Gln Arg Asp Tyr Phe  Ala Ala Gly
    3230                 3235                 3240

Pro Leu  Ala Pro His His Phe  Thr Gln Ser Val Phe  Leu Glu Leu
    3245                 3250                 3255

His Ala  Asp Leu Asp Glu Pro  Ala Leu Arg His Ala  Leu Ala Ala
    3260                 3265                 3270

Leu Ile  Gly His His Asp Ala  Leu Arg Thr Arg Phe  Val Arg Glu
    3275                 3280                 3285

Asp Gly  Asp Trp Arg Gln Tyr  Ala Thr Pro Pro Glu  Pro Val Asp
    3290                 3295                 3300

Ile Leu  Arg Arg His Asp Leu  Ser Gly Leu Pro Glu  Ala Gln Arg
    3305                 3310                 3315

Ala Ala  Ala Met Asp Glu Leu  Ala Ala Ser Ala Asp  Ala Gly Leu
    3320                 3325                 3330

Asp Leu  Ala Ala Gly Pro Pro  Ala Ala Ala Leu Leu  Phe Val Phe
    3335                 3340                 3345

Gly Pro  Gly Glu Arg Pro Ala  Leu Phe Val Thr Ala  His His Leu
    3350                 3355                 3360

Val Val  Asp Gly Val Ser Trp  Arg Ile Leu Leu Glu  Asp Leu Glu
    3365                 3370                 3375

Ala Gly  Tyr Val Gln Ala Arg  Asp Gly Lys Pro Val  Ser Leu Gly
    3380                 3385                 3390

Ala Lys  Ser Thr Ser Phe Gly  Gln Trp Ala His Arg  Leu Ala Arg
    3395                 3400                 3405

His Ile  Ala Asp Gly Gly Leu  Ala Glu Gln Ala Ala  Tyr Trp Gln
    3410                 3415                 3420

Ala Leu  Pro Asp Gly Thr Glu  Val Pro His Asp Gly  Ser Gly Pro
    3425                 3430                 3435

Ala Val  Val Glu Ser Val Gln  Thr Val Thr Val Glu  Leu Pro Glu
    3440                 3445                 3450

Asp Thr  Ser Glu Val Leu Leu  Arg Arg Ser Ala Gly  Val Phe Arg
    3455                 3460                 3465

Thr Arg  Phe His Glu Val Leu  Phe Ala Ala Leu Ala  Gly Thr Leu
```

-continued

```
    3470                3475                3480

Ala Arg  Trp Thr Gly Glu Arg  Gln Val Val Phe Asp  Thr Glu Gly
    3485                3490                3495

His Gly  Arg Glu Asp Leu Phe  Asp Asp Val Asp Leu  Ser Arg Thr
    3500                3505                3510

Val Gly  Trp Phe Thr Thr Glu  Tyr Pro Val Ala Leu  Glu Val Ala
    3515                3520                3525

Gly Asp  Arg Asp Asp Trp Pro  Ala Leu Ile Arg Ser  Val Arg Gly
    3530                3535                3540

Gln Leu  Arg Ser Leu Pro Gly  Asn Gly Phe Gly Tyr  Gly Ala Leu
    3545                3550                3555

Arg His  Leu Ser Pro Ala Gly  Thr Pro Gly Ala Ala  Leu Ala Glu
    3560                3565                3570

Arg Ala  Pro Ala Gln Val Val  Phe Asn Tyr His Gly  Gln Ala Asp
    3575                3580                3585

Glu Ala  Gln Arg Ala Ala Glu  Ser Asp Leu Tyr His  Ala Phe Gly
    3590                3595                3600

Asp Pro  Ile Gly Arg Glu Gln  Arg Pro Asp Glu Leu  Thr Gly His
    3605                3610                3615

Pro Val  Glu Val Val Gly Ala  Val His Ser Gly Arg  Leu Arg Phe
    3620                3625                3630

Thr Trp  Tyr Phe Ser Arg Asn  Val His His Arg Ala  Thr Ile Asp
    3635                3640                3645

Lys Val  Ala Glu Asp Phe Ala  Asp Ala Leu Arg Ala  Ile Ala Arg
    3650                3655                3660

His Ile  Thr Glu Arg
    3665
```

<210> SEQ ID NO 5
<211> LENGTH: 11007
<212> TYPE: DNA
<213> ORGANISM: Streptomyces hygroscopicus

<400> SEQUENCE: 5

```
atgaccagct ctgcagcgga ccagcccgac aacccgaaca ccaccacccc ggcgtcgcgt     60

gccgagcgca ccgccgcgct gccggcccat gtgcaggagc tgctgcgcgc ccggctggcc    120

ggccgggccg ccgcgacggg cggcgcggac accatcccgc gcatcgggca cgacggcccc    180

gtcgcgctct cgcccgccca ggaacgcctc tggtacctgc atgagctcga accggagagc    240

aacgagtaca acaccctgcg cgtcctgcgg ctgcgcggcg acctcgaccc cggcgcgctg    300

tccgcggcgc tgagcgagat cgtcgcccgg cacggcgcgc tccgcaccac cttcggctcc    360

cgcgaggggc acgccgagca gaccgtgcat ccgcccgtac cgacaccgct gccgctcgtc    420

gacctgtcgg cggcggacga cggcgagcgg gacgacgcgc tgcggaccct gctgcagtac    480

gaggcccggc gccccttcga cctgcgccgc ggcccggtgc tgcgggcgca gctgatccgg    540

ctggcggccg acgaccatgt cctcgcgctg gccctgcatc acatcgtcac cgacggctgg    600

tcgatgggcg tgctcaccgg cgagctcacc gcccactacg ccgcgacgct gcgcggtgcg    660

cccgccgtac tgcccgaact tccggtgagc tacctcgatg tcgccgtctg gcagcgtgac    720

cagctgagct ccgcgcggct gcgcgagggg ctcgaccact ggcgccggga gctggccggg    780

ctggtcccgc tcgatctgcc gacgacctgg cagcggccgc cggtccgcac cagcgccgga    840

gcgctgcact ccttcgagat ccccccggcg gtcgccgcac gccttcggga gctgggccgg    900
```

-continued

```
gaacagggcg ccacgctgtt catggcgctg gtcgccgcgg tccagctgct gctgtcgcgc    960
tggtcggggc agcgggacat cgcggtgggc accgccgcgg ccgggcgcgg ccggaccgag   1020
accgagaatc tgatcggctt cttcgtcaac aatctggtcc tgcgctcccg gatcgatgag   1080
acgcggtcgt tcaccgagct gctgcgggcg gtacgcgcga cggtcctgga cgccttcgcc   1140
cacgaggatg tgccgttcca gcgggtcgtc gaggcgctgc atccggagcg cgacctcagc   1200
cggccgccgc tggccgaggt cgcggtgaat ctgcacaaca ccccgcggac cgacacggag   1260
ctgcccgggc tgcggatcga ggagatgccg ccgccggtgt tcgcctccag catggacctc   1320
tcgttcgact tcaccgagcg cgacgaccgg ctcgaagggc acctcaccta caacaccgat   1380
ctgttcgccg cggacgccgc cgcgcggatg gccgcgcagc tggtcaccct gctcgaggac   1440
ctcacccgcc ggcccgcggt cccggtggcc gggctggccg tgctgccggc cgccgagcac   1500
cgtcgggtga ccgaggagtg gccgcactcc gggcccggcc gggagccgcg taccgcaccg   1560
gagttgttcg ccgcgcaggt cgcgcggacc cctgatgcgg atgcgctggt ctccgacgag   1620
gagacgctca gctatgccga gctggacggc cgtatcaacc agtgggcgcg gctgctactg   1680
gcccggggtg ccgggccgga gacgctggtg gcggtggcgc tgccccgctc cgcgcagatg   1740
gtcacggcga tcctggcgat ccagaagacc ggtgccgcct atctgccgct ggacccgaag   1800
agccccgcgg aacgcaaccg gctgatgatc gaggacgccc gcccgctgct ggtgctgacc   1860
tcggccgggt tcggcgacgg cgcggaactc ggcgcgcccg cactgttcct ggacgacccg   1920
gacacccgcg ccgccgcagg cgagctgtcc gccggcccgc tggcggccgc cgagctgccc   1980
gccccgctgc tgcccggcca cccggcctac gtcatctaca cctccggttc caccggccgc   2040
cccaagggcg tggtggtcac ccacaccggt gtgcacggcc tcgtggcggc gcagtcggcg   2100
cacttccgta ccgggcacgg cgcgcgggtg ctgtcgttcg cctcgctcgg cttcgacgcg   2160
gccttctccg agctgggcat ggcgctgctg tccggcggtg cgctggtcgt cgtcgaccag   2220
gagcggatcc tgcccggaca gccgctggcc gacgtgctgg ccgagcaccg ggtcacccat   2280
gtgacgctgc cgcccagcgc gctgtccgcg ctgaccccgg ggacgctgcc gaaggacctc   2340
accctggtcg tggccggcga ggcctgcccg cccgcggtgg cccgcacctg gtccgcccat   2400
caccgcatga tcaacgccta cggccccacc gagtccacgg tctgcgccag catgagcgcc   2460
gcgctgaccc cggacaccgt cagcggcgac tcggtcccca tcggccgccc gctctccggc   2520
gtccgggtca gcgtcctgga cgaccggctg cgcccggtgc cggccggcgt ccccggcgag   2580
gtgtatctct ccggcgccgc gctggcccgc ggctacctcg ggcggctcgc gctgaccgcg   2640
gagcggttcg tcgccgaccc gtacggtccg ccgggaagcc ggatgtaccg caccggcgac   2700
cgcgcccgct ggctggccgg cggcgacctg gactacctgg gccgcaccga cgaccaggtc   2760
aaactgcgcg gcttccggat cgagctcggc gaggtcgagg ccgtactgtc gcgccacgac   2820
ggggtcggcg cggtggccgc cacggtgcac aaggacgagc ggggcacccg ccgcctggtg   2880
gcgtacgtcg tcccggcgcg ggaggacgcg gccgacccgg cgcggctgcg cgagttcgcc   2940
cgcgaggtgc tgcccgagca catggtgccc tcggtcttcg tgccgctgga ccggctgccg   3000
ctgaacgcca acggcaaggt cgaccggcgg gcgctgcccg cacccgacat ccggcgcgac   3060
gagggcagcg cccgtatcgc gccgcgcacc ccggcggagg agacgctggc gcgcatctgg   3120
tcggaggtgc tgggcgtcac ggacatcggc gtcgaggaca acttcttcga cctcggcggc   3180
gactccatcc tcagccttca ggtggtggcg cgggcccggg ccgccggact gcggctgacc   3240
gccaagcaga ccttcctgcg gcagaccatc gccgatctcg ccgccgacgc cgtcgccgag   3300
```

-continued

```
accgaccccg ccgcgcacgg tgcggccaac gacggcccgg tcaccggcga gctgccgctc   3360
acccccatcc agcactggtt cttcaactcc ctcggcgaca gcctggagca gttcaaccag   3420
tcgctgtatc tggagctggc cgagggcccc gacctcccgg cgctgcgcgc cgcactggcc   3480
gcgctgaccg aacagcacga cgcactgcgg ctccgcgccg tatccgagga cgggcagtgg   3540
cggctgcacc acgcgcccgc cgagaccggt caactcctcg aacacctcga tctgtccggc   3600
gtctcgcccg acgagcagga cgccgcgatg gcggccgccg tcgacgcggc gcagcgggac   3660
ttccggctgt ccgaggggcc gctgctgcgg gcccggctgt tcaccctcgg cgacgcccgg   3720
ccgccccggc tgtacctcgt cgcgcaccac ctcgtcatcg acggcatgtc ctggcgcatc   3780
ctgctggcgg acctggagac cggctaccgc ctggcggcgg acggccggcc gatcgacctg   3840
gggccccgga ccacctcgtt ccgcgactgg tcgcgccggc tgtcgcgcca tgtcgcggac   3900
ggcggcctgg acgccgaact gccgtactgg aagggcgtac aggacgcggc gcgcgagacc   3960
gccccgctcc ccgtcgacac cggcgggctc cccgaccgcc agggcgccca ggaggagccc   4020
ggcgagaaca ccgccgggtc ggcccgcacc gtctccgtac agctgtccgc cgcgggcacc   4080
gaggcgctgc tgcggcaggt gcccgaggcc taccgcaccc agatcaacga cgtcctgctc   4140
agcgcgctgg gccgggtgct gaccgactgg gcgggcggcg agcgggtgct gatcgccctg   4200
gagggccacg gccgcgagga gctcttcgac gaggtggacc tcacccgcac cgtcggctgg   4260
ttcaccaccc tcttcccggt cgccctgcgg atgccggccg accgggactg gggaacggtc   4320
ctcaagagcg tcaaggaaca gctgcgggcg gtgccccaca acggactcgg ccatggcgcg   4380
ctgcgtcatc tggcagggcc caactcccct ctggaggacg gtccggagcc cgaggtcagc   4440
ttcaactacc tcggccagct ggacgtgtcc gccgaccgca ccggcctcgc ccgcgccatg   4500
ctcaccagcg agggcgccga gcgggccgcc ggccagcacc gtgcgcagct gctggagatc   4560
aacggcgtgg tcaccggcgg ccggctggag ttccactgga cgtactcggt gaaccggcac   4620
cgcgcagaga ccgtcgaacg gctcgccgcg ggcttcatga ccgcgctgga agcgatcgtg   4680
gcgcactgcg ccgcccccgg ttccggcggc gccaccccgt ccgacttccc gctggccgcc   4740
ctcgaccagg ccaccgtcga caagatcgcc ggcgacggcc gcacggtcga ggacatctac   4800
ccgctcaccg cgatgcagag cggcatgctc ttccacgcgc tgagcgagtc cggacgcgac   4860
ccgtacaccg ggcacttcgg cgtccgcgtg gacggcatca ccgacccggg ggcactggcc   4920
gcggcctggc agcaggtcgt cgaccggacc cccgccctgc gcaccgccat cgtctggcag   4980
gacgtcgcgg aacccccttca ggtggtgcac gcggccgccc gtgtgccggt cacccatcac   5040
gacctgcggt ccctgaccga gcaggaacgg caggccgccc tggaccggct gtgggagcgg   5100
cgcgaggaga ccgtcatcga tctcgccgtc gcgcccgcgc tgcggctgac cctcgtccgg   5160
ctcaccgaca gcgccgtcca gatgttctgg acctcgcacc acatcctgat ggacggctgg   5220
agcttcgccg ggctgctgtc ggaggtgtgc gcccagtaca ccgcgctgac cggcggcccc   5280
cgcgtggcgg ccccggcccg ccgcccgtac cgcgactatg tcggctggct ggccgaacag   5340
gaccagccgg ccgccgaggc gcactggcgc tcggtggtcg acgggttcac ggtgccgacg   5400
ccgctgccct acgaccggca gccggtgaag gcacacggca cccggtcctc gcgtgaggtg   5460
cggctgcagc tgtccgccga gcgctccggg cggctgtccg aggccgcccg gtcggcgcgg   5520
ctgaccgtca acacgctggt gcagggcgcc tgggcgatcc tgctggcgcg ctacggcggg   5580
gtgcgcgacg tctgcttcgg caccaccgtc tccggccgtc ccgccaccct gcccggcgcc   5640
```

-continued

```
gagtcgatgg ccgggctgtt catcaacacc gtgccggtac gggcgaccat cgacggtgcc   5700
ggtgccggcg acggcgccgc caccggcacc gtcgagtggc tgcggcggct gcagagcgag   5760
cagctcgact cccggcagca cgagcatgtc tcgctggcgc agatccagcg ctggagcggc   5820
gtaccggccg gcaccaacct cttcgacagc atcgtcgtct tcgagaacta cccctacgac   5880
agcgatgcgg ccgccaagta cgggctgacc ctcggcacgt tccagggcga cgaggtcacc   5940
aactacgccc tcaccctgac cgcgtacgtg gccgacgagc tgcatctcaa cctcggctac   6000
gacccggatc tgttcgacga ggcgaccgtc gagcggatgg ccgggcatct ggcgacgctg   6060
ctcgacgccg tcgccgccgc cccgcacacc ccggtggacg acctcccgct gctcgatgcg   6120
gccgaacacc accggcttct caccgagtgg aacgacaccg ccgccggctt cccgccgccg   6180
cggccggtcc atgagctctt cgccgagcgg gccgcccgta ccccggacgc ggtggcggtc   6240
agcgacgcca cccggcagct gaccttcgcc gagctggaga cccgcgccaa ccaactggcg   6300
caccacctgg ccggtctggg cgtggcgccc ggcacgctgg tcggggtgtg cgccgaccgc   6360
ggggtggacg ccgtggtggc gctgctgggc gtgctgcggg ccggcggtgc cttcgtaccg   6420
ctggaccccg cctatccggc ggagcggctc caggtcatgc tggaggacgc cgcggtgccg   6480
gtcgtggtga ccgaggagcg gctgctggac cggaccgccg ggcacgacgc gacgacggtg   6540
tgcctggacc gcgatctgcc gctgctggag gagctgccgg cccgcccgcc gtacaccgcc   6600
gtggcaccgg acgacctggc gtatgtcgtc tatacgtcgg gcaccaccgg gcgccccaag   6660
ggcgtgatgg tcgagcaccg gcacgtccac cacatggtgc acgcctggga ccggcgctac   6720
gggctcgccg cgctgcaacc gcgcgcgctg tccgtctcca gcatctccgt cgacctgttc   6780
ttcagcgact tcctgctctc cgccctcttc ggcggcacga tggtgatctg tccgcaggac   6840
gccgtcgccg accaggtggc gctgaccgat ctgctgctca agagccgggc ccagctgatg   6900
gtgacggtgc cgacgctggc ccgcgcggtg gtcgccgagc tcgcctggcg cggtgtgaca   6960
ccggaggcgc tgcgggtgct gatggtgggc tccgagggct ggccggccga tgccgcggcc   7020
gagatcctgg ccggtctcgc gccgggcacg gtgctggtca acgcgtacgg atcgaccgag   7080
accacggtcg actccacggt cttccagctc ggccgcgacc cgctgggcga cgccgccttc   7140
gtaccggtcg gcaggccgct cgccaacacc cggatctatg tgctggacga gcggatgcgc   7200
ccggttccca ccggcgtcgt cggcgagtgc tacatcggcg gcgacggagt gtcgcgcggc   7260
tatctgggcc gcccggagct gaccgccgag cgtttcctcg acgacccgtt cgcgccggag   7320
ccgggcgccc ggatgtaccg gaccggtgac ctcgcgcgct ggcgggccga cggcaacctc   7380
gaatgcctcg gccgggtcga cgaccaggtc aagatccgcg gcttccgggt ggaactcggc   7440
gaggtggagg ccgcgttggc ccgccacccg gcgatcgact cggcggccgc cgcgatccgc   7500
aaggacgacg gtgggccggc ccgtctggtg ggctatgtcg tgcccgccgc cggccacacc   7560
cccgacctgg ccgagctacg ggccttcgcc gccgaacggc tgccgtcgcc cgccgtcccc   7620
accgcgtaca tggtgctgga cgcgctgccg atgacgccga gcggcaccgt cgcccggcgt   7680
gcgctgccgg ccccggccgg ggcgcaggac gccgcccggc cctacaccgc gccgggcagc   7740
gccaccgagc tgctgctctg cggtatctgg caggaggtcc tgggcgtcga acgggtcggc   7800
gtgcacgaca acttcttcga cctgggcggc gactcgatcc tcagcatccg ggtcatctcc   7860
cggatccggg ccacgctggg cgtcgccccg tcgccccgcc agctcttcga caccccgacg   7920
gtggccggtc tcgccgccac cctcggccgg gacgacccct cggcggccgc cgacgtcccc   7980
ctggagccgg ccgaccgcgg cgcaccgctg ccgctgtcgt ccgcccagca acgccagtgg   8040
```

-continued

```
ttcctgcaca acttcgaccc ggacagcagc gagtaccaca tcgtcaccgg gctccggctc   8100
gacggtgatc tggacgtcgc ggcgctgcga ggggccctga acgggctcgt cgcccggcac   8160
gaggcgctgc gtaccaccta cgcggccacc ggcgagggcg ccgagcagat cgtgcacccc   8220
gcgggcgagg tggtctgcga gcgtacggat ctgtccgagg tgcccgagga ccagcgcgag   8280
gacaccctgc gcgggcacat cgaccgcgcc gccgcccggc cgttcggcct caccgagggc   8340
ccggtcctgc gcgccgaact gttccggctc ggcgcccgtg accatctgct gctgctcgtc   8400
atccaccaca tcgccaccga cggtgtctcg atgcaggtgc tcaccgagga gctcggcgtc   8460
cactacgccg cggcgctcga cggcacaccg cccgccctgc cggcgctgcc ggtctcctac   8520
gccgactacg cggcctggca gcgccggatg ctgtccggcc cggcgctgga cggccatctc   8580
gcctactggc aggagcggct ggccggtgtc cggccgctgg agctgcccac cgaccggccc   8640
cggccggcgg tccgcagctc cgcgggccgg atgctgctga tcgagatcga gccgcgggtg   8700
gccgcgggcc tcaaggaact ggcccgccgc catgacgcca ccctgttcat ggcgctcacc   8760
gcggcggtcc agctgctgct ggcccgctac accggacagc cggacatcgt cgtgggcacc   8820
ccggccgccg gccggggccg gcaagaactc gaggggctcg tcgggctgtt cgtcaacacg   8880
gtggcgctgc ggtccaccgt cgacgagagc gggaccttcg acgccttcct cggtgcggtg   8940
cgcgacaccg tcctcgaagc gtttgtgcac gaggacgtgc cgttcgaccg gctggtcgag   9000
gtgctgcgac cgcgccgcga ccccagccgt aacgcactgg tggaggtgtt cgtcggactg   9060
gagacggacc ggtcggcgcc gccggcgctg cccggactga cggtgaccga ggtcccgttc   9120
gtcagcggcg aggtcagcca tgacctcagc ttcgacttcg tcgacgggcc cgacggcctg   9180
aaggcggcca tcggctacag caccgcgctg ttcgacgacg gcaccgtcga gcggatggcc   9240
ggccagttcc aggcgctgct cgccgcggtc ctggaggacc atcgcgcgct cgccgacatc   9300
gcacccgcgg acgaggccga ggtgcggcgg ctcgccgaac tgcggcaggc cgcgccctcg   9360
gagcccgacg cgtcggaaac cgacggcgcg ccggccgcct accgcgcgcc cgggaccgct   9420
gccgagcggg ccctggcgga gatctgggcc gccgtgctgg gggtgccgcg ggtcgggacc   9480
gacgacaact tcttccagct gggcggcgac tccctgctca gcatccaggc ggtgcagcgg   9540
atgcggcagg ccggcctggc ggtgaccacc aaggatctgt tcgtccacca gagcatcgcc   9600
ccgctggcgg ccctcgccga ggaacgggcg gcggaccggc cggaggcccc ccaggcgcag   9660
cacgacgatg ccgggacggc gggcgagata ccgctcaccc cgatccagcg cgactacttc   9720
gcggccgggc cgctcgcccc gcaccacttc acccagtcgg tgttcctcga actgcacgcc   9780
gatctcgacg agccggcgct gcggcacgca ctggccgcgc tgatcggcca ccacgacgcc   9840
ctgcggaccc gcttcgtacg cgaagacggc gactggcggc agtacgccac cccgccggag   9900
ccggtggaca tcctgcgccg gcacgacctg tccgggctgc cggaggctca acgggccgcc   9960
gccatggacg agttggcggc ctcggccgac gccgggctcg atctggcggc cgggccgccg  10020
gccgcggcgc tgctgttcgt cttcgggccc ggggagcggc cggcgctgtt cgtgaccgcg  10080
caccatctcg tcgtcgacgg cgtctcctgg cggatcctgc tggaggacct ggaagccggc  10140
tacgtccagg cccgcgacgg gaagccggtg tccctgggcg ccaaaagcac ctcgttcggg  10200
cagtgggcgc accggctcgc ccggcacatc gccgacggcg gcctcgccga gcaggccgcc  10260
tactggcagg cgctgcccga cggcaccgag gtcccgcacg acggctcggg gcccgcggtg  10320
gtggagtccg tgcagaccgt cacggtggag ctgccggagg acaccagcga ggtgctgctg  10380
```

-continued cgccggtccg ccggggtctt ccggacccgc ttccacgagg tgctgttcgc cgcgctcgcc 10440
ggcaccctgg cccggtggac gggcgaacgc caggtcgtgt tcgacaccga gggccacggc 10500
cgggaggacc tcttcgacga cgtcgatctc tcccggaccg tcggctggtt caccaccgag 10560
taccccgtcg cccttgaggt ggccggcgac cgggacgact ggccggcgct catcaggtcg 10620
gtacgcggac agctgcggtc gctgcccggc aacggcttcg gttacggcgc gctgcggcat 10680
ctgagcccgg ccggcacccc gggtgccgca ctcgccgaac gggcccccggc ccaggtggtg 10740 ttcaactacc acggccaggc cgacgaggcg cagcgcgcgg cggagagcga cctctaccac 10800
gcgttcggcg acccgatcgg ccgggagcag cggcccgacg agctgaccgg gcacccggtg 10860
gaggtggtgg gcgccgtgca ctccgggcgg ctccgcttca cctggtactt ctcgcgcaat 10920
gttcatcaca gggccaccat cgacaaggtg gccgaggact tcgccgacgc gctgcgcgcc 10980
atcgcccggc acatcacgga gcggtga 11007

<210> SEQ ID NO 6
<211> LENGTH: 972
<212> TYPE: DNA
<213> ORGANISM: Streptomyces hygroscopicus

<400> SEQUENCE: 6
atgtccgcca cgccgcgccc gcgacccgtt ctacggccgt tccgccccgg agacggccgc 60
tcgctgctgg cggcctggtg ccgcagcgcc ccggacgatc cgatcaccgc cgcccgcttc 120
cggacgctga tcctgctcga ccccaatttc gacccagagg ggttacgggt ggccgatctc 180
gacgggcagg tggtgggcgc cgtctacgcc gtgcgccgcc gtaccccgct ggccggcacc 240
gacctggagc cggacgtcgg ctggatcctg ttcttcttcg tcgatccgcc gcaccgccgt 300
acgggcctcg gccgccggct gctcaccgat gccctcgact ggctgcgcgg acacggccgc 360
acccgggtcg acttcgcccc gtacgccccc cactacgtgc tccccggcct ggaccgggcc 420
gcgtacccgg aggccgcccg gctgctggcg agcctcggct tccgtccccg ctacgaggcc 480
gcggcgatgg accgcggcct ggtcggctac cgcatgccgg acgaggtacg gcggcacgag 540
gcggccctga cggcgcgcgg ccaccgattc ggcaccccgt ccgacgacga tctggtggac 600
ctgctcgggc tggccgagga gttcaccccc gactgggcgc gggcgatccg gcagtgcctg 660
accggcggcg cccctctgga ccgcatcgtc agcgcccgcg cacccgacgg gcggatggcg 720
ggctgggcca tgcacggcgc gtacgacggt acggccgagc ggttcggccc cttcggcgta 780
cggaaggagc tgcgcggcgc cggtctgggc aaggtgctgc tgcatctgac gctggagcgg 840
atgcgggcgc tcggcgtgca cggggcgtgg ttcctgtgga cgggcgagca gagcccggcg 900
gggcatctct accgcgcgag cggattcacc acgacccgga ggttcacggt gctgcggtgg 960
gaggcgggat ga 972

<210> SEQ ID NO 7
<211> LENGTH: 1416
<212> TYPE: DNA
<213> ORGANISM: Streptomyces hygroscopicus

<400> SEQUENCE: 7
atgaggcgcc gtacattcac ggccggggcc gcggcggggg ccgccctgtt ggccggggcc 60
ggatgcgacg cgcccggtgg cgccgggcac ggagacggag agcacggaga cggagacggc 120
ggtgacggcc ggggcagcgg cggccgtcgc ggcgcccccg tcaccctgac cgtcctcacg 180
cactacgcga gcgaaccgct cgcctcggcg ctgcaaaccg tcgtcgacgc ctggaacgcg 240

-continued acgcaccggc gcatcacggt gcgcacggcc gcggtcaagt tccccgatct gctgacgact 300
tacatggtgc ggcaggccgc gggccagggc gccgacatca tccatccgta ctgcctgtgg 360
accggccagc tggtgcgggc cggagtactg cgcccggtgc cgcccacggc cacgcggcag 420
atccgccggg acttcacccc ggcggccgtg gcggcgtcgt ccgtgcacgg cacgctctac 480
ggctacccca cggaggtgca gacctacgcg ctctactaca acaagcggct gctgcggcag 540
gccggtatcg acggaccgcc gggtacctgg caggagctgg aggacgcggc gtaccgcacc 600
gcccgccgcg accgccacgg caacatgctg gtgcagggct tcgggctgtc acgggccgac 660
gatgcgagcg tcgtggggca gacgctggcc ctgctggccg cgcgcggcgg cacattcctc 720
acctccgacg gacggcggac cgccatcggc tcggcggccg ggcgggatgt gctcgacctg 780
gagcgccggc tcatcgaccg cggcgccgcc gactccggta tctcgctcct gagggccttt 840
ccgtccggcc aggtggcgat ggcgatcaac gccggctggt ggacggcgag tctgcgcggc 900
gcgatggggg cggactaccg cgaggtcggg gtggcgccgg tgccggggcc cgcaccggac 960
gaccgcggca cgctcgccac gggcttcctg ctcggcgtga acgcgaagag cagatatccg 1020
ggggaggcct gggagttcct gcactggctc aacggtgtgc gggcgccggc cgcccggccg 1080
gggcgcagcg cgggaggagg cgtcccggtg tccaggatga gcgcgctcca ggtgtcggtc 1140
ggttcgatga ccgggcgggc ggacgatatg cgggcgctgc tgggaggcga cggcgagagg 1200
gacgccgacg gccgtggtgg cggcgaccgg aacctcggcc ccttcctgga cgcgctgcgc 1260
tacgccgtcc cggaaccgaa cggtccgcgc gcgcagcagg ccaaatcgct gctgcgcaag 1320
aacatcgagg acgtctggac gggccgggcc tcggtcgatg ccgcgctgcg caccgccggc 1380
cggcagatcg accaggaact gtcccggccc tactga 1416

<210> SEQ ID NO 8
<211> LENGTH: 912
<212> TYPE: DNA
<213> ORGANISM: Streptomyces hygroscopicus

<400> SEQUENCE: 8
atggcttcag ccggcggtgg tcccgtcagg gcggcccggc ggcggcagac cgccgtcgcc 60
tatctgttcc tgaccccggc cctgctgttc ttcgcggtct tcctcgccct gccgctgctg 120
ttcgccgtgc tgctcgcgca gtcgcgctgg gccggcttcg acctcgccga tatcgagccg 180
gtcgggatgg ccaacttcac cgacctcttc gcccgcggct cgaccttcct gacgcccgtc 240
ctcaccaata cgctgctgta cgccgtcggc accgtcgcga tcgccctcat cggcgcgctc 300
accctcgcga cctgcatcga caaccttcgt ttccaggggc tttggcggac cctctatttc 360
ctcccgatcg tgacgaccgt ggtcgccgtc ggcaacgtat ggaagtacat gtacgcaccg 420
ggcgggctga tcaacggagt gctcaacggt ctgggtctgc attccgtggc ctttctccag 480
gaccccggca cggcgctgcc gtccgtcgtc gtggtgcagg catgggcctc catgggaacc 540
gcgatcctga ttctcaccgc gggcctgaag tcgatccccg aggcctatta cgaggccgcc 600
gagctggacg gtgccggcgc cggcaccgtt ttccggcgca tcaccctgcc gctgctccgg 660
ccgtccctgc tcttcgtctg catcacccaa ttcatcaccg gattacagtc gttcgccctg 720
atcaatgtca tgacggacga cggcggaccg ggcgatgcga cgaatgtcgc ggccctggag 780
atgtatcagc aggcgttcag gtacggcgac tggggaatcg ccagtgccgc cgcctttgtg 840
ctgttcctgg tcattgtcgc gatcacggtg gggcagctct ggctgttccg ccggaaaggc 900

-continued

```
ggggaatcgt ga                                                           912

<210> SEQ ID NO 9
<211> LENGTH: 891
<212> TYPE: DNA
<213> ORGANISM: Streptomyces hygroscopicus

<400> SEQUENCE: 9

gtgagccggt ccgctcgtcg gcgcccgggc cgtcgccgcc cctggggctc gtacgccgtg      60

gtcgtcgccg gggccgccct caccctcgtc ccgttcctcg acatgctgct gacctcgttc     120

aaggggcccg gcgaatacgg gaaactcccc taccgattcc tcccccaggc gttcgacctt     180

tccaactacc gtgccgcgat ggagcagctg gatctgcccc tgcttttccg caacagcgtc     240

atcgccaccg ccgtcatcac cggatccatc ctggtgacct ccgcgctcgc cggatacgcg     300

ctggccaagc tgcgcttccc cggccgggag gtgatcttcc gcctggtcct gtccacgatg     360

atgttcccgc cgttcctctt cttcatcccg cactttctga tcctggtgca ctggcccggc     420

gccggcggca acgacctgct gggccgcggc ggggcgggcc tcaccgtgag ccttgcggcg     480

ctggtcatgc cgttcctcgt atccggtttc gggatctttc tgatgcggca attcatggtc     540

tccatcccgg acgaactgct ggaggcggcc cgtatcgacg gcgccggcga attcgccctc     600

tggtggcgca tcgtgctgcc ccagacgaaa ccggtggcgg tcaccctcgc gctgctcacc     660

ttcgtcaacg cctggaacga atacatctgg gcgctgctga tctccaccgc caatccgcgg     720

ctgatgacgc tgccggtggg catccagatg ctgcagagct atctcgaccc cgaccgtatg     780

gtcccggtca tgatggccgg cctggtgctg agcatcctgc cggtcctgct gctcttcctg     840

ctgctccaga agcactacct gcgcggggtg atgctcagcg gcctcaagtg a              891

<210> SEQ ID NO 10
<211> LENGTH: 1278
<212> TYPE: DNA
<213> ORGANISM: Streptomyces hygroscopicus

<400> SEQUENCE: 10

atgagttccg gtttctcctg ggctgttgtg gcaactgtgg tgagagtttc tgacccctca      60

ggaggaacca tggcttccga ctcgtcgtcc ccgacgccga tgccggccgt gtcgttgatc     120

gtgccgacgt tcaacgaggc agcgaacatt gatgagttgc tcgacggcgt gtgtgcggcg     180

atcccggcgg gtctggaggt cgaggtgctg ttcgtcgacg actcgacgga tgacacaccg     240

gaagtcatcg agaaggcggc cgcgcgctgt ccgatgccgg tgtcggtgct gcaccgggag     300

gttcccgaag gggggctcgg cggagcggtg gtggccggga tcgcccgtac gagtgcgccg     360

tggatcatgg tgatggacgc cgatctgcag catccgccgg agctgctgcc gcagttgatc     420

gaggctggtg agcgcgcggc ggccgagttg gtggtggcca gcagatacgc ggagggcggg     480

agccgtggcg ggctggccgg cgggtaccgg gtggccgtgt cgggggcgtc gaccgcgctg     540

accaagtcgc tgttcccccg gctgctgcgc ggggtctccg acccgatgag cgggtgcttc     600

gccatccggc gggaggcggt cgaccgcgcc gtacaggagg gcgagacccg gcaggaaggg     660

gggctgcggc cgctcggcta caagattctg ctggagctcg cggtgcgctg ccggccgcgc     720

ggggtggtgg aggtgccgta cgagttcggg gagcggttcg ccggcgagtc gaagtcgacg     780

gtgcgcgagg ggctgcggtt cctgcggcat ctggcggagc tgcggaccag cgacaagcgg     840

gcccggatgg tggccttcgg gctgatcggg gtgtcgggct tcgtaccgaa tctgctggcg     900

ctgtgggcgc tgaccggtgc cacgaccctg cattacgcgg tggcggaggt gctggccaat     960
```

-continued cagctcgggg tgctgtggaa cttcgccctg ctggacttcc tggtctaccg gagcgggaaa 1020
ccggggcgcg gggccggccg gctgctgggg ttcgcggcgc tcagcaacgc ggatctgctg 1080
gcgcggatcc cgttgatgat gctgttcgtg gagcaggccg ggatggggcc ggtgccggcg 1140
accgtgatca gtctcgtggt ggtgttcgcg ctgcggttcc tgctggtcga cacgttgatc 1200
taccggcgca agggggcggc tgccaagcgc gcggcggacg cggcggtcac cggcgggcag 1260
ggcgagcgcg ctgcttag 1278

<210> SEQ ID NO 11
<211> LENGTH: 1413
<212> TYPE: DNA
<213> ORGANISM: Streptomyces hygroscopicus

<400> SEQUENCE: 11
gtgaccgtcg tgctgctcgc cctgtccgac aggtacggct acaacgtcga cgagctgtat 60
ttccggctgc tcggcgaaca cggctgggcc tggggctaca ccgaccagcc gccgctggtg 120
ccggcgctgg tgcacgccac cgcccaggtc ctcggcgact cggtgtgggc gatccgggtg 180
ccggcggcgc tgtgcgcagg ggccgtggtg ctgctcgggg cgctgatcac cgccgaactc 240
ggcggcaccc gccgggcaca gactctttcc gccctgggtc tgggcagctc gttcctggtg 300
ctcagcgtcg gccacatcat ggtgaccacc accctggaca tgctcgcctg ggccgcggtg 360
ctgctcttcg tcctgcgggc gctgctgcgc tcggagggca agtggtggct gtgggcgggg 420
gtggtgctgg gcctggcgct gtacgccaag tacatcgtgg cgctgctgcc ggtggcgctg 480
ctggccgggc tcgcgctggt cggtccgcgg aaggtgttcc gtgaccggtg gctgtacgcg 540
gggatcgcgt tggcgctggc catcggctcg ccgaacctga tctaccaggc cacccatgac 600
ttcccgcagc tgcagatggc cgatgcgctg ggtgccaccg acggcccgat gaaccgggtc 660
atcttcgtgc cgagcctggt gatcctgctc ggtccggtgc tgaccgtggt gtgggtcgcg 720
gggctggtga agctgctgcg tgacccggca tggcggccgg tgcgggcgct ggcaccggcg 780
ttcgtggtcg gggtggcgct gaccctctac ggcggtggcc ggcccgacta cgtcggcggg 840
ttcctgatcg ggctgttcgc ggccggggcg gtggccgccg accggtggat ggggcggcgt 900
acgtcccggc gggtgctgct gtgcgccgga ctggccgcca gtgcggtgct ccaggtgctg 960
atggcgctgc cggtgctgcc gcagagctcc ccgttcgtgc cgctgaacaa catctccctg 1020
gagagcgtcg gctggccgcg gctcgccgag caggtgcgca cggcgtacga ggcgctgccg 1080
cggcagcagc gggagcgggc cgtggtgctc gccgacaacc tcggggagat cggcgcgctg 1140
gaccgctacg ggcacgggct gcccgcggtg ttcagcggcc acaacgaact gcacaagtgg 1200
ggcccgccgc cggagcgcgc cgatgtggtg gtcgcggtgg gcgtgccccg gtcccggctg 1260
gccgcggggt tcacctcgtg caccgtcgtg ggacgggtcg acaacggcgt cggcgtcgag 1320
aacgccgagc agggcagacc gatcacggtg tgccacggcc gcaaggcttc ctgggcccga 1380
ctgtggccct cctaccacta cttgagcggc tga 1413

<210> SEQ ID NO 12
<211> LENGTH: 1530
<212> TYPE: DNA
<213> ORGANISM: Streptomyces hygroscopicus

<400> SEQUENCE: 12
atgacgacat ccctcgacag ggattccagg gcggccgcgg ccgggccggg ggtgttccgc 60

-continued

```
ccggcgccga tggcgtggcg gccggtcgcc gtggtggtgg ccgcgctggc cgtgctgttg     120

ttcgccttcg ccggcgaata cggctaccac gccgacgagt tgtacttccg gctgctcggg     180

gtgcacggct tcgcctgggg ctatgtggac cagccgccgc tgctgccact ggccgtacgg     240

acctcgatgg agatcttcgg cgacagcatg tgggcgatcc gggtgcccgc cgtgctgtgc     300

gcggcggccg tgaccgcgct cggcgcgatg atcgccgccg agctgggcgg ttcccggcgg     360

gcccagacgc tgaccgcgtt cggggtggcc acctcgacga tggtgctcag cttcggccac     420

tggatcctca ccaccagctt cgacaccgtg gcgtgggccg cggtgctgct gttcgtgatg     480

cgggtgctgc tgcgcggcga gagcaagtgg tggctgtggg ccggggtggt ggtcggtgtc     540

gcgctgtacg ccaagtacat cgtgctgctg ctgccggtgg cgctgctggt ggggctggcg     600

ctggtcggtc cgcggaaggt cttccgcgac gggaagctgt acgcgggcac ggcgctggcg     660

ctggtcatcg gctcgccgaa cctgatctac caggccaccc atgacttccc gcagctgcag     720

atggcggagg ggctggcggg caccgacggc gaggcgaacc gcgccatgtt cgccacgaac     780

ctgatcctgc tgttcggccc cgcgctgttc gtgctgtgca tgatcgggct ggtcaagctg     840

ttccgggtgc cggagtggaa gcccgtacgg acactggccg tcggctatct cgcggccacc     900

gcggcgtcgt acctcatcga gggcggccgg ccggactaca ccggcggact gctgatcgcg     960

ctgctggccg ccgggtgtgt gacggccgac cggtgggcgg gcgcccgcaa gctgcggctc    1020

tcggtgctcg cggtctcgct gacgctcagc accgcggtgc agatgctgct gtcgctgccg    1080

gtgatcccca agagctcgct gcgcgacttc cagatcgcca gcatggcgct ggagacggtg    1140

ggctggcccc gtctggtcca gcagaccgag gcggcctacc gcgcactgcc ggccgcggac    1200

cgcgaccgcg cgatcgtgct caccgagaac ttcggcgagg cgggcgccct ggaccactac    1260

gggcacgggc tgccgaaggt gtacagcggc cacaacgagc tgtaccactg gggcccgccg    1320

ccgcagcgcg ccgaggtggt ggtcgcggtg ggcatcgacc ggaaccggct gtccgccgac    1380

ttcaccagct gcaaggtcgt cgaccacatc gacaaccgcc tgggcatcga caatccggaa    1440

cagggcgtgc cgatcacggt gtgccacggc cccaagaagc cctggtccgc gctgtggccg    1500

acctaccggc actacaacgc ctatctgtag                                     1530
```

<210> SEQ ID NO 13
<211> LENGTH: 1014
<212> TYPE: DNA
<213> ORGANISM: Streptomyces hygroscopicus

<400> SEQUENCE: 13

```
atgagtaccg aggtttccga ggcgcaggcg cgacgcgccg tggcagacat cttcaactcg      60

acgctggctt cttcggccat cggcgccgcg tgggagctcg gagctcttga cgagctgcgg     120

gagaacggca agttggatgt ctccgatttc gccgtacgcc atgatctgca cgagccggcg     180

gtggtcggca tgttcaccgc gctggcgagt gtgggaatcg tgcggcgcga gggcgccacc     240

gtcgtcgtcg gcccgtactt cgacgaggcc aatcaccacc gttcactgtt ccactggctc     300

aatcagggca gcggcgagct cttccgccgc atgccgcagg tgctgccgaa cgagaaccgc     360

acaggaaagt tctaccagcg ggacgcgggg gcgatcagct acgcgtgccg cgagatcagc     420

gagcgctatt tcgacccggc gttctgggcc gcggtcgacg gtctgggtta cacccccacc     480

accgtcgccg acctggggtc cggcagcggt gagcggctga tccagatcgc ccggcggttc     540

cccggcgtcc gcggcctcgg cgtggacatc gccgacggcg cgatcgccat ggcggagaag     600

gaggtggccg ccaagggatt cggcgaccag atctccttcg tgcggggcga cgcgcgcacc     660
```

-continued atcgaccagg tctcggcgcg cggggaattc gccgaggtcg atctgctcac ctgcttcatg 720
atggggcacg acttctggcc ccgcgagaac tgtgtgcaga cgctgcgaaa gctgcgcgcg 780
gcattcccga atgtgcgccg gttcctgctc ggcgacgcca cccgcaccgt cggtatcccc 840
gaccgcgaac tccccgtatt caccctggga ttcgagttcg ggcacgacat gatgggcgtt 900
tacctgccga ccctcgatga atgggacggg gtattcgaag agggtggctg gcgctgtgtg 960
aagaagcacg ccatcgactc gctgtcggtc tccgtggtct tcgaactcga gtaa 1014

<210> SEQ ID NO 14
<211> LENGTH: 1320
<212> TYPE: DNA
<213> ORGANISM: Streptomyces hygroscopicus

<400> SEQUENCE: 14
atggaccacg aaagcctgca cagcaccctg accgaactgg cggcccgcca tcgggtgccc 60
ggcgcgcagc tcgccgtcat ccacgagggg gaacggttcc tggtgcacac cggagtgtgt 120
gacaccgcct ccggagcccc cgtggagcgg cacaccgcct tccccgtcgg ctcgctgacc 180
aagccgttca ccgccgccct cgcgatgatc ctggtggccg acggggacgt ggacctggac 240
gagccgctga gggggcagct gccggagttc ggggcgggcg aactcgtcac cctccggcag 300
ttgctcagcc acacctcggg cctgccctcc gatgtgccgg agggcagcga cgaggccggc 360
ggcggcgacc gtgcccgctg ggtggcccgg tactgccgta cggcggatct cacgcatgcg 420
cccgggacgg tcttctcgta ctccaacatc ggctatgtcg tcgtgggccg gctcatcgag 480
gcggtcaccg gcatgagctg gcaggaggcg atcagcgcga tcctgctcga acccctgggc 540
acccggcccg cgttcgtcgt cggagccccc gccacccgtc cggtggccac cgggcacgcc 600
gtccaggcgg tccgcgaccg ggtggtgccg ataccggacc aggatcttcc cgaggtcgag 660
atgcccaacg ggcgctggc gctgagcgcc gaggacctgg tcggcttcgc ccggctgtac 720
ttcgccggct gcccggaccc tcagccgctg gaccgggcga ccgccgacga catgtgcttc 780
gaccagctgg cctcgatcgc catcggcccg tacggcatgg ccgacggctg gggcctgggc 840
tgggcgaggt tcgacgacgg tgcggcggac gtctacggcc acaacggcac cggcgacggc 900
acctcctgtc atctgcgctt cgacccggcc aacggctccg cggtcgcgct gaccgccaac 960
gccaacaccg gcgcccagct gtgggacgcc ctggtgcccc ggctgcgggc catgggtctg 1020
gcggtcggcg accgcccggc gcccgagccg cccaccaccc cgccgccggt cccggacgac 1080
tgtccgggcc gctacaccaa cggcgacacc gagttcgtgg tgcagcccgg cgccgacggc 1140
gggctgctgc tgagcttcgg cggggcgccg cactcggagc tgctgtgctc ccccgatctg 1200
cgcttcacca tgcgggagct gggcagcggt gcccggtccc cgggccgctt cgtgaccgat 1260
cccgccaccg ggcggatcgg ctacctccag atcaccgggc gactcgcccc ccgacgctga 1320

<210> SEQ ID NO 15
<211> LENGTH: 1353
<212> TYPE: DNA
<213> ORGANISM: Streptomyces hygroscopicus

<400> SEQUENCE: 15
atgaccacgg cccccacgga cgcggagacg gcacgcggca gcgcggccgt cccgctgtcc 60
cgcaaccgcg actacaacat cctgtggtcc agccagctga tgtccgaact cgccatggag 120
atggccgcgg tagccgtgcc gctgctgatc ctcgcccggc acggctcacc gctccagctg 180

-continued

```
ggcctggcct cctccgcgat ggcggccgcg cacatgatct cggtggtgcc ggccggggtg    240

atcgcggacc gctgggaccg ccgccggctg atgctgggct gccaggtgct acgggtgctg    300

ggcatggtga gcctggccgg cgcgctgctg ctggaccggt acgcgttctg gcatgtgctg    360

ctggtcgtgg tgctggaggg cttcctcggc tcggtcttcg accccgcgga acatgccgcg    420

ctgccccagg tggtgccgcc cgaccagctc tccacggcgg tggccagaaa cgcggcgcgc    480

ccctacatcg ccaccctcgt ggggccgggc gtcgccggtt tcctcttcag cgccctgccg    540

ctcgggccgt tcgcgaccaa tgcggtgatg ttcgcgctgt cgtccgtggc gctgtgcttt    600

ctgcggctgc cccgggggcg gtccgccgtg gtccggaccg gcgacgggcc cgacagcgcc    660

ggagcggacc acgacaggcc ggaccacgac ggacgggacg acgcgaacga cgacactgcg    720

ccgcggcccg gggcgccgc ccaggacttc gctgccggct tccgctgggt gctggggcag    780

ccggtgatcc gcaccacgat ggcctggatg atgatcacga acctggtctt cagctcgctg    840

ctgatcgtgc tgctcgcgct ctcgggcgag gacaaggtcg gcgccggtga gctgggtctg    900

acgatggcct gcttcggcgc cggcggactg ctcggcgggc tcttcgcggc ccggatgcac    960

gccgccgccc ggccaccggt gatcctcctc ggcttcacct ggaccgccgc cctgggcgcc   1020

gccctgatgg cggtggtgcc caccggtctg ccccagggag cgctgctcgg cctgatggcg   1080

ctcttcgccc cgctcgccaa caccaccgtg ctgacctacc agttgaccgt caccccggac   1140

gagctgcggg gccggatgag cggcgtcgcc gggttctgct cggggggcgc cggtgtcctg   1200

gggcccgcgc tcggcggtgc gctgacgggg gcggccggcg ggggcgtgac ccccgtactc   1260

atctgcgccg gctgcctggt cctggtcgct gtcgcggcca ccgcgagccc cacgctgcgg   1320

cggtttcccg acatcgcgga ccggcagccc tga                                1353
```

<210> SEQ ID NO 16
<211> LENGTH: 1227
<212> TYPE: DNA
<213> ORGANISM: Streptomyces hygroscopicus

<400> SEQUENCE: 16

```
atgcagaccc cccacacacc gagccaggca cagtcccagc cacggcaaaa gccgcagccg     60

ccgtcgcagt cgcagtcgca gtcgcagccg aatctgaggt ccctgaccgg attacggttc    120

ctgggcttat tacccgtctt cctcacccat gccgcgttcg agggcgtctt cagcgacgcg    180

gacgtgagct ggggcttcct cgacgcgatg gggaacaccg gctatgccgc ggtctcgttc    240

ttcttcgtgc tgagcggctt tgtgatcacc tggtcctacc gctcccgcga caccacccgc    300

acgttctggc gccgacgcgc cttccgggtc ttccccaacc atctcgtggc ctatgtgttc    360

gcgctggctc tgatgctcgc ggcgggcgcc gccttcgacg cccccgccct gatctcccag    420

atgttcctgg tgcacgcatg ggtgcccgac ccgctgttca tcgacaccgg caacacggtg    480

acctggtccc tcggggtcga tgtggtgttc tacgggctct tcccggtgct gctcgtgctg    540

gtgaacaaga tcaagccaac ccgtttgtgg tactgggccg gtgctgccgt gctcatggtg    600

atcgccatcc ccacagtggc gctgaccctg ctcccggaca ccccggccat gtcggtgggc    660

gatgtctccc gcagccagta ctggttcacc tacttcttcc cgctctcccg aaccgtggag    720

tgcgtgctgg gcatgctgat ggcgcggatc gtgctgtccg gcaagtggat aggcctgcgg    780

gtgctgcccg cctcggccct ggtggtcgtg gggtatgtcg tcgcacagca actcccccttc   840

ctctaccggc tcagcgcggt gctgatcgtg ccgatcgtgc tgctcaccgc ctccgtggcg    900

gtggccgacg ccgagggccg ggggaccccg ctcggcggca aggtcatggt ccggctcggt    960
```

-continued

```
gaactctcct tcgccttcta cctcgtgcac caggcgctcc tggcgtacgg gcacatcctg   1020

atcagcccga agaacgccca gggcgaggtg ctgccccgta cctgggacac gcctggcggc   1080

atcgcggtga tcgtcctgtc gttcgtggtg tccctgggac tcgcgtggct gctgcacaac   1140

ggggtggaga agccggtgat gcgccgttgg tcccggtcca ggcgccgcgt cacccagcag   1200

ccgccggcaa aggtgccggc aacttag                                       1227
```

```
<210> SEQ ID NO 17
<211> LENGTH: 1371
<212> TYPE: DNA
<213> ORGANISM: Streptomyces hygroscopicus

<400> SEQUENCE: 17

gtgtggagtg cgcgaaagat ctcggccaaa ctccggcgca acgggggagt aaggctgacc     60

gctgccagaa gtccgcgcgc gccgtggatg tccggtgccg gcgaccacgc ccggatcatc    120

catcagccga cagtggtgcg gccgccgttg cggcgcaccg agccgcaccg cctgtcgcgc    180

atctggcgag aggtccgcat gcagacaaga caatccaacc cgaacctgag atccctgacc    240

ggtttgcggt tcgtggcgat gctgccggtc ttcctcaccc atgcggcgtt cgagggcgtc    300

ttcagcgacg cgaaggtgag ctggggcttc ctcgacgcga tggggagcac cggctatatg    360

gccgtctcgt tcttcttcgt gctcagcggc tttgtgatca cgtggtcgta ccggcccacc    420

gacaccgcgc gcaagttctg gcgccggcgc ttcttccggg tcttccccaa ccacgtcgtg    480

acctatgcgc tcgccctcgg gctgatcgct gcggtggggc tgagtgtcgg cgtactgccc    540

tcggtcaccc agctcttcct cgtccagtcc tgggtgcccg acccggcgtt caccgacacc    600

ggcaacagcg tgagctggtc gctcgcggtg gatgtggtgt tctacgcgct cttcccggtg    660

ctgctcacgc tggtgaacaa gatcaagccg aatcggctct ggtactgggt cggtggctcc    720

gtcatcggtg tggccgtggt accggccatc gcgctcgccg cgctcccgag cacccccgag    780

atgccgctcg gcggggtgtc cgtcagccag tactggttca cctacttctt cccgctcttc    840

cggctgctgg agtgtgtgct cggcatgctg atggcgcgga tcgtgctgtc cggcaagtgg    900

atacgcctgc gggtgctgcc cgccgccgtc ctcgtggtga tcgcgtacta cttcgcccag    960

caggtcccgt acctctaccg gctgagtgcg gtgacggtgc tgccggtcgc gctgctgacg   1020

gcggcggccg cggtggcgga ctccgagggc cggggcaccc tgttcggcag caaggtcatg   1080

gtctggttcg gcgaactctc cttcgccttc tacctgctgc acaacctcgt cctgaagtac   1140

ggccatctgc tgctcggcca caccgaggag gagggcgagc tggtgggcca cacctggggc   1200

gtgcccgagg gaatcgccct gatcgccgcc gccttcgcgg tgtccctgct gctggcctgg   1260

ctgctgcaca acggagtgga gaagcaggcg atgcgccgct ggtcccgacg caagccggct   1320

ccagtggctg aagtaaccag tgggttctat gcgaaggacg gggcaattta g            1371
```

```
<210> SEQ ID NO 18
<211> LENGTH: 1026
<212> TYPE: DNA
<213> ORGANISM: Streptomyces hygroscopicus

<400> SEQUENCE: 18

gtgctgacgc tccacctgca ggatgacgac gtcgccgcga tcgacgctgt ggctgacgaa     60

ctcagccggc gatacgactc cgtggagtcc acggagttcc aggccgagag ccgcctctac    120

gcggacgagt tgccacgtcg cgtgcgacga gcgctgcacg aataccgcag caccgagaag    180
```

-continued

```
tccggcatcc tggtcgtcac cggcctgccc gtggacgact cggcgctcgg ggcgaccccg    240

gccgaccgcc ggcacaagcc ggtgccgtcc acgtcactgc gccaggacat cgccttctac    300

ctcatagcca atctgctggg cgaccccatc ggctgggcca cccagcagga cggcttcatc    360

atgcatgacg tctaccccgt ccagggcttc gagcacgaac agatcggctg gggcagcgag    420

gagacgctca cctggcacac cgaggacgcc ttccatccgc tgcgcacgga ctatctcgga    480

ctgatgtgtc tgcgcaatcc ggacggcgtc gagaccaccg cctgcgatat cgccgatgtc    540

gagatcgacg acgagacccg ggagaccctc tcgcaggagc gcttccggat cctgccggac    600

gacgcgcacc gcatccacgg caaggccccg ggggacgaga gcgcacgcga gagtgcgctg    660

cgtgagcgca gccggcagcg ggtggcctcg gccctggagt cgcccgaccc ggtggccgtg    720

ctcttcgggg accgcgacga cccgtatctg cggatcgacc cgcactacat gcagggcgtc    780

cagggcgaga ccgagcagcg ggcgctggag accatcggcg ccgcgatcga cgacgccatg    840

tccggtgtcg tgctcagccc cggtgacatc gttttcatcg acaactaccg cgtcgtccac    900

ggacgtaagc cgttccgtgc ccgcttcgac ggtacggacc gctggctgcg gcggctcaac    960

atcgcccggg acctgcgcaa gtcgcgcgag gccaggctcg ccgccaccac ccgcgtcatc   1020

tactga                                                              1026
```

<210> SEQ ID NO 19
<211> LENGTH: 28
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (1)..(32)
<223> OTHER INFORMATION: where n is inosine

<400> SEQUENCE: 19

```
acstcsggcw cgcaccggcc ngccsaag                                        28
```

<210> SEQ ID NO 20
<211> LENGTH: 32
<212> TYPE: DNA
<213> ORGANISM: Artificial Sequence
<220> FEATURE:
<223> OTHER INFORMATION: PCR primer

<400> SEQUENCE: 20

```
agctcsaysc gstagccscg saycttsacc tg                                   32
```

<210> SEQ ID NO 21
<211> LENGTH: 323
<212> TYPE: PRT
<213> ORGANISM: Streptomyces hygroscopicus

<400> SEQUENCE: 21

```
Met Ser Ala Thr Pro Arg Pro Arg Pro Val Leu Arg Pro Phe Arg Pro
1               5                   10                  15

Gly Asp Gly Arg Ser Leu Leu Ala Ala Trp Cys Arg Ser Ala Pro Asp
            20                  25                  30

Asp Pro Ile Thr Ala Ala Arg Phe Arg Thr Leu Ile Leu Leu Asp Pro
        35                  40                  45

Asn Phe Asp Pro Glu Gly Leu Arg Val Ala Asp Leu Asp Gly Gln Val
    50                  55                  60

Val Gly Ala Val Tyr Ala Val Arg Arg Arg Thr Pro Leu Ala Gly Thr
```

-continued 65 70 75 80

Asp Leu Glu Pro Asp Val Gly Trp Ile Leu Phe Phe Phe Val Asp Pro
85 90 95

Pro His Arg Arg Thr Gly Leu Gly Arg Arg Leu Leu Thr Asp Ala Leu
100 105 110

Asp Trp Leu Arg Gly His Gly Arg Thr Arg Val Asp Phe Ala Pro Tyr
115 120 125

Ala Pro His Tyr Val Leu Pro Gly Leu Asp Arg Ala Ala Tyr Pro Glu
130 135 140

Ala Ala Arg Leu Leu Ala Ser Leu Gly Phe Arg Pro Arg Tyr Glu Ala
145 150 155 160

Ala Ala Met Asp Arg Gly Leu Val Gly Tyr Arg Met Pro Asp Glu Val
165 170 175

Arg Arg His Glu Ala Ala Leu Thr Ala Arg Gly His Arg Phe Gly Thr
180 185 190

Pro Ser Asp Asp Asp Leu Val Asp Leu Leu Gly Leu Ala Glu Glu Phe
195 200 205

Thr Pro Asp Trp Ala Arg Ala Ile Arg Gln Cys Leu Thr Gly Gly Ala
210 215 220

Pro Leu Asp Arg Ile Val Ser Ala Arg Ala Pro Asp Gly Arg Met Ala
225 230 235 240

Gly Trp Ala Met His Gly Ala Tyr Asp Gly Thr Ala Glu Arg Phe Gly
245 250 255

Pro Phe Gly Val Arg Lys Glu Leu Arg Gly Ala Gly Leu Gly Lys Val
260 265 270

Leu Leu His Leu Thr Leu Glu Arg Met Arg Ala Leu Gly Val His Gly
275 280 285

Ala Trp Phe Leu Trp Thr Gly Glu Gln Ser Pro Ala Gly His Leu Tyr
290 295 300

Arg Ala Ser Gly Phe Thr Thr Thr Arg Arg Phe Thr Val Leu Arg Trp
305 310 315 320

Glu Ala Gly

<210> SEQ ID NO 22
<211> LENGTH: 471
<212> TYPE: PRT
<213> ORGANISM: Streptomyces hygroscopicus

<400> SEQUENCE: 22

Met Arg Arg Arg Thr Phe Thr Ala Gly Ala Ala Ala Gly Ala Ala Leu
1 5 10 15

Leu Ala Gly Ala Gly Cys Asp Ala Pro Gly Gly Ala Gly His Gly Asp
20 25 30

Gly Glu His Gly Asp Gly Asp Gly Gly Asp Gly Arg Gly Ser Gly Gly
35 40 45

Arg Arg Gly Ala Pro Val Thr Leu Thr Val Leu Thr His Tyr Ala Ser
50 55 60

Glu Pro Leu Ala Ser Ala Leu Gln Thr Val Val Asp Ala Trp Asn Ala
65 70 75 80

Thr His Arg Arg Ile Thr Val Arg Thr Ala Ala Val Lys Phe Pro Asp
85 90 95

Leu Leu Thr Thr Tyr Met Val Arg Gln Ala Ala Gly Gln Gly Ala Asp
100 105 110

Ile Ile His Pro Tyr Cys Leu Trp Thr Gly Gln Leu Val Arg Ala Gly

-continued

```
        115                 120                 125

Val Leu Arg Pro Val Pro Pro Thr Ala Thr Arg Gln Ile Arg Arg Asp
    130                 135                 140

Phe Thr Pro Ala Ala Val Ala Ala Ser Ser Val His Gly Thr Leu Tyr
145                 150                 155                 160

Gly Tyr Pro Thr Glu Val Gln Thr Tyr Ala Leu Tyr Tyr Asn Lys Arg
            165                 170                 175

Leu Leu Arg Gln Ala Gly Ile Asp Gly Pro Pro Gly Thr Trp Gln Glu
        180                 185                 190

Leu Glu Asp Ala Ala Tyr Arg Thr Ala Arg Arg Asp Arg His Gly Asn
        195                 200                 205

Met Leu Val Gln Gly Phe Gly Leu Ser Arg Ala Asp Asp Ala Ser Val
    210                 215                 220

Val Gly Gln Thr Leu Ala Leu Leu Ala Ala Arg Gly Gly Thr Phe Leu
225                 230                 235                 240

Thr Ser Asp Gly Arg Arg Thr Ala Ile Gly Ser Ala Ala Gly Arg Asp
            245                 250                 255

Val Leu Asp Leu Glu Arg Arg Leu Ile Asp Arg Gly Ala Ala Asp Ser
            260                 265                 270

Gly Ile Ser Leu Leu Arg Ala Phe Pro Ser Gly Gln Val Ala Met Ala
        275                 280                 285

Ile Asn Ala Gly Trp Trp Thr Ala Ser Leu Arg Gly Ala Met Gly Ala
    290                 295                 300

Asp Tyr Arg Glu Val Gly Val Ala Pro Val Pro Gly Pro Ala Pro Asp
305                 310                 315                 320

Asp Arg Gly Thr Leu Ala Thr Gly Phe Leu Leu Gly Val Asn Ala Lys
            325                 330                 335

Ser Arg Tyr Pro Gly Glu Ala Trp Glu Phe Leu His Trp Leu Asn Gly
            340                 345                 350

Val Arg Ala Pro Ala Ala Arg Pro Gly Arg Ser Ala Gly Gly Gly Val
        355                 360                 365

Pro Val Ser Arg Met Ser Ala Leu Gln Val Ser Val Gly Ser Met Thr
    370                 375                 380

Gly Arg Ala Asp Asp Met Arg Ala Leu Leu Gly Gly Asp Gly Glu Arg
385                 390                 395                 400

Asp Ala Asp Gly Arg Gly Gly Gly Asp Arg Asn Leu Gly Pro Phe Leu
            405                 410                 415

Asp Ala Leu Arg Tyr Ala Val Pro Glu Pro Asn Gly Pro Arg Ala Gln
            420                 425                 430

Gln Ala Lys Ser Leu Leu Arg Lys Asn Ile Glu Asp Val Trp Thr Gly
        435                 440                 445

Arg Ala Ser Val Asp Ala Ala Leu Arg Thr Ala Gly Arg Gln Ile Asp
    450                 455                 460

Gln Glu Leu Ser Arg Pro Tyr
465                 470


<210> SEQ ID NO 23
<211> LENGTH: 303
<212> TYPE: PRT
<213> ORGANISM: Streptomyces hygroscopicus

<400> SEQUENCE: 23

Met Ala Ser Ala Gly Gly Gly Pro Val Arg Ala Ala Arg Arg Arg Gln
1               5                   10                  15
```

-continued

```
Thr Ala Val Ala Tyr Leu Phe Leu Thr Pro Ala Leu Leu Phe Phe Ala
            20                  25                  30

Val Phe Leu Ala Leu Pro Leu Leu Phe Ala Val Leu Leu Ala Gln Ser
        35                  40                  45

Arg Trp Ala Gly Phe Asp Leu Ala Asp Ile Glu Pro Val Gly Met Ala
    50                  55                  60

Asn Phe Thr Asp Leu Phe Ala Arg Gly Ser Thr Phe Leu Thr Pro Val
65                  70                  75                  80

Leu Thr Asn Thr Leu Leu Tyr Ala Val Gly Thr Val Ala Ile Ala Leu
                85                  90                  95

Ile Gly Ala Leu Thr Leu Ala Thr Cys Ile Asp Asn Leu Arg Phe Gln
            100                 105                 110

Gly Leu Trp Arg Thr Leu Tyr Phe Leu Pro Ile Val Thr Thr Val Val
        115                 120                 125

Ala Val Gly Asn Val Trp Lys Tyr Met Tyr Ala Pro Gly Gly Leu Ile
    130                 135                 140

Asn Gly Val Leu Asn Gly Leu Gly Leu His Ser Val Ala Phe Leu Gln
145                 150                 155                 160

Asp Pro Gly Thr Ala Leu Pro Ser Val Val Val Val Gln Ala Trp Ala
                165                 170                 175

Ser Met Gly Thr Ala Ile Leu Ile Leu Thr Ala Gly Leu Lys Ser Ile
            180                 185                 190

Pro Glu Ala Tyr Tyr Glu Ala Ala Glu Leu Asp Gly Ala Gly Ala Gly
        195                 200                 205

Thr Val Phe Arg Arg Ile Thr Leu Pro Leu Leu Arg Pro Ser Leu Leu
    210                 215                 220

Phe Val Cys Ile Thr Gln Phe Ile Thr Gly Leu Gln Ser Phe Ala Leu
225                 230                 235                 240

Ile Asn Val Met Thr Asp Asp Gly Gly Pro Gly Asp Ala Thr Asn Val
                245                 250                 255

Ala Ala Leu Glu Met Tyr Gln Gln Ala Phe Arg Tyr Gly Asp Trp Gly
            260                 265                 270

Ile Ala Ser Ala Ala Ala Phe Val Leu Phe Leu Val Ile Val Ala Ile
        275                 280                 285

Thr Val Gly Gln Leu Trp Leu Phe Arg Arg Lys Gly Gly Glu Ser
    290                 295                 300


<210> SEQ ID NO 24
<211> LENGTH: 296
<212> TYPE: PRT
<213> ORGANISM: Streptomyces hygroscopicus

<400> SEQUENCE: 24

Val Ser Arg Ser Ala Arg Arg Arg Pro Gly Arg Arg Arg Pro Trp Gly
1               5                   10                  15

Ser Tyr Ala Val Val Val Ala Gly Ala Ala Leu Thr Leu Val Pro Phe
            20                  25                  30

Leu Asp Met Leu Leu Thr Ser Phe Lys Gly Pro Gly Glu Tyr Gly Lys
        35                  40                  45

Leu Pro Tyr Arg Phe Leu Pro Gln Ala Phe Asp Leu Ser Asn Tyr Arg
    50                  55                  60

Ala Ala Met Glu Gln Leu Asp Leu Pro Leu Leu Phe Arg Asn Ser Val
65                  70                  75                  80

Ile Ala Thr Ala Val Ile Thr Gly Ser Ile Leu Val Thr Ser Ala Leu
                85                  90                  95
```

-continued

Ala Gly Tyr Ala Leu Ala Lys Leu Arg Phe Pro Gly Arg Glu Val Ile
100 105 110

Phe Arg Leu Val Leu Ser Thr Met Met Phe Pro Pro Phe Leu Phe Phe
115 120 125

Ile Pro His Phe Leu Ile Leu Val His Trp Pro Gly Ala Gly Gly Asn
130 135 140

Asp Leu Leu Gly Arg Gly Gly Ala Gly Leu Thr Val Ser Leu Ala Ala
145 150 155 160

Leu Val Met Pro Phe Leu Val Ser Gly Phe Gly Ile Phe Leu Met Arg
165 170 175

Gln Phe Met Val Ser Ile Pro Asp Glu Leu Leu Glu Ala Ala Arg Ile
180 185 190

Asp Gly Ala Gly Glu Phe Ala Leu Trp Trp Arg Ile Val Leu Pro Gln
195 200 205

Thr Lys Pro Val Ala Val Thr Leu Ala Leu Leu Thr Phe Val Asn Ala
210 215 220

Trp Asn Glu Tyr Ile Trp Ala Leu Leu Ile Ser Thr Ala Asn Pro Arg
225 230 235 240

Leu Met Thr Leu Pro Val Gly Ile Gln Met Leu Gln Ser Tyr Leu Asp
245 250 255

Pro Asp Arg Met Val Pro Val Met Met Ala Gly Leu Val Leu Ser Ile
260 265 270

Leu Pro Val Leu Leu Leu Phe Leu Leu Leu Gln Lys His Tyr Leu Arg
275 280 285

Gly Val Met Leu Ser Gly Leu Lys
290 295

<210> SEQ ID NO 25
<211> LENGTH: 425
<212> TYPE: PRT
<213> ORGANISM: Streptomyces hygroscopicus

<400> SEQUENCE: 25

Met Ser Ser Gly Phe Ser Trp Ala Val Val Ala Thr Val Val Arg Val
1 5 10 15

Ser Asp Pro Ser Gly Gly Thr Met Ala Ser Asp Ser Ser Ser Pro Thr
20 25 30

Pro Met Pro Ala Val Ser Leu Ile Val Pro Thr Phe Asn Glu Ala Ala
35 40 45

Asn Ile Asp Glu Leu Leu Asp Gly Val Cys Ala Ala Ile Pro Ala Gly
50 55 60

Leu Glu Val Glu Val Leu Phe Val Asp Asp Ser Thr Asp Asp Thr Pro
65 70 75 80

Glu Val Ile Glu Lys Ala Ala Ala Arg Cys Pro Met Pro Val Ser Val
85 90 95

Leu His Arg Glu Val Pro Glu Gly Gly Leu Gly Gly Ala Val Val Ala
100 105 110

Gly Ile Ala Arg Thr Ser Ala Pro Trp Ile Met Val Met Asp Ala Asp
115 120 125

Leu Gln His Pro Pro Glu Leu Leu Pro Gln Leu Ile Glu Ala Gly Glu
130 135 140

Arg Ala Ala Ala Glu Leu Val Val Ala Ser Arg Tyr Ala Glu Gly Gly
145 150 155 160

Ser Arg Gly Gly Leu Ala Gly Gly Tyr Arg Val Ala Val Ser Gly Ala

-continued

```
                165                 170                 175

Ser Thr Ala Leu Thr Lys Ser Leu Phe Pro Arg Leu Leu Arg Gly Val
            180                 185                 190

Ser Asp Pro Met Ser Gly Cys Phe Ala Ile Arg Arg Glu Ala Val Asp
        195                 200                 205

Arg Ala Val Gln Glu Gly Glu Thr Arg Gln Glu Gly Gly Leu Arg Pro
    210                 215                 220

Leu Gly Tyr Lys Ile Leu Leu Glu Leu Ala Val Arg Cys Arg Pro Arg
225                 230                 235                 240

Gly Val Val Glu Val Pro Tyr Glu Phe Gly Glu Arg Phe Ala Gly Glu
                245                 250                 255

Ser Lys Ser Thr Val Arg Glu Gly Leu Arg Phe Leu Arg His Leu Ala
            260                 265                 270

Glu Leu Arg Thr Ser Asp Lys Arg Ala Arg Met Val Ala Phe Gly Leu
        275                 280                 285

Ile Gly Val Ser Gly Phe Val Pro Asn Leu Leu Ala Leu Trp Ala Leu
    290                 295                 300

Thr Gly Ala Thr Thr Leu His Tyr Ala Val Ala Glu Val Leu Ala Asn
305                 310                 315                 320

Gln Leu Gly Val Leu Trp Asn Phe Ala Leu Leu Asp Phe Leu Val Tyr
                325                 330                 335

Arg Ser Gly Lys Pro Gly Arg Gly Ala Gly Arg Leu Leu Gly Phe Ala
            340                 345                 350

Ala Leu Ser Asn Ala Asp Leu Leu Ala Arg Ile Pro Leu Met Met Leu
        355                 360                 365

Phe Val Glu Gln Ala Gly Met Gly Pro Val Pro Ala Thr Val Ile Ser
    370                 375                 380

Leu Val Val Val Phe Ala Leu Arg Phe Leu Leu Val Asp Thr Leu Ile
385                 390                 395                 400

Tyr Arg Arg Lys Gly Ala Ala Ala Lys Arg Ala Ala Asp Ala Ala Val
                405                 410                 415

Thr Gly Gly Gln Gly Glu Arg Ala Ala
            420                 425


<210> SEQ ID NO 26
<211> LENGTH: 470
<212> TYPE: PRT
<213> ORGANISM: Streptomyces hygroscopicus

<400> SEQUENCE: 26

Val Thr Val Val Leu Leu Ala Leu Ser Asp Arg Tyr Gly Tyr Asn Val
1               5                   10                  15

Asp Glu Leu Tyr Phe Arg Leu Leu Gly Glu His Gly Trp Ala Trp Gly
            20                  25                  30

Tyr Thr Asp Gln Pro Pro Leu Val Pro Ala Leu Val His Ala Thr Ala
        35                  40                  45

Gln Val Leu Gly Asp Ser Val Trp Ala Ile Arg Val Pro Ala Ala Leu
    50                  55                  60

Cys Ala Gly Ala Val Val Leu Leu Gly Ala Leu Ile Thr Ala Glu Leu
65                  70                  75                  80

Gly Gly Thr Arg Arg Ala Gln Thr Leu Ser Ala Leu Gly Leu Gly Ser
                85                  90                  95

Ser Phe Leu Val Leu Ser Val Gly His Ile Met Val Thr Thr Thr Leu
            100                 105                 110
```

-continued

```
Asp Met Leu Ala Trp Ala Ala Val Leu Leu Phe Val Leu Arg Ala Leu
        115                 120                 125

Leu Arg Ser Glu Gly Lys Trp Trp Leu Trp Ala Gly Val Val Leu Gly
    130                 135                 140

Leu Ala Leu Tyr Ala Lys Tyr Ile Val Ala Leu Leu Pro Val Ala Leu
145                 150                 155                 160

Leu Ala Gly Leu Ala Leu Val Gly Pro Arg Lys Val Phe Arg Asp Arg
                165                 170                 175

Trp Leu Tyr Ala Gly Ile Ala Leu Ala Leu Ala Ile Gly Ser Pro Asn
            180                 185                 190

Leu Ile Tyr Gln Ala Thr His Asp Phe Pro Gln Leu Gln Met Ala Asp
        195                 200                 205

Ala Leu Gly Ala Thr Asp Gly Pro Met Asn Arg Val Ile Phe Val Pro
    210                 215                 220

Ser Leu Val Ile Leu Leu Gly Pro Val Leu Thr Val Val Trp Val Ala
225                 230                 235                 240

Gly Leu Val Lys Leu Leu Arg Asp Pro Ala Trp Arg Pro Val Arg Ala
                245                 250                 255

Leu Ala Pro Ala Phe Val Val Gly Val Ala Leu Thr Leu Tyr Gly Gly
            260                 265                 270

Gly Arg Pro Asp Tyr Val Gly Gly Phe Leu Ile Gly Leu Phe Ala Ala
        275                 280                 285

Gly Ala Val Ala Ala Asp Arg Trp Met Gly Arg Arg Thr Ser Arg Arg
    290                 295                 300

Val Leu Leu Cys Ala Gly Leu Ala Ala Ser Ala Val Leu Gln Val Leu
305                 310                 315                 320

Met Ala Leu Pro Val Leu Pro Gln Ser Ser Pro Phe Val Pro Leu Asn
                325                 330                 335

Asn Ile Ser Leu Glu Ser Val Gly Trp Pro Arg Leu Ala Glu Gln Val
            340                 345                 350

Arg Thr Ala Tyr Glu Ala Leu Pro Arg Gln Gln Arg Glu Arg Ala Val
        355                 360                 365

Val Leu Ala Asp Asn Leu Gly Glu Ile Gly Ala Leu Asp Arg Tyr Gly
    370                 375                 380

His Gly Leu Pro Ala Val Phe Ser Gly His Asn Glu Leu His Lys Trp
385                 390                 395                 400

Gly Pro Pro Pro Glu Arg Ala Asp Val Val Val Ala Val Gly Val Pro
                405                 410                 415

Arg Ser Arg Leu Ala Ala Gly Phe Thr Ser Cys Thr Val Val Gly Arg
            420                 425                 430

Val Asp Asn Gly Val Gly Val Glu Asn Ala Glu Gln Gly Arg Pro Ile
        435                 440                 445

Thr Val Cys His Gly Arg Lys Ala Ser Trp Ala Arg Leu Trp Pro Ser
    450                 455                 460

Tyr His Tyr Leu Ser Gly
465                 470


<210> SEQ ID NO 27
<211> LENGTH: 509
<212> TYPE: PRT
<213> ORGANISM: Streptomyces hygroscopicus

<400> SEQUENCE: 27

Met Thr Thr Ser Leu Asp Arg Asp Ser Arg Ala Ala Ala Ala Gly Pro
1               5                   10                  15
```

-continued

Gly Val Phe Arg Pro Ala Pro Met Ala Trp Arg Pro Val Ala Val Val
20 25 30

Val Ala Ala Leu Ala Val Leu Leu Phe Ala Phe Ala Gly Glu Tyr Gly
35 40 45

Tyr His Ala Asp Glu Leu Tyr Phe Arg Leu Leu Gly Val His Gly Phe
50 55 60

Ala Trp Gly Tyr Val Asp Gln Pro Pro Leu Leu Pro Leu Ala Val Arg
65 70 75 80

Thr Ser Met Glu Ile Phe Gly Asp Ser Met Trp Ala Ile Arg Val Pro
85 90 95

Ala Val Leu Cys Ala Ala Ala Val Thr Ala Leu Gly Ala Met Ile Ala
100 105 110

Ala Glu Leu Gly Gly Ser Arg Arg Ala Gln Thr Leu Thr Ala Phe Gly
115 120 125

Val Ala Thr Ser Thr Met Val Leu Ser Phe Gly His Trp Ile Leu Thr
130 135 140

Thr Ser Phe Asp Thr Val Ala Trp Ala Ala Val Leu Leu Phe Val Met
145 150 155 160

Arg Val Leu Leu Arg Gly Glu Ser Lys Trp Trp Leu Trp Ala Gly Val
165 170 175

Val Val Gly Val Ala Leu Tyr Ala Lys Tyr Ile Val Leu Leu Leu Pro
180 185 190

Val Ala Leu Leu Val Gly Leu Ala Leu Val Gly Pro Arg Lys Val Phe
195 200 205

Arg Asp Gly Lys Leu Tyr Ala Gly Thr Ala Leu Ala Leu Val Ile Gly
210 215 220

Ser Pro Asn Leu Ile Tyr Gln Ala Thr His Asp Phe Pro Gln Leu Gln
225 230 235 240

Met Ala Glu Gly Leu Ala Gly Thr Asp Gly Glu Ala Asn Arg Ala Met
245 250 255

Phe Ala Thr Asn Leu Ile Leu Leu Phe Gly Pro Ala Leu Phe Val Leu
260 265 270

Cys Met Ile Gly Leu Val Lys Leu Phe Arg Val Pro Glu Trp Lys Pro
275 280 285

Val Arg Thr Leu Ala Val Gly Tyr Leu Ala Ala Thr Ala Ala Ser Tyr
290 295 300

Leu Ile Glu Gly Gly Arg Pro Asp Tyr Thr Gly Gly Leu Leu Ile Ala
305 310 315 320

Leu Leu Ala Ala Gly Cys Val Thr Ala Asp Arg Trp Ala Gly Ala Arg
325 330 335

Lys Leu Arg Leu Ser Val Leu Ala Val Ser Leu Thr Leu Ser Thr Ala
340 345 350

Val Gln Met Leu Leu Ser Leu Pro Val Ile Pro Lys Ser Ser Leu Arg
355 360 365

Asp Phe Gln Ile Ala Ser Met Ala Leu Glu Thr Val Gly Trp Pro Arg
370 375 380

Leu Val Gln Gln Thr Glu Ala Ala Tyr Arg Ala Leu Pro Ala Ala Asp
385 390 395 400

Arg Asp Arg Ala Ile Val Leu Thr Glu Asn Phe Gly Glu Ala Gly Ala
405 410 415

Leu Asp His Tyr Gly His Gly Leu Pro Lys Val Tyr Ser Gly His Asn
420 425 430

-continued

```
Glu Leu Tyr His Trp Gly Pro Pro Pro Gln Arg Ala Glu Val Val Val
        435                 440                 445

Ala Val Gly Ile Asp Arg Asn Arg Leu Ser Ala Asp Phe Thr Ser Cys
    450                 455                 460

Lys Val Val Asp His Ile Asp Asn Arg Leu Gly Ile Asp Asn Pro Glu
465                 470                 475                 480

Gln Gly Val Pro Ile Thr Val Cys His Gly Pro Lys Lys Pro Trp Ser
                485                 490                 495

Ala Leu Trp Pro Thr Tyr Arg His Tyr Asn Ala Tyr Leu
            500                 505


<210> SEQ ID NO 28
<211> LENGTH: 337
<212> TYPE: PRT
<213> ORGANISM: Streptomyces hygroscopicus

<400> SEQUENCE: 28

Met Ser Thr Glu Val Ser Glu Ala Gln Ala Arg Arg Ala Val Ala Asp
1               5                   10                  15

Ile Phe Asn Ser Thr Leu Ala Ser Ser Ala Ile Gly Ala Ala Trp Glu
            20                  25                  30

Leu Gly Ala Leu Asp Glu Leu Arg Glu Asn Gly Lys Leu Asp Val Ser
        35                  40                  45

Asp Phe Ala Val Arg His Asp Leu His Glu Pro Ala Val Val Gly Met
    50                  55                  60

Phe Thr Ala Leu Ala Ser Val Gly Ile Val Arg Arg Glu Gly Ala Thr
65                  70                  75                  80

Val Val Val Gly Pro Tyr Phe Asp Glu Ala Asn His His Arg Ser Leu
                85                  90                  95

Phe His Trp Leu Asn Gln Gly Ser Gly Glu Leu Phe Arg Arg Met Pro
            100                 105                 110

Gln Val Leu Pro Asn Glu Asn Arg Thr Gly Lys Phe Tyr Gln Arg Asp
        115                 120                 125

Ala Gly Ala Ile Ser Tyr Ala Cys Arg Glu Ile Ser Glu Arg Tyr Phe
    130                 135                 140

Asp Pro Ala Phe Trp Ala Ala Val Asp Gly Leu Gly Tyr Thr Pro Thr
145                 150                 155                 160

Thr Val Ala Asp Leu Gly Ser Gly Ser Gly Glu Arg Leu Ile Gln Ile
                165                 170                 175

Ala Arg Arg Phe Pro Gly Val Arg Gly Leu Gly Val Asp Ile Ala Asp
            180                 185                 190

Gly Ala Ile Ala Met Ala Glu Lys Glu Val Ala Ala Lys Gly Phe Gly
        195                 200                 205

Asp Gln Ile Ser Phe Val Arg Gly Asp Ala Arg Thr Ile Asp Gln Val
    210                 215                 220

Ser Ala Arg Gly Glu Phe Ala Glu Val Asp Leu Leu Thr Cys Phe Met
225                 230                 235                 240

Met Gly His Asp Phe Trp Pro Arg Glu Asn Cys Val Gln Thr Leu Arg
                245                 250                 255

Lys Leu Arg Ala Ala Phe Pro Asn Val Arg Arg Phe Leu Leu Gly Asp
            260                 265                 270

Ala Thr Arg Thr Val Gly Ile Pro Asp Arg Glu Leu Pro Val Phe Thr
        275                 280                 285

Leu Gly Phe Glu Phe Gly His Asp Met Met Gly Val Tyr Leu Pro Thr
    290                 295                 300
```

-continued

Leu Asp Glu Trp Asp Gly Val Phe Glu Glu Gly Gly Trp Arg Cys Val
305 310 315 320

Lys Lys His Ala Ile Asp Ser Leu Ser Val Ser Val Val Phe Glu Leu
325 330 335

Glu

<210> SEQ ID NO 29
<211> LENGTH: 439
<212> TYPE: PRT
<213> ORGANISM: Streptomyces hygroscopicus

<400> SEQUENCE: 29

Met Asp His Glu Ser Leu His Ser Thr Leu Thr Glu Leu Ala Ala Arg
1 5 10 15

His Arg Val Pro Gly Ala Gln Leu Ala Val Ile His Glu Gly Glu Arg
20 25 30

Phe Leu Val His Thr Gly Val Cys Asp Thr Ala Ser Gly Ala Pro Val
35 40 45

Glu Arg His Thr Ala Phe Pro Val Gly Ser Leu Thr Lys Pro Phe Thr
50 55 60

Ala Ala Leu Ala Met Ile Leu Val Ala Asp Gly Asp Val Asp Leu Asp
65 70 75 80

Glu Pro Leu Arg Gly Gln Leu Pro Glu Phe Gly Ala Gly Glu Leu Val
85 90 95

Thr Leu Arg Gln Leu Leu Ser His Thr Ser Gly Leu Pro Ser Asp Val
100 105 110

Pro Glu Gly Ser Asp Glu Ala Gly Gly Gly Asp Arg Ala Arg Trp Val
115 120 125

Ala Arg Tyr Cys Arg Thr Ala Asp Leu Thr His Ala Pro Gly Thr Val
130 135 140

Phe Ser Tyr Ser Asn Ile Gly Tyr Val Val Val Gly Arg Leu Ile Glu
145 150 155 160

Ala Val Thr Gly Met Ser Trp Gln Glu Ala Ile Ser Ala Ile Leu Leu
165 170 175

Glu Pro Leu Gly Thr Arg Pro Ala Phe Val Val Gly Ala Pro Ala Thr
180 185 190

Arg Pro Val Ala Thr Gly His Ala Val Gln Ala Val Arg Asp Arg Val
195 200 205

Val Pro Ile Pro Asp Gln Asp Leu Pro Glu Val Glu Met Pro Asn Gly
210 215 220

Ala Leu Ala Leu Ser Ala Glu Asp Leu Val Gly Phe Ala Arg Leu Tyr
225 230 235 240

Phe Ala Gly Cys Pro Asp Pro Gln Pro Leu Asp Arg Ala Thr Ala Asp
245 250 255

Asp Met Cys Phe Asp Gln Leu Ala Ser Ile Ala Ile Gly Pro Tyr Gly
260 265 270

Met Ala Asp Gly Trp Gly Leu Gly Trp Ala Arg Phe Asp Asp Gly Ala
275 280 285

Ala Asp Val Tyr Gly His Asn Gly Thr Gly Asp Gly Thr Ser Cys His
290 295 300

Leu Arg Phe Asp Pro Ala Asn Gly Ser Ala Val Ala Leu Thr Ala Asn
305 310 315 320

Ala Asn Thr Gly Ala Gln Leu Trp Asp Ala Leu Val Pro Arg Leu Arg
325 330 335

-continued

```
Ala Met Gly Leu Ala Val Gly Asp Arg Pro Ala Pro Glu Pro Pro Thr
            340                 345                 350

Thr Pro Pro Pro Val Pro Asp Asp Cys Pro Gly Arg Tyr Thr Asn Gly
        355                 360                 365

Asp Thr Glu Phe Val Val Gln Pro Gly Ala Asp Gly Gly Leu Leu Leu
    370                 375                 380

Ser Phe Gly Gly Ala Pro His Ser Glu Leu Leu Cys Ser Pro Asp Leu
385                 390                 395                 400

Arg Phe Thr Met Arg Glu Leu Gly Ser Gly Ala Arg Ser Pro Gly Arg
                405                 410                 415

Phe Val Thr Asp Pro Ala Thr Gly Arg Ile Gly Tyr Leu Gln Ile Thr
            420                 425                 430

Gly Arg Leu Ala Pro Arg Arg
        435


<210> SEQ ID NO 30
<211> LENGTH: 450
<212> TYPE: PRT
<213> ORGANISM: Streptomyces hygroscopicus

<400> SEQUENCE: 30

Met Thr Thr Ala Pro Thr Asp Ala Glu Thr Ala Arg Gly Ser Ala Ala
1               5                   10                  15

Val Pro Leu Ser Arg Asn Arg Asp Tyr Asn Ile Leu Trp Ser Ser Gln
            20                  25                  30

Leu Met Ser Glu Leu Ala Met Glu Met Ala Ala Val Ala Val Pro Leu
        35                  40                  45

Leu Ile Leu Ala Arg His Gly Ser Pro Leu Gln Leu Gly Leu Ala Ser
    50                  55                  60

Ser Ala Met Ala Ala Ala His Met Ile Ser Val Val Pro Ala Gly Val
65                  70                  75                  80

Ile Ala Asp Arg Trp Asp Arg Arg Arg Leu Met Leu Gly Cys Gln Val
                85                  90                  95

Leu Arg Val Leu Gly Met Val Ser Leu Ala Gly Ala Leu Leu Leu Asp
            100                 105                 110

Arg Tyr Ala Phe Trp His Val Leu Leu Val Val Val Leu Glu Gly Phe
        115                 120                 125

Leu Gly Ser Val Phe Asp Pro Ala Glu His Ala Ala Leu Pro Gln Val
    130                 135                 140

Val Pro Pro Asp Gln Leu Ser Thr Ala Val Ala Arg Asn Ala Ala Arg
145                 150                 155                 160

Pro Tyr Ile Ala Thr Leu Val Gly Pro Gly Val Ala Gly Phe Leu Phe
                165                 170                 175

Ser Ala Leu Pro Leu Gly Pro Phe Ala Thr Asn Ala Val Met Phe Ala
            180                 185                 190

Leu Ser Ser Val Ala Leu Cys Phe Leu Arg Leu Pro Arg Gly Arg Ser
        195                 200                 205

Ala Val Val Arg Thr Gly Asp Gly Pro Asp Ser Ala Gly Ala Asp His
    210                 215                 220

Asp Arg Pro Asp His Asp Gly Arg Asp Asp Ala Asn Asp Asp Thr Ala
225                 230                 235                 240

Pro Arg Pro Gly Gly Ala Ala Gln Asp Phe Ala Ala Gly Phe Arg Trp
                245                 250                 255

Val Leu Gly Gln Pro Val Ile Arg Thr Thr Met Ala Trp Met Met Ile
```

-continued

```
            260                 265                 270

Thr Asn Leu Val Phe Ser Ser Leu Leu Ile Val Leu Leu Ala Leu Ser
        275                 280                 285

Gly Glu Asp Lys Val Gly Ala Gly Glu Leu Gly Leu Thr Met Ala Cys
    290                 295                 300

Phe Gly Ala Gly Gly Leu Leu Gly Gly Leu Phe Ala Ala Arg Met His
305                 310                 315                 320

Ala Ala Ala Arg Pro Pro Val Ile Leu Leu Gly Phe Thr Trp Thr Ala
                325                 330                 335

Ala Leu Gly Ala Ala Leu Met Ala Val Val Pro Thr Gly Leu Pro Gln
            340                 345                 350

Gly Ala Leu Leu Gly Leu Met Ala Leu Phe Ala Pro Leu Ala Asn Thr
        355                 360                 365

Thr Val Leu Thr Tyr Gln Leu Thr Val Thr Pro Asp Glu Leu Arg Gly
    370                 375                 380

Arg Met Ser Gly Val Ala Gly Phe Cys Ser Gly Gly Ala Gly Val Leu
385                 390                 395                 400

Gly Pro Ala Leu Gly Gly Ala Leu Thr Gly Ala Ala Gly Gly Gly Val
                405                 410                 415

Thr Pro Val Leu Ile Cys Ala Gly Cys Leu Val Leu Val Ala Val Ala
            420                 425                 430

Ala Thr Ala Ser Pro Thr Leu Arg Arg Phe Pro Asp Ile Ala Asp Arg
        435                 440                 445

Gln Pro
    450


<210> SEQ ID NO 31
<211> LENGTH: 408
<212> TYPE: PRT
<213> ORGANISM: Streptomyces hygroscopicus

<400> SEQUENCE: 31

Met Gln Thr Pro His Thr Pro Ser Gln Ala Gln Ser Gln Pro Arg Gln
1               5                   10                  15

Lys Pro Gln Pro Pro Ser Gln Ser Gln Ser Gln Ser Gln Pro Asn Leu
            20                  25                  30

Arg Ser Leu Thr Gly Leu Arg Phe Leu Gly Leu Leu Pro Val Phe Leu
        35                  40                  45

Thr His Ala Ala Phe Glu Gly Val Phe Ser Asp Ala Asp Val Ser Trp
    50                  55                  60

Gly Phe Leu Asp Ala Met Gly Asn Thr Gly Tyr Ala Ala Val Ser Phe
65                  70                  75                  80

Phe Phe Val Leu Ser Gly Phe Val Ile Thr Trp Ser Tyr Arg Ser Arg
                85                  90                  95

Asp Thr Thr Arg Thr Phe Trp Arg Arg Arg Ala Phe Arg Val Phe Pro
            100                 105                 110

Asn His Leu Val Ala Tyr Val Phe Ala Leu Ala Leu Met Leu Ala Ala
        115                 120                 125

Gly Ala Ala Phe Asp Ala Pro Ala Leu Ile Ser Gln Met Phe Leu Val
    130                 135                 140

His Ala Trp Val Pro Asp Pro Leu Phe Ile Asp Thr Gly Asn Thr Val
145                 150                 155                 160

Thr Trp Ser Leu Gly Val Asp Val Val Phe Tyr Gly Leu Phe Pro Val
                165                 170                 175
```

-continued

```
Leu Leu Val Leu Val Asn Lys Ile Lys Pro Thr Arg Leu Trp Tyr Trp
            180                 185                 190

Ala Gly Ala Ala Val Leu Met Val Ile Ala Ile Pro Thr Val Ala Leu
        195                 200                 205

Thr Leu Leu Pro Asp Thr Pro Ala Met Ser Val Gly Asp Val Ser Arg
    210                 215                 220

Ser Gln Tyr Trp Phe Thr Tyr Phe Phe Pro Leu Ser Arg Thr Val Glu
225                 230                 235                 240

Cys Val Leu Gly Met Leu Met Ala Arg Ile Val Leu Ser Gly Lys Trp
                245                 250                 255

Ile Gly Leu Arg Val Leu Pro Ala Ser Ala Leu Val Val Val Gly Tyr
            260                 265                 270

Val Val Ala Gln Gln Leu Pro Phe Leu Tyr Arg Leu Ser Ala Val Leu
        275                 280                 285

Ile Val Pro Ile Val Leu Leu Thr Ala Ser Val Ala Val Ala Asp Ala
    290                 295                 300

Glu Gly Arg Gly Thr Pro Leu Gly Gly Lys Val Met Val Arg Leu Gly
305                 310                 315                 320

Glu Leu Ser Phe Ala Phe Tyr Leu Val His Gln Ala Leu Leu Ala Tyr
                325                 330                 335

Gly His Ile Leu Ile Ser Pro Lys Asn Ala Gln Gly Glu Val Leu Pro
            340                 345                 350

Arg Thr Trp Asp Thr Pro Gly Gly Ile Ala Val Ile Val Leu Ser Phe
        355                 360                 365

Val Val Ser Leu Gly Leu Ala Trp Leu Leu His Asn Gly Val Glu Lys
    370                 375                 380

Pro Val Met Arg Arg Trp Ser Arg Ser Arg Arg Arg Val Thr Gln Gln
385                 390                 395                 400

Pro Pro Ala Lys Val Pro Ala Thr
                405
```

<210> SEQ ID NO 32
<211> LENGTH: 456
<212> TYPE: PRT
<213> ORGANISM: Streptomyces hygroscopicus

<400> SEQUENCE: 32

```
Val Trp Ser Ala Arg Lys Ile Ser Ala Lys Leu Arg Arg Asn Gly Gly
1               5                   10                  15

Val Arg Leu Thr Ala Ala Arg Ser Pro Arg Ala Pro Trp Met Ser Gly
            20                  25                  30

Ala Gly Asp His Ala Arg Ile Ile His Gln Pro Thr Val Val Arg Pro
        35                  40                  45

Pro Leu Arg Arg Thr Glu Pro His Arg Leu Ser Arg Ile Trp Arg Glu
    50                  55                  60

Val Arg Met Gln Thr Arg Gln Ser Asn Pro Asn Leu Arg Ser Leu Thr
65                  70                  75                  80

Gly Leu Arg Phe Val Ala Met Leu Pro Val Phe Leu Thr His Ala Ala
                85                  90                  95

Phe Glu Gly Val Phe Ser Asp Ala Lys Val Ser Trp Gly Phe Leu Asp
            100                 105                 110

Ala Met Gly Ser Thr Gly Tyr Met Ala Val Ser Phe Phe Phe Val Leu
        115                 120                 125

Ser Gly Phe Val Ile Thr Trp Ser Tyr Arg Pro Thr Asp Thr Ala Arg
    130                 135                 140
```

-continued

Lys Phe Trp Arg Arg Arg Phe Phe Arg Val Phe Pro Asn His Val Val
145 150 155 160

Thr Tyr Ala Leu Ala Leu Gly Leu Ile Ala Ala Val Gly Leu Ser Val
165 170 175

Gly Val Leu Pro Ser Val Thr Gln Leu Phe Leu Val Gln Ser Trp Val
180 185 190

Pro Asp Pro Ala Phe Thr Asp Thr Gly Asn Ser Val Ser Trp Ser Leu
195 200 205

Ala Val Asp Val Val Phe Tyr Ala Leu Phe Pro Val Leu Leu Thr Leu
210 215 220

Val Asn Lys Ile Lys Pro Asn Arg Leu Trp Tyr Trp Val Gly Gly Ser
225 230 235 240

Val Ile Gly Val Ala Val Val Pro Ala Ile Ala Leu Ala Ala Leu Pro
245 250 255

Ser Thr Pro Glu Met Pro Leu Gly Gly Val Ser Val Ser Gln Tyr Trp
260 265 270

Phe Thr Tyr Phe Phe Pro Leu Phe Arg Leu Leu Glu Cys Val Leu Gly
275 280 285

Met Leu Met Ala Arg Ile Val Leu Ser Gly Lys Trp Ile Arg Leu Arg
290 295 300

Val Leu Pro Ala Ala Val Leu Val Val Ile Ala Tyr Tyr Phe Ala Gln
305 310 315 320

Gln Val Pro Tyr Leu Tyr Arg Leu Ser Ala Val Thr Val Leu Pro Val
325 330 335

Ala Leu Leu Thr Ala Ala Ala Ala Val Ala Asp Ser Glu Gly Arg Gly
340 345 350

Thr Leu Phe Gly Ser Lys Val Met Val Trp Phe Gly Glu Leu Ser Phe
355 360 365

Ala Phe Tyr Leu Leu His Asn Leu Val Leu Lys Tyr Gly His Leu Leu
370 375 380

Leu Gly His Thr Glu Glu Glu Gly Glu Leu Val Gly His Thr Trp Gly
385 390 395 400

Val Pro Glu Gly Ile Ala Leu Ile Ala Ala Ala Phe Ala Val Ser Leu
405 410 415

Leu Leu Ala Trp Leu Leu His Asn Gly Val Glu Lys Gln Ala Met Arg
420 425 430

Arg Trp Ser Arg Arg Lys Pro Ala Pro Val Ala Glu Val Thr Ser Gly
435 440 445

Phe Tyr Ala Lys Asp Gly Ala Ile
450 455

<210> SEQ ID NO 33
<211> LENGTH: 341
<212> TYPE: PRT
<213> ORGANISM: Streptomyces hygroscopicus

<400> SEQUENCE: 33

Val Leu Thr Leu His Leu Gln Asp Asp Asp Val Ala Ala Ile Asp Ala
1 5 10 15

Val Ala Asp Glu Leu Ser Arg Arg Tyr Asp Ser Val Glu Ser Thr Glu
20 25 30

Phe Gln Ala Glu Ser Arg Leu Tyr Ala Asp Glu Leu Pro Arg Arg Val
35 40 45

Arg Arg Ala Leu His Glu Tyr Arg Ser Thr Glu Lys Ser Gly Ile Leu

-continued

```
    50                  55                  60

Val Val Thr Gly Leu Pro Val Asp Asp Ser Ala Leu Gly Ala Thr Pro
65                  70                  75                  80

Ala Asp Arg Arg His Lys Pro Val Pro Ser Thr Ser Leu Arg Gln Asp
                85                  90                  95

Ile Ala Phe Tyr Leu Ile Ala Asn Leu Leu Gly Asp Pro Ile Gly Trp
            100                 105                 110

Ala Thr Gln Gln Asp Gly Phe Ile Met His Asp Val Tyr Pro Val Gln
        115                 120                 125

Gly Phe Glu His Glu Gln Ile Gly Trp Gly Ser Glu Glu Thr Leu Thr
    130                 135                 140

Trp His Thr Glu Asp Ala Phe His Pro Leu Arg Thr Asp Tyr Leu Gly
145                 150                 155                 160

Leu Met Cys Leu Arg Asn Pro Asp Gly Val Glu Thr Thr Ala Cys Asp
                165                 170                 175

Ile Ala Asp Val Glu Ile Asp Asp Glu Thr Arg Glu Thr Leu Ser Gln
            180                 185                 190

Glu Arg Phe Arg Ile Leu Pro Asp Asp Ala His Arg Ile His Gly Lys
        195                 200                 205

Ala Pro Gly Asp Glu Ser Ala Arg Glu Ser Ala Leu Arg Glu Arg Ser
    210                 215                 220

Arg Gln Arg Val Ala Ser Ala Leu Glu Ser Pro Asp Pro Val Ala Val
225                 230                 235                 240

Leu Phe Gly Asp Arg Asp Asp Pro Tyr Leu Arg Ile Asp Pro His Tyr
                245                 250                 255

Met Gln Gly Val Gln Gly Glu Thr Glu Gln Arg Ala Leu Glu Thr Ile
            260                 265                 270

Gly Ala Ala Ile Asp Asp Ala Met Ser Gly Val Val Leu Ser Pro Gly
        275                 280                 285

Asp Ile Val Phe Ile Asp Asn Tyr Arg Val Val His Gly Arg Lys Pro
    290                 295                 300

Phe Arg Ala Arg Phe Asp Gly Thr Asp Arg Trp Leu Arg Arg Leu Asn
305                 310                 315                 320

Ile Ala Arg Asp Leu Arg Lys Ser Arg Glu Ala Arg Leu Ala Ala Thr
                325                 330                 335

Thr Arg Val Ile Tyr
            340


<210> SEQ ID NO 34
<211> LENGTH: 882
<212> TYPE: DNA
<213> ORGANISM: Streptomyces hygroscopicus

<400> SEQUENCE: 34

gtgctgagct gctactcctc ctcggtcgcg atggagatcc tctcccgctc gctgtccgag      60

acgatcgagt cggtggccct ggtccacccg accttcgaca acatcgccga cctgctgcgc     120

ggcaacggcc tgaagctggt gccgctggcg gaggacccgc tgcacggcga cgacctcgac     180

gtgagcctgc tgaagtcggt gggctgtgtc ttcctcacca cgcccaacaa ccccaccggc     240

aaggtcgtct cccgggagcg gctgacccgg ctggccgagc agtgcgccga gcacggcgtc     300

atcctcgcgc tggacacgtc cttccgcggc ttcgacaccc gcgcccacta cgaccactac     360

gaggtgctca acgccagtgg tgtgcgctgg gtggtgatcg aggacaccgg caagctgtgg     420

ccgaccctcg acctcaaggt cggcatgctc gtccactccg agaacctcgc gctgccggtc     480
```

-continued

```
gagaagatct actccgacat cctgctcggt gtctccccgc tgatcctcgc gatggtccgc    540

cgcttctccg aggacgccgc ggccggcggt ctggaggatc tgcaccgctt catcgccgcc    600

aaccgtgcca tggtgcgcgc ggaactcgcc ggtctgccgg gcgtcacggt ccccgacccc    660

gacagccggg ccagcgtcga gcgggtcgcc atcgatgacc tgacgggcac gcaggtctgg    720

gcgaagctgc gggagcacaa cgtctacgcg ctcccgtgcc gcccgttcca ctgggccaac    780

ccgtccgagg gtgaccacac cctgcggctc gcgctggccc ggtccacgga cccgctcgcc    840

cagtccgtgc gcgccctgcg ccacgtgctg aaacagcgtt ga                       882


<210> SEQ ID NO 35
<211> LENGTH: 293
<212> TYPE: PRT
<213> ORGANISM: Streptomyces hygroscopicus

<400> SEQUENCE: 35

Val Leu Ser Cys Tyr Ser Ser Ser Val Ala Met Glu Ile Leu Ser Arg
1               5                   10                  15

Ser Leu Ser Glu Thr Ile Glu Ser Val Ala Leu Val His Pro Thr Phe
            20                  25                  30

Asp Asn Ile Ala Asp Leu Leu Arg Gly Asn Gly Leu Lys Leu Val Pro
        35                  40                  45

Leu Ala Glu Asp Pro Leu His Gly Asp Asp Leu Asp Val Ser Leu Leu
    50                  55                  60

Lys Ser Val Gly Cys Val Phe Leu Thr Thr Pro Asn Asn Pro Thr Gly
65                  70                  75                  80

Lys Val Val Ser Arg Glu Arg Leu Thr Arg Leu Ala Glu Gln Cys Ala
                85                  90                  95

Glu His Gly Val Ile Leu Ala Leu Asp Thr Ser Phe Arg Gly Phe Asp
            100                 105                 110

Thr Arg Ala His Tyr Asp His Tyr Glu Val Leu Asn Ala Ser Gly Val
        115                 120                 125

Arg Trp Val Val Ile Glu Asp Thr Gly Lys Leu Trp Pro Thr Leu Asp
    130                 135                 140

Leu Lys Val Gly Met Leu Val His Ser Glu Asn Leu Ala Leu Pro Val
145                 150                 155                 160

Glu Lys Ile Tyr Ser Asp Ile Leu Leu Gly Val Ser Pro Leu Ile Leu
                165                 170                 175

Ala Met Val Arg Arg Phe Ser Glu Asp Ala Ala Ala Gly Gly Leu Glu
            180                 185                 190

Asp Leu His Arg Phe Ile Ala Ala Asn Arg Ala Met Val Arg Ala Glu
        195                 200                 205

Leu Ala Gly Leu Pro Gly Val Thr Val Pro Asp Pro Asp Ser Arg Ala
    210                 215                 220

Ser Val Glu Arg Val Ala Ile Asp Asp Leu Thr Gly Thr Gln Val Trp
225                 230                 235                 240

Ala Lys Leu Arg Glu His Asn Val Tyr Ala Leu Pro Cys Arg Pro Phe
                245                 250                 255

His Trp Ala Asn Pro Ser Glu Gly Asp His Thr Leu Arg Leu Ala Leu
            260                 265                 270

Ala Arg Ser Thr Asp Pro Leu Ala Gln Ser Val Arg Ala Leu Arg His
        275                 280                 285

Val Leu Lys Gln Arg
    290
```

<210> SEQ ID NO 36
<211> LENGTH: 1248
<212> TYPE: DNA
<213> ORGANISM: Streptomyces hygroscopicus

<400> SEQUENCE: 36
atgacgcctg tcgcagaagg aggactcccg cacggctccg tgccctcgct gtcgcacacg 60
cggcagtggc ggcccggggt cgtgcaggag gtcgccccgg ccggcgtcct cgacctgggc 120
cccggctaca tcgagccggc actcctgccc gtacgcctgc tgcggggcgc gtacgagcaa 180
gcgctggcgg agtacggcgc cgcggcgctg ggctacggtc acgacccggg cgcgcagccg 240
ctgcgcgacc ggctggccgc ccgcgccgcc gcggcggacg gcctcccctg cgacccggac 300
caggtgctgc tgacctccgg cacgtcccag gccctctatc tgctggcgac ctcgctcgcg 360
gccccgggcg acacagtgct gacggaggag ctctgttacg acctgggaca gcggatattc 420
cgggactgct cactgcggct ccgccaggtc gccatggacg ggtcggggat gctgcccgac 480
gcgctggacc gcgccctgac cgagggcgcg cgagcgggcg cgaaaaccgc tttcgtctac 540 ctcacccccca cccaccacaa ccccacgggc cacacgatgc cgctggcgcg ccgccgcctg 600
ctgctcgaag tggccgcccg gcacgatgtg ctgatcgtgg aggacgacgc ctacacggaa 660
ctgtccctga tccctgaccg cactcccccg ccctcgctgg ccgccctggc cggctaccgg 720
cgggtggtgc ggctgtgcag cttctccaag accctcggcc ccggactgcg gctgggctgg 780
ctgctcgccg accgggaact ggccggccgg ctggccacgc acggcctgtt cgtcagcggg 840
ggttcgctca accacaccac ctcgctcgcc gtgagcaccc tgctcgcgag cggcgcgtac 900
gaccgtcatc tcgacgcgtt ccgggcgcag ttgcgtgctc gtagggacgc gctcgtgggc 960
gctctacgcg cgatgctgga cgacggggtg gagctgcgca ccccggaggg cggattcttc 1020
ctgtggctgc gggccgggga cggggccgac gagcgtgagc tgctcgacgg cgccgcccgg 1080
gcgggcgtca ggatcgccgc cggatcgcgc ttcggcacaa cccagggggc cggcttgcgc 1140
ctggccttca gcttcaaccc gcccgcgtta ctggagcagg ccgccaagcg gctgaccacc 1200
gcatggtccg gcagcacgcc ggacctcgag atcggagtga gatcgtga 1248

<210> SEQ ID NO 37
<211> LENGTH: 400
<212> TYPE: PRT
<213> ORGANISM: Streptomyces hygroscopicus

<400> SEQUENCE: 37

Met Thr Pro Val Ala Glu Gly Gly Leu Pro His Gly Ser Val Pro Ser
1               5                   10                  15

Leu Ser His Thr Arg Gln Trp Arg Pro Gly Val Val Gln Glu Val Ala
            20                  25                  30

Pro Ala Gly Val Leu Asp Leu Gly Pro Gly Tyr Ile Glu Pro Ala Leu
        35                  40                  45

Leu Pro Val Arg Leu Leu Arg Gly Ala Tyr Glu Gln Ala Leu Ala Glu
    50                  55                  60

Tyr Gly Ala Ala Ala Leu Gly Tyr Gly His Asp Pro Gly Ala Gln Pro
65                  70                  75                  80

Leu Arg Asp Arg Leu Ala Ala Arg Ala Ala Ala Ala Asp Gly Leu Pro
                85                  90                  95

Cys Asp Pro Asp Gln Val Leu Leu Thr Ser Gly Thr Ser Gln Ala Leu
            100                 105                 110

-continued

```
Tyr Leu Leu Ala Thr Ser Leu Ala Ala Pro Gly Asp Thr Val Leu Thr
        115                 120                 125

Glu Glu Leu Cys Tyr Asp Leu Gly Gln Arg Ile Phe Arg Asp Cys Ser
    130                 135                 140

Leu Arg Leu Arg Gln Val Ala Met Asp Gly Ser Gly Met Leu Pro Asp
145                 150                 155                 160

Ala Leu Asp Arg Ala Leu Thr Glu Gly Ala Arg Ala Gly Ala Lys Thr
                165                 170                 175

Ala Phe Val Tyr Leu Thr Pro Thr His His Asn Pro Thr Gly His Thr
            180                 185                 190

Met Pro Leu Ala Arg Arg Arg Leu Leu Leu Glu Val Ala Ala Arg His
        195                 200                 205

Asp Val Leu Ile Val Glu Asp Asp Ala Tyr Thr Glu Leu Ser Leu Ile
    210                 215                 220

Pro Asp Arg Thr Pro Pro Pro Ser Leu Ala Ala Leu Ala Gly Tyr Arg
225                 230                 235                 240

Arg Val Val Arg Leu Cys Ser Phe Ser Lys Thr Leu Gly Pro Gly Leu
                245                 250                 255

Arg Leu Gly Trp Leu Leu Ala Asp Arg Glu Leu Ala Gly Arg Leu Ala
            260                 265                 270

Thr His Gly Leu Phe Val Ser Gly Gly Ser Leu Asn His Thr Thr Ser
        275                 280                 285

Leu Ala Val Ser Thr Leu Leu Ala Ser Gly Ala Tyr Asp Arg His Leu
    290                 295                 300

Asp Ala Phe Arg Ala Gln Leu Arg Ala Arg Arg Asp Ala Leu Val Gly
305                 310                 315                 320

Ala Leu Arg Ala Met Leu Asp Asp Gly Val Glu Leu Arg Thr Pro Glu
                325                 330                 335

Gly Gly Phe Phe Leu Trp Leu Arg Ala Gly Asp Gly Ala Asp Glu Arg
            340                 345                 350

Glu Leu Leu Asp Gly Ala Ala Arg Ala Gly Val Arg Ile Ala Ala Gly
        355                 360                 365

Ser Arg Phe Gly Thr Thr Gln Gly Ala Gly Leu Arg Leu Ala Phe Ser
    370                 375                 380

Phe Asn Pro Pro Ala Leu Leu Glu Gln Ala Ala Lys Arg Leu Thr Thr
385                 390                 395                 400


<210> SEQ ID NO 38
<211> LENGTH: 909
<212> TYPE: DNA
<213> ORGANISM: Streptomyces hygroscopicus

<400> SEQUENCE: 38

atggtccggc agcacgccgg acctcgagat cggagtgaga tcgtgacgac cagcaccggg      60

accaacggcc ggcacacggt ggccggtcca ggcagcgccg gtcccgtcgg gtacagcctg     120

ccgctctcgc cgacgggcga gtcggcgatg ctcacaccac cgccgtggca cttctccggc     180

gaggtcgtca tggtcgacta ccgcgtcgac ccggacgcgg cccgacggtt cctgccgccg     240

ggcctggagc cgggtgccga cccgggcgcc gcggcggcgg tgttcgcgac ctggcagtgg     300

tgttcgcagg acggagcgga gctgaccgac cccggtcgct gccagttcgg ggagttcctg     360

atcctgctca gctgcgagtt cgagggccgt cccatggcgc gctgcccgta cgcctgggtg     420

gaccaggccg tgcccatgat gcgcggctgg gtgcagggga tgcccaagca gttcggcgtg     480
```

-continued

```
attcaccaga gccggcccgt cacggtcggc aaggcgggct cccggctggc gcccggcggt    540

cgtttcgacg gcgcgctgtc cgtgcacgga cgacgcgtcg tggaggcctc ggtcaccgtg    600

gacaggtcga cggaccagcc gccggcgctg cacgatgttc ccctggcgca caccctggtg    660

ttcccggagt gggtgccctc cggcggcggg ccgcgaccac ggctggtcgc ctccgaggta    720

agcgatgtgg aattctcccc gatctggacc ggatcgggtg atctcacgtt ctttgacgga    780

ctgggggatg atttcggggc gctcgcaccg ttggaagtag gtagcggcca cgtgttctcg    840

tacggggaga ccttgcacgg cggccggctg ctcagcgact actcggtatc agaacgacat    900

cagccatga                                                            909
```

<210> SEQ ID NO 39
<211> LENGTH: 302
<212> TYPE: PRT
<213> ORGANISM: Streptomyces hygroscopicus

<400> SEQUENCE: 39

```
Met Val Arg Gln His Ala Gly Pro Arg Asp Arg Ser Glu Ile Val Thr
1               5                   10                  15

Thr Ser Thr Gly Thr Asn Gly Arg His Thr Val Ala Gly Pro Gly Ser
            20                  25                  30

Ala Gly Pro Val Gly Tyr Ser Leu Pro Leu Ser Pro Thr Gly Glu Ser
        35                  40                  45

Ala Met Leu Thr Pro Pro Pro Trp His Phe Ser Gly Glu Val Val Met
    50                  55                  60

Val Asp Tyr Arg Val Asp Pro Asp Ala Ala Arg Arg Phe Leu Pro Pro
65                  70                  75                  80

Gly Leu Glu Pro Gly Ala Asp Pro Gly Ala Ala Ala Ala Val Phe Ala
                85                  90                  95

Thr Trp Gln Trp Cys Ser Gln Asp Gly Ala Glu Leu Thr Asp Pro Gly
            100                 105                 110

Arg Cys Gln Phe Gly Glu Phe Leu Ile Leu Leu Ser Cys Glu Phe Glu
        115                 120                 125

Gly Arg Pro Met Ala Arg Cys Pro Tyr Ala Trp Val Asp Gln Ala Val
    130                 135                 140

Pro Met Met Arg Gly Trp Val Gln Gly Met Pro Lys Gln Phe Gly Val
145                 150                 155                 160

Ile His Gln Ser Arg Pro Val Thr Val Gly Lys Ala Gly Ser Arg Leu
                165                 170                 175

Ala Pro Gly Gly Arg Phe Asp Gly Ala Leu Ser Val His Gly Arg Arg
            180                 185                 190

Val Val Glu Ala Ser Val Thr Val Asp Arg Ser Thr Asp Gln Pro Pro
        195                 200                 205

Ala Leu His Asp Val Pro Leu Ala His Thr Leu Val Phe Pro Glu Trp
    210                 215                 220

Val Pro Ser Gly Gly Gly Pro Arg Pro Arg Leu Val Ala Ser Glu Val
225                 230                 235                 240

Ser Asp Val Glu Phe Ser Pro Ile Trp Thr Gly Ser Gly Asp Leu Thr
                245                 250                 255

Phe Phe Asp Gly Leu Gly Asp Asp Phe Gly Ala Leu Ala Pro Leu Glu
            260                 265                 270

Val Gly Ser Gly His Val Phe Ser Tyr Gly Glu Thr Leu His Gly Gly
        275                 280                 285

Arg Leu Leu Ser Asp Tyr Ser Val Ser Glu Arg His Gln Pro
```

-continued 290 295 300

<210> SEQ ID NO 40
<211> LENGTH: 216
<212> TYPE: DNA
<213> ORGANISM: Streptomyces hygroscopicus

<400> SEQUENCE: 40
gtgggcacaa accccttcga cgaccccgac ggccggtatc tggtgctggt caacgaggaa 60
gaccagcatt cactctggcc ggctttcgcc gaggtgcccc agggctggac ggtggcgctc 120
gcggaaaccg accgtcagtc cgcgctcgac ttcatcaccg agcactggac cgacatgcgg 180
ccgcgcagcc tggtgcgggc gatggaagag gcttag 216

<210> SEQ ID NO 41
<211> LENGTH: 71
<212> TYPE: PRT
<213> ORGANISM: Streptomyces hygroscopicus

<400> SEQUENCE: 41

Val Gly Thr Asn Pro Phe Asp Asp Pro Asp Gly Arg Tyr Leu Val Leu
1 5 10 15

Val Asn Glu Glu Asp Gln His Ser Leu Trp Pro Ala Phe Ala Glu Val
20 25 30

Pro Gln Gly Trp Thr Val Ala Leu Ala Glu Thr Asp Arg Gln Ser Ala
35 40 45

Leu Asp Phe Ile Thr Glu His Trp Thr Asp Met Arg Pro Arg Ser Leu
50 55 60

Val Arg Ala Met Glu Glu Ala
65 70

<210> SEQ ID NO 42
<211> LENGTH: 1266
<212> TYPE: DNA
<213> ORGANISM: Streptomyces hygroscopicus

<400> SEQUENCE: 42
gtgaccctga ccgcggcgct gaccggggcg ttcgcccccg cccgcccgtc cctcaggagc 60
gagaaggccg cccccgccgc cccccactcc ccccagtgga cagccacctg ggagccgcc 120 atgcagcagg cgacgaacga ggccacggag gacaccccga actggtcccg gcagggattc 180
aagaacgaga ccctgcgcca ggtgatccgg ctcagcgtcg gcggccccga gctccgtatc 240
cgcctctcca acgcctacgg caccaagccc ctccacatcg ccggcgccac cgtcgccagg 300
tccgacggcg aggccaaggc gcgcccccggc accgtacgca ccctcacctt ccgccatgcg 360
cccgccctca ccatccccgc gggccgcgac accgtcagcg acgcggtggc catgccgacc 420
gccaacctcg aaaaactcac cgtcaccctg cgcttcaccg cccccaccgg cccggccacc 480
atgcaccgct tcaccacggc cacgtcctac cgcgcccccg gcgaccggct acgcagcccc 540
gccgccgatg acttcaaccg ccgtgcctcg cacgcctggt actacctgac ggccgtcgat 600
gtgacccagg agccgccccg ttcggccgac tccctcatgg tcttcggcga ctccctcatg 660
gacggcgtcg gcaccagccc cgacaccgac aaccgcttct ccgacaaact cgccgaacgc 720
ctcatcgccg ccggccgccc ccagggaatg accaacgccg gcctggcggg tgaccccctg 780
ctgcacgatt ccccctgctt cggcgagaag ggcaccgccc gcttcgccaa ggaactgcgc 840
gatcgcgccg ccctgcgcac cgtcttcatc cacctcggcg ccaatgacct cgcccagtcc 900

-continued

```
cagcaggacg accccctgcac caggaaccgc cccccggtga ccgcccaaca gctcatcgac    960

ggccaccgcg ccctggtccg cgcggcccac gcccgcggta tcaaggccat cggtgtgacg   1020

atcctccccc tcaggagcgc cgtcttcccc ttcaccaccc ccgccggtga caagatccgc   1080

cggcagctca accactggat ccgcaccagc cacacctacg acgccgtcct cgacgccgac   1140

cgcgtcctga ccgaccccgc gaaccccaac cgcccccgcc ccggctacat ctcccaggac   1200

ggcctccacc ccagcgacgc cggctacctg gccctcgcct ccgccgtcga cctgaacgcc   1260

ctctga                                                              1266


<210> SEQ ID NO 43
<211> LENGTH: 421
<212> TYPE: PRT
<213> ORGANISM: Streptomyces hygroscopicus

<400> SEQUENCE: 43

Val Thr Leu Thr Ala Ala Leu Thr Gly Ala Phe Ala Pro Ala Arg Pro
1               5                   10                  15

Ser Leu Arg Ser Glu Lys Ala Ala Pro Ala Ala Pro His Ser Pro Gln
            20                  25                  30

Trp Thr Ala Thr Trp Gly Ala Ala Met Gln Gln Ala Thr Asn Glu Ala
        35                  40                  45

Thr Glu Asp Thr Pro Asn Trp Ser Arg Gln Gly Phe Lys Asn Glu Thr
    50                  55                  60

Leu Arg Gln Val Ile Arg Leu Ser Val Gly Gly Pro Glu Leu Arg Ile
65                  70                  75                  80

Arg Leu Ser Asn Ala Tyr Gly Thr Lys Pro Leu His Ile Ala Gly Ala
                85                  90                  95

Thr Val Ala Arg Ser Asp Gly Glu Ala Lys Ala Arg Pro Gly Thr Val
            100                 105                 110

Arg Thr Leu Thr Phe Arg His Ala Pro Ala Leu Thr Ile Pro Ala Gly
        115                 120                 125

Arg Asp Thr Val Ser Asp Ala Val Ala Met Pro Thr Ala Asn Leu Glu
    130                 135                 140

Lys Leu Thr Val Thr Leu Arg Phe Thr Ala Pro Thr Gly Pro Ala Thr
145                 150                 155                 160

Met His Arg Phe Thr Thr Ala Thr Ser Tyr Arg Ala Pro Gly Asp Arg
                165                 170                 175

Leu Arg Ser Pro Ala Ala Asp Asp Phe Asn Arg Arg Ala Ser His Ala
            180                 185                 190

Trp Tyr Tyr Leu Thr Ala Val Asp Val Thr Gln Glu Pro Pro Arg Ser
        195                 200                 205

Ala Asp Ser Leu Met Val Phe Gly Asp Ser Leu Met Asp Gly Val Gly
    210                 215                 220

Thr Ser Pro Asp Thr Asp Asn Arg Phe Ser Asp Lys Leu Ala Glu Arg
225                 230                 235                 240

Leu Ile Ala Ala Gly Arg Pro Gln Gly Met Thr Asn Ala Gly Leu Ala
                245                 250                 255

Gly Asp Pro Leu Leu His Asp Ser Pro Cys Phe Gly Glu Lys Gly Thr
            260                 265                 270

Ala Arg Phe Ala Lys Glu Leu Arg Asp Arg Ala Ala Leu Arg Thr Val
        275                 280                 285

Phe Ile His Leu Gly Ala Asn Asp Leu Ala Gln Ser Gln Gln Asp Asp
    290                 295                 300
```

-continued

```
Pro Cys Thr Arg Asn Arg Pro Pro Val Thr Ala Gln Gln Leu Ile Asp
305                 310                 315                 320

Gly His Arg Ala Leu Val Arg Ala Ala His Ala Arg Gly Ile Lys Ala
                325                 330                 335

Ile Gly Val Thr Ile Leu Pro Leu Arg Ser Ala Val Phe Pro Phe Thr
            340                 345                 350

Thr Pro Ala Gly Asp Lys Ile Arg Arg Gln Leu Asn His Trp Ile Arg
        355                 360                 365

Thr Ser His Thr Tyr Asp Ala Val Leu Asp Ala Asp Arg Val Leu Thr
    370                 375                 380

Asp Pro Ala Asn Pro Asn Arg Pro Arg Pro Gly Tyr Ile Ser Gln Asp
385                 390                 395                 400

Gly Leu His Pro Ser Asp Ala Gly Tyr Leu Ala Leu Ala Ser Ala Val
                405                 410                 415

Asp Leu Asn Ala Leu
            420


<210> SEQ ID NO 44
<211> LENGTH: 1632
<212> TYPE: DNA
<213> ORGANISM: Streptomyces hygroscopicus

<400> SEQUENCE: 44

atgctcaccg gtcttgcggt ggccgacttc cgcgaccggg tacgccggcc cgcgtatgtc      60

gtgatcctgg ccgcggccgt cgccctcggt tacgtggcgg tgcccgactc ggacgccaaa     120

tggatgatca tgcagatcgg tgatcaccgc gggatctaca acagcgccta cgtcggcatg     180

gtgacggccc tggccagcgg tctgtggatc accctcggcg gcttctacat cgtccgcaac     240

tccatcgaac gcgaccgcag cacccgcgtc ggccagctgc tcgccgccac cccgctgcgc     300

accaccgcgt acatgctcgg caagttcctc agcaacctca tgctgctgtc ctccatgctc     360

gtggtgctcg cgctcaccgc cctggtcatg caactggccc gcggcgagtc gcacgacatc     420

gacctgatcg ccctctggca gcccttcctc ctcatcgcgc tgccgctggt cgcgctgacc     480

gccgccctcg cgctcctctt cgaatcgctg ccgctgctgc gcaccggcct gggcaacatc     540

ctgtggttct gcatctggat ggtcgtctcg acggccggcc agggccccgg tctgcccctc     600

gacggcatcg gcgtcaacag cgtcgtccgg tcgatgtatg acgacatggt cgcccagcac     660

atcgatgtca ccggcgcgtt cagcctcggt ctgacctacc tcgacaagcc cctcgggctc     720

ttcacctggg acggcttcac gcccaccgcc ggctatgtcc tcggccgggt gacgctgctg     780

ctgatcgccg tcgtgatcgc catgctcccc gcgctgtggt tcggccgctt cgaccccgcg     840

cgaacctggc tgggccaggg gcgcaccccc gagcaggccc cggccgacgg tgtcgtccag     900

ccggtcttca tcgacgaggt cggcccgggg acgcctccgc tgtccgttca gggccatggg     960

ggagcttccc cgtcccggcc caccgtcgcc acgctgctgc gcacccgccc ggagccgggc    1020

gccgtgaccc tgcgcgtctg ggccggcgag gtccgcatcc tgctgcaagg tgtgcgctgg    1080

tggtggtgga ccggtgccgc attcctcatg atcgccgcgc tctcctcccc ggggatccac    1140

ggcatcatcc gcgtgatgct gccgctgtcc tggatctggc cggtgctgat ctggtcgcgg    1200

ctgggcaccc agcgccacga gtaccacgtc gacggcatgc tcggcgccta ccccgcggtg    1260

cgccgccggg tcttcgccga atgggccgcg ggcctgacca tcaccgccgt ggccggcatc    1320

ggtcccctga tccgcctggt ggccgccgcc gactggttcg gtctggccgg ctgggtcggc    1380

ggggccctgt tcatcccgtc cctggccctc accctgggca cgctcagccg tacccatcgc    1440
```

-continued

```
ctcttccagg cggtctacct gccgctctgg tacagcgtcg ccaacggact gccgatcttc   1500

gacttcatgg gcgcgctgcg cgacagcagc gaactggccg ccgtgcagcc gtcggtgacc   1560

gtcgtggttt ccgcggccct gatggccatc gtcttcatga ccggcgtact ccgccgcttc   1620

ggccgcgact ga                                                       1632
```

<210> SEQ ID NO 45
<211> LENGTH: 543
<212> TYPE: PRT
<213> ORGANISM: Streptomyces hygroscopicus

<400> SEQUENCE: 45

```
Met Leu Thr Gly Leu Ala Val Ala Asp Phe Arg Asp Arg Val Arg Arg
1               5                   10                  15

Pro Ala Tyr Val Val Ile Leu Ala Ala Ala Val Ala Leu Gly Tyr Val
            20                  25                  30

Ala Val Pro Asp Ser Asp Ala Lys Trp Met Ile Met Gln Ile Gly Asp
        35                  40                  45

His Arg Gly Ile Tyr Asn Ser Ala Tyr Val Gly Met Val Thr Ala Leu
    50                  55                  60

Ala Ser Gly Leu Trp Ile Thr Leu Gly Gly Phe Tyr Ile Val Arg Asn
65                  70                  75                  80

Ser Ile Glu Arg Asp Arg Ser Thr Arg Val Gly Gln Leu Leu Ala Ala
                85                  90                  95

Thr Pro Leu Arg Thr Thr Ala Tyr Met Leu Gly Lys Phe Leu Ser Asn
            100                 105                 110

Leu Met Leu Leu Ser Ser Met Leu Val Val Leu Ala Leu Thr Ala Leu
        115                 120                 125

Val Met Gln Leu Ala Arg Gly Glu Ser His Asp Ile Asp Leu Ile Ala
    130                 135                 140

Leu Trp Gln Pro Phe Leu Leu Ile Ala Leu Pro Leu Val Ala Leu Thr
145                 150                 155                 160

Ala Ala Leu Ala Leu Leu Phe Glu Ser Leu Pro Leu Leu Arg Thr Gly
                165                 170                 175

Leu Gly Asn Ile Leu Trp Phe Cys Ile Trp Met Val Val Ser Thr Ala
            180                 185                 190

Gly Gln Gly Pro Gly Leu Pro Leu Asp Gly Ile Gly Val Asn Ser Val
        195                 200                 205

Val Arg Ser Met Tyr Asp Asp Met Val Ala Gln His Ile Asp Val Thr
    210                 215                 220

Gly Ala Phe Ser Leu Gly Leu Thr Tyr Leu Asp Lys Pro Leu Gly Leu
225                 230                 235                 240

Phe Thr Trp Asp Gly Phe Thr Pro Thr Ala Gly Tyr Val Leu Gly Arg
                245                 250                 255

Val Thr Leu Leu Leu Ile Ala Val Val Ile Ala Met Leu Pro Ala Leu
            260                 265                 270

Trp Phe Gly Arg Phe Asp Pro Ala Arg Thr Trp Leu Gly Gln Gly Arg
        275                 280                 285

Thr Pro Glu Gln Ala Pro Ala Asp Gly Val Val Gln Pro Val Phe Ile
    290                 295                 300

Asp Glu Val Gly Pro Gly Thr Pro Pro Leu Ser Val Gln Gly His Gly
305                 310                 315                 320

Gly Ala Ser Pro Ser Arg Pro Thr Val Ala Thr Leu Leu Arg Thr Arg
                325                 330                 335
```

-continued

```
Pro Glu Pro Gly Ala Val Thr Leu Arg Val Trp Ala Gly Glu Val Arg
            340                 345                 350

Ile Leu Leu Gln Gly Val Arg Trp Trp Trp Trp Thr Gly Ala Ala Phe
        355                 360                 365

Leu Met Ile Ala Ala Leu Ser Ser Pro Gly Ile His Gly Ile Ile Arg
    370                 375                 380

Val Met Leu Pro Leu Ser Trp Ile Trp Pro Val Leu Ile Trp Ser Arg
385                 390                 395                 400

Leu Gly Thr Gln Arg His Glu Tyr His Val Asp Gly Met Leu Gly Ala
                405                 410                 415

Tyr Pro Ala Val Arg Arg Arg Val Phe Ala Glu Trp Ala Ala Gly Leu
            420                 425                 430

Thr Ile Thr Ala Val Ala Gly Ile Gly Pro Leu Ile Arg Leu Val Ala
        435                 440                 445

Ala Ala Asp Trp Phe Gly Leu Ala Gly Trp Val Gly Gly Ala Leu Phe
    450                 455                 460

Ile Pro Ser Leu Ala Leu Thr Leu Gly Thr Leu Ser Arg Thr His Arg
465                 470                 475                 480

Leu Phe Gln Ala Val Tyr Leu Pro Leu Trp Tyr Ser Val Ala Asn Gly
                485                 490                 495

Leu Pro Ile Phe Asp Phe Met Gly Ala Leu Arg Asp Ser Ser Glu Leu
            500                 505                 510

Ala Ala Val Gln Pro Ser Val Thr Val Val Val Ser Ala Ala Leu Met
        515                 520                 525

Ala Ile Val Phe Met Thr Gly Val Leu Arg Arg Phe Gly Arg Asp
    530                 535                 540


<210> SEQ ID NO 46
<211> LENGTH: 921
<212> TYPE: DNA
<213> ORGANISM: Streptomyces hygroscopicus

<400> SEQUENCE: 46

gtgctcgacc tcgtcaacat caccaaggtc tacaagggcg gcaagcacgc cgtggacgac      60

ctgacgatgc gtctggaacc cggcatgctc ggcctgctgg gccccaacgg cgccggcaag     120

tcgtccctca tgcggatcgc ctccacggtc acccggccca ccagcggaaa ggtcctcttc     180

cacggagagg acgcggtcgc caagcccaac gcgctgcgcc gggccctcgg ttacctcccg     240

caggacttcg gcgtctaccc gaacctgacc tcccgcgagt tcctcaggta tctggcggcg     300

gccaagggcg tctcggccaa gaccgccaag gcccgtatcg atgagctcct ggagctcgtc     360

aacctcaccg aagcggtcaa gcgtcccctg ggcaagtact ccggcggcat gctgcgccgg     420

gtcggcatcg cccaggtgct gctcgccgac ccgcaggtga tcatcgtgga cgagccgacc     480

gcggggctgg accccgagga gcgggtcagg ttccgcaatc tgctcagcga tctggcggcc     540

gacaaggtcg tgatgctctc cacccacatc gtctccgacg tcgagtcggt ggcctccgac     600

atcgcggtga tggccggcgg ccggctgcag cgccgcggca cccccgagga cctgctgcgc     660

tcggtggacg gccaggtgtg ggaggtgctg gtcgacccct cgtccgtagc ggcggtgcag     720

gcgcagtaca ccgtcagccg cctggtccgc acgaccgagg gcgtccgtat ccggctgctc     780

tcgcgcgagc tgccgtacga gggcgccgtc cagctgacgc ccgacctgga agacgcctac     840

ctcgccatca tccgtggggt cgacggcggc cgggccgccc agggcttcgg cgaacggccg     900

ctccaggcac gggtggtgtg a                                               921
```

-continued

<210> SEQ ID NO 47
<211> LENGTH: 306
<212> TYPE: PRT
<213> ORGANISM: Streptomyces hygroscopicus

<400> SEQUENCE: 47

```
Val Leu Asp Leu Val Asn Ile Thr Lys Val Tyr Lys Gly Gly Lys His
1               5                   10                  15

Ala Val Asp Asp Leu Thr Met Arg Leu Glu Pro Gly Met Leu Gly Leu
            20                  25                  30

Leu Gly Pro Asn Gly Ala Gly Lys Ser Ser Leu Met Arg Ile Ala Ser
        35                  40                  45

Thr Val Thr Arg Pro Thr Ser Gly Lys Val Leu Phe His Gly Glu Asp
    50                  55                  60

Ala Val Ala Lys Pro Asn Ala Leu Arg Arg Ala Leu Gly Tyr Leu Pro
65                  70                  75                  80

Gln Asp Phe Gly Val Tyr Pro Asn Leu Thr Ser Arg Glu Phe Leu Arg
                85                  90                  95

Tyr Leu Ala Ala Ala Lys Gly Val Ser Ala Lys Thr Ala Lys Ala Arg
            100                 105                 110

Ile Asp Glu Leu Leu Glu Leu Val Asn Leu Thr Glu Ala Val Lys Arg
        115                 120                 125

Pro Leu Gly Lys Tyr Ser Gly Gly Met Leu Arg Arg Val Gly Ile Ala
    130                 135                 140

Gln Val Leu Leu Ala Asp Pro Gln Val Ile Ile Val Asp Glu Pro Thr
145                 150                 155                 160

Ala Gly Leu Asp Pro Glu Glu Arg Val Arg Phe Arg Asn Leu Leu Ser
                165                 170                 175

Asp Leu Ala Ala Asp Lys Val Val Met Leu Ser Thr His Ile Val Ser
            180                 185                 190

Asp Val Glu Ser Val Ala Ser Asp Ile Ala Val Met Ala Gly Gly Arg
        195                 200                 205

Leu Gln Arg Arg Gly Thr Pro Glu Asp Leu Leu Arg Ser Val Asp Gly
    210                 215                 220

Gln Val Trp Glu Val Leu Val Asp Pro Ser Ser Val Ala Ala Val Gln
225                 230                 235                 240

Ala Gln Tyr Thr Val Ser Arg Leu Val Arg Thr Thr Glu Gly Val Arg
                245                 250                 255

Ile Arg Leu Leu Ser Arg Glu Leu Pro Tyr Glu Gly Ala Val Gln Leu
            260                 265                 270

Thr Pro Asp Leu Glu Asp Ala Tyr Leu Ala Ile Ile Arg Gly Val Asp
        275                 280                 285

Gly Gly Arg Ala Ala Gln Gly Phe Gly Glu Arg Pro Leu Gln Ala Arg
    290                 295                 300

Val Val
305
```

<210> SEQ ID NO 48
<211> LENGTH: 429
<212> TYPE: DNA
<213> ORGANISM: Streptomyces hygroscopicus

<400> SEQUENCE: 48

```
gtgcaccacc ccgtgactct ggaggaaccg atgttctcag gcaccatctc gaagcggccc      60
```

-continued

```
gccacactcg tcgtcgcggt ggcggccgtc gccgccaccc tcggcctctc cggctgctcc    120

gtggacgcct cgaaggcgaa gcccgaatcg aagtcgttca cgtactcggg caagtccctg    180

aaggtgacga cgcacgaggt cgccaccaag gtggtcgccg ccgaccgcaa ggacatcaag    240

gtcacccgct ggttcgactc ggccgcgggc accgagcacc tgaagtggac cctcaagggc    300

gacaccctgg acatcgacgc cggctgcagc ggtatcgcga tctgcgacgc caagttcaag    360

gtcgaggtcc ccaagggcat cgcggtgacc aaggacggcg agaagaccga cctgaccggg    420

aagagctga                                                            429
```

<210> SEQ ID NO 49
<211> LENGTH: 142
<212> TYPE: PRT
<213> ORGANISM: Streptomyces hygroscopicus

<400> SEQUENCE: 49

```
Val His His Pro Val Thr Leu Glu Glu Pro Met Phe Ser Gly Thr Ile
1               5                   10                  15

Ser Lys Arg Pro Ala Thr Leu Val Val Ala Val Ala Ala Val Ala Ala
            20                  25                  30

Thr Leu Gly Leu Ser Gly Cys Ser Val Asp Ala Ser Lys Ala Lys Pro
        35                  40                  45

Glu Ser Lys Ser Phe Thr Tyr Ser Gly Lys Ser Leu Lys Val Thr Thr
    50                  55                  60

His Glu Val Ala Thr Lys Val Val Ala Ala Asp Arg Lys Asp Ile Lys
65                  70                  75                  80

Val Thr Arg Trp Phe Asp Ser Ala Ala Gly Thr Glu His Leu Lys Trp
                85                  90                  95

Thr Leu Lys Gly Asp Thr Leu Asp Ile Asp Ala Gly Cys Ser Gly Ile
            100                 105                 110

Ala Ile Cys Asp Ala Lys Phe Lys Val Glu Val Pro Lys Gly Ile Ala
        115                 120                 125

Val Thr Lys Asp Gly Glu Lys Thr Asp Leu Thr Gly Lys Ser
    130                 135                 140
```

<210> SEQ ID NO 50
<211> LENGTH: 1173
<212> TYPE: DNA
<213> ORGANISM: Streptomyces hygroscopicus

<400> SEQUENCE: 50

```
atggattacg acgttcctcc ccggcaaaag cgccgccggt ggtgcggggt ggccgcggca     60

atgatgctcg cccccgccgt catagcgcca ccgagcgcct atctgctggc ggtcatggcc    120

gcattgacgc tggccgtatc gatacttgcc tggccgaccg gccggatctc cctggcccag    180

gcggcgggcg gcgtcgcgct gctctccctc gccgcggacg tcggctactt cgggcagccc    240

ggcctggtga tcctctggta cccgttcgag acggtcgcgc tgctcgttct cctggagcgg    300

gtggtacgtc atgtgcccag cccccgggtg ggcatcgtcg ccccgctgac cggcgcagcc    360

gtcatcctgc tgcccctgcg cttcaccctg cacgccccca ccgccgggct caaggaatcg    420

gtcttcgcgg ccttgctggc cctgatcccg gcggcctgcg cgacgggtgt ggggctctat    480

ctgcggtcgc tggacaaccg ccgggcgtat gccgtggtgc tggcgcgccg tgaacagcgc    540

ctcgaagtcg cccgcgatct gcatgacttc gtcgcccacg aggtgaccgg catcgttctg    600

gaggcccagg ccgcccaagt cagcgaggac gccgggcccg aggagcaccg cgcccttctg    660
```

-continued

```
cagcgcatcg agaaggccgg gctacgggcg ctggactcca tggaccagac ggtgacgacg    720

ctgcgcgagg cggacggccg caagtggggc gagccgccgc ccacccggct ctacggcttg    780

gccgacctcc ccgagctcgt cggccgcttc tcctccatgg ccgccgccga ggtggcgctg    840

tccctggagg acgaggtcgc cggcaccctc tcgcgggagg ccgaggacac cgcgtaccgg    900

gtggtacttg aatcgttgac caatgtccgt cggcatgcgc cgcaggccgg ccgggtccag    960

gtgttcgccg gacggaccgc cgaccgggcc gtggaggtct cggtcgccga caacgcaggg   1020

ccgggggcgt ccgccggcac ccggcagggc ggcggtacgg gcctggcggg cctcggcgaa   1080

cgcgtcagcg ccctgggcgg ctccctggag gcgggcccgt acgagaacgg gtggcgggtc   1140

aggtgcctgc tgccggcgcc cgccatccgc tga                                1173
```

```
<210> SEQ ID NO 51
<211> LENGTH: 390
<212> TYPE: PRT
<213> ORGANISM: Streptomyces hygroscopicus

<400> SEQUENCE: 51

Met Asp Tyr Asp Val Pro Pro Arg Gln Lys Arg Arg Arg Trp Cys Gly
1               5                   10                  15

Val Ala Ala Ala Met Met Leu Ala Pro Ala Val Ile Ala Pro Pro Ser
            20                  25                  30

Ala Tyr Leu Leu Ala Val Met Ala Ala Leu Thr Leu Ala Val Ser Ile
        35                  40                  45

Leu Ala Trp Pro Thr Gly Arg Ile Ser Leu Ala Gln Ala Ala Gly Gly
    50                  55                  60

Val Ala Leu Leu Ser Leu Ala Ala Asp Val Gly Tyr Phe Gly Gln Pro
65                  70                  75                  80

Gly Leu Val Ile Leu Trp Tyr Pro Phe Glu Thr Val Ala Leu Leu Val
                85                  90                  95

Leu Leu Glu Arg Val Val Arg His Val Pro Ser Pro Arg Val Gly Ile
            100                 105                 110

Val Ala Pro Leu Thr Gly Ala Ala Val Ile Leu Leu Pro Leu Arg Phe
        115                 120                 125

Thr Leu His Ala Pro Thr Ala Gly Leu Lys Glu Ser Val Phe Ala Ala
    130                 135                 140

Leu Leu Ala Leu Ile Pro Ala Ala Cys Ala Thr Gly Val Gly Leu Tyr
145                 150                 155                 160

Leu Arg Ser Leu Asp Asn Arg Arg Ala Tyr Ala Val Val Leu Ala Arg
                165                 170                 175

Arg Glu Gln Arg Leu Glu Val Ala Arg Asp Leu His Asp Phe Val Ala
            180                 185                 190

His Glu Val Thr Gly Ile Val Leu Glu Ala Gln Ala Ala Gln Val Ser
        195                 200                 205

Glu Asp Ala Gly Pro Glu Glu His Arg Ala Leu Leu Gln Arg Ile Glu
    210                 215                 220

Lys Ala Gly Leu Arg Ala Leu Asp Ser Met Asp Gln Thr Val Thr Thr
225                 230                 235                 240

Leu Arg Glu Ala Asp Gly Arg Lys Trp Gly Glu Pro Pro Pro Thr Arg
                245                 250                 255

Leu Tyr Gly Leu Ala Asp Leu Pro Glu Leu Val Gly Arg Phe Ser Ser
            260                 265                 270

Met Ala Ala Ala Glu Val Ala Leu Ser Leu Glu Asp Glu Val Ala Gly
        275                 280                 285
```

-continued

Thr Leu Ser Arg Glu Ala Glu Asp Thr Ala Tyr Arg Val Val Leu Glu
    290                 295                 300

Ser Leu Thr Asn Val Arg Arg His Ala Pro Gln Ala Gly Arg Val Gln
305                 310                 315                 320

Val Phe Ala Gly Arg Thr Ala Asp Arg Ala Val Glu Val Ser Val Ala
                325                 330                 335

Asp Asn Ala Gly Pro Gly Ala Ser Ala Gly Thr Arg Gln Gly Gly Gly
            340                 345                 350

Thr Gly Leu Ala Gly Leu Gly Glu Arg Val Ser Ala Leu Gly Gly Ser
        355                 360                 365

Leu Glu Ala Gly Pro Tyr Glu Asn Gly Trp Arg Val Arg Cys Leu Leu
    370                 375                 380

Pro Ala Pro Ala Ile Arg
385                 390

<210> SEQ ID NO 52
<211> LENGTH: 669
<212> TYPE: DNA
<213> ORGANISM: Streptomyces hygroscopicus

<400> SEQUENCE: 52
gtgactattc gcttgctgat cgccgacgac caggagatgg tccgccgcgg aatacgccgc      60
atcgtggaga gccagcccga catggaagtg gtcggcgagg cggcaaacgg cgtggacgcg     120
gtggagatgg ggcgcacgct caaacccgat gtggcgctgg tcgacatccg gatgccgcgg     180
atggacggcc tggaggtgac ccgcctgctg gccgaccccg ccgcggccaa cccggtccgg     240
gtcgtcgtgg tgacgacctt cgacctggac gagtacgtgt accccgcgct gcgcttcggc     300
gcctcggggt tcctgctcaa gcgctcgggg ccgacgctgc tggtcgaggc ggtccgggcg     360
gcgatggccg gcgacagcct gatcagcccg tcgatcactg tccggctgct ccagcatgtc     420
accggcccca cgaccggccg ccgcccccgc cgccgtgact cggtgctgac cgagcgggag     480
gtggagatcg ccgggaaggt cgccgagggc aagaccaatt ccgatatcgc ccgcgagttg     540
ttcatctccg cgggcacggt caagacccat gtcgcgagca ttcagcgaaa gctacaggta     600
cgcaatcgcg tcggggtcgc ggtgcgggcc tgggagctcg gatatgccac cgggcagacc     660
ccggggtga                                                             669

<210> SEQ ID NO 53
<211> LENGTH: 222
<212> TYPE: PRT
<213> ORGANISM: Streptomyces hygroscopicus

<400> SEQUENCE: 53

Val Thr Ile Arg Leu Leu Ile Ala Asp Asp Gln Glu Met Val Arg Arg
1               5                   10                  15

Gly Ile Arg Arg Ile Val Glu Ser Gln Pro Asp Met Glu Val Val Gly
            20                  25                  30

Glu Ala Ala Asn Gly Val Asp Ala Val Glu Met Gly Arg Thr Leu Lys
        35                  40                  45

Pro Asp Val Ala Leu Val Asp Ile Arg Met Pro Arg Met Asp Gly Leu
    50                  55                  60

Glu Val Thr Arg Leu Leu Ala Asp Pro Ala Ala Ala Asn Pro Val Arg
65                  70                  75                  80

Val Val Val Val Thr Thr Phe Asp Leu Asp Glu Tyr Val Tyr Pro Ala
                85                  90                  95

-continued

```
Leu Arg Phe Gly Ala Ser Gly Phe Leu Leu Lys Arg Ser Gly Pro Thr
            100                 105                 110

Leu Leu Val Glu Ala Val Arg Ala Ala Met Ala Gly Asp Ser Leu Ile
        115                 120                 125

Ser Pro Ser Ile Thr Val Arg Leu Leu Gln His Val Thr Gly Pro Thr
    130                 135                 140

Thr Gly Arg Arg Pro Arg Arg Arg Asp Ser Val Leu Thr Glu Arg Glu
145                 150                 155                 160

Val Glu Ile Ala Gly Lys Val Ala Glu Gly Lys Thr Asn Ser Asp Ile
                165                 170                 175

Ala Arg Glu Leu Phe Ile Ser Ala Gly Thr Val Lys Thr His Val Ala
            180                 185                 190

Ser Ile Gln Arg Lys Leu Gln Val Arg Asn Arg Val Gly Val Ala Val
        195                 200                 205

Arg Ala Trp Glu Leu Gly Tyr Ala Thr Gly Gln Thr Pro Gly
    210                 215                 220


<210> SEQ ID NO 54
<211> LENGTH: 990
<212> TYPE: DNA
<213> ORGANISM: Streptomyces hygroscopicus

<400> SEQUENCE: 54

gtgctgagga tccacttcac agttgaggac atagcaaata cgcgcatgct ggcgaccctc      60

gggccgctgg ccgagagcgc tttcgcgctc tatctgttcg gccgtaacgg cgatgtcgcc     120

tttcacgagt ggcgtcgcag tgtccgcgcc gaactcggca aggacgcggc ccgcttcacg     180

gccttgtccc agcagttccg gaccctggag gaattacctg ccgccttcgc cgacgccttc     240

acgccgggggg cggaccccga ccaggttccg tccggcgagg accggcgcgg cgccaggctg    300

ctggccgacc tgtgccgggt ggccgtgctg ccgcactgga gcctgatccg cagtcatctc     360

gacggtgcgc gcgagggctg gggcagggtg gccatctcgc acggtgtcga gcggctgctg     420

ggctccgtgc accccaaggt ccgctggcgg gcgccggtcc tcgaactgcg gcacgggccc     480

aaccgcgaca tccatctgga cggtcgcggg ttgctgctgt gcccgtcgtt cttcctgtcg     540

gagcagtcct gttcgttcgt gacggcggtc ggcaaggacg ccatgcccgc ccttgtcttc     600

cccgtgaagg cctcgtccag ggtggacatc tggggtacct cggaacacga cgagcaggcg     660

ctgggcgcac tggtcgggca caccagggcg gccgccctgg aagcgctcgc cgagggctgc     720

tccacgggcg aactcgccga ccggctgggg atctcgctgg ccggtgccag caagcatgcc     780

gcggtgctgc gacgatccgg gctggtgacc acctcccgta accgcaacac cgcgctgcac     840

gcgctcaccc ctctgggcac cgccctgctc cgcagcagcg accgcttcat ctcgccgcct     900

accgccccgg tatcgcgcgt gccggcgcaa cgcatgcggc ccttgcagct caacggcatc     960

ggccccggca ccaaccgggc ggcggtctga                                      990


<210> SEQ ID NO 55
<211> LENGTH: 329
<212> TYPE: PRT
<213> ORGANISM: Streptomyces hygroscopicus

<400> SEQUENCE: 55

Val Leu Arg Ile His Phe Thr Val Glu Asp Ile Ala Asn Thr Arg Met
1               5                   10                  15

Leu Ala Thr Leu Gly Pro Leu Ala Glu Ser Ala Phe Ala Leu Tyr Leu
```

-continued

```
            20                  25                  30

Phe Gly Arg Asn Gly Asp Val Ala Phe His Glu Trp Arg Arg Ser Val
        35                  40                  45

Arg Ala Glu Leu Gly Lys Asp Ala Ala Arg Phe Thr Ala Leu Ser Gln
    50                  55                  60

Gln Phe Arg Thr Leu Glu Glu Leu Pro Ala Ala Phe Ala Asp Ala Phe
65                  70                  75                  80

Thr Pro Gly Ala Asp Pro Asp Gln Val Pro Ser Gly Glu Asp Arg Arg
                85                  90                  95

Gly Ala Arg Leu Leu Ala Asp Leu Cys Arg Val Ala Val Leu Pro His
            100                 105                 110

Trp Ser Leu Ile Arg Ser His Leu Asp Gly Ala Arg Glu Gly Trp Gly
        115                 120                 125

Arg Val Ala Ile Ser His Gly Val Glu Arg Leu Leu Gly Ser Val His
    130                 135                 140

Pro Lys Val Arg Trp Arg Ala Pro Val Leu Glu Leu Arg His Gly Pro
145                 150                 155                 160

Asn Arg Asp Ile His Leu Asp Gly Arg Gly Leu Leu Leu Cys Pro Ser
                165                 170                 175

Phe Phe Leu Ser Glu Gln Ser Cys Ser Phe Val Thr Ala Val Gly Lys
            180                 185                 190

Asp Ala Met Pro Ala Leu Val Phe Pro Val Lys Ala Ser Ser Arg Val
        195                 200                 205

Asp Ile Trp Gly Thr Ser Glu His Asp Glu Gln Ala Leu Gly Ala Leu
    210                 215                 220

Val Gly His Thr Arg Ala Ala Ala Leu Glu Ala Leu Ala Glu Gly Cys
225                 230                 235                 240

Ser Thr Gly Glu Leu Ala Asp Arg Leu Gly Ile Ser Leu Ala Gly Ala
                245                 250                 255

Ser Lys His Ala Ala Val Leu Arg Arg Ser Gly Leu Val Thr Thr Ser
            260                 265                 270

Arg Asn Arg Asn Thr Ala Leu His Ala Leu Thr Pro Leu Gly Thr Ala
        275                 280                 285

Leu Leu Arg Ser Ser Asp Arg Phe Ile Ser Pro Pro Thr Ala Pro Val
    290                 295                 300

Ser Arg Val Pro Ala Gln Arg Met Arg Pro Leu Gln Leu Asn Gly Ile
305                 310                 315                 320

Gly Pro Gly Thr Asn Arg Ala Ala Val
                325
```

<210> SEQ ID NO 56
<211> LENGTH: 411
<212> TYPE: DNA
<213> ORGANISM: Streptomyces hygroscopicus

<400> SEQUENCE: 56

```
gtgcgggccg tgtgcgaagt cctggccggc ctcgccgagc gcacccccca gccgccgccc      60

ccggcgtccg gccgcaccgc ccaggaagcc ctgggcgcgt tcgcccgcgc atgggtcgcc     120

cggctcccgc tcgccaccga tgagcaccgg gcggccggga tcggcatggt cctgatgccg     180

gagatcctcg ccgacgcacg aacccgcctg ccgttcgccc aactgatgaa gctcaacgcg     240

atcctgctcg gactcgcccc ggagcgtctg caccggcccg aagcctccgc cccccgcctg     300

gtacgcgtcg cggaagccac ctcaccaccc tgcacggcgc gagccaactg gccgacgccg     360
```

-continued

```
cacccggctt caccgaaccc ttcgacatcg tcagcgcctg cgagcggctg a          411


<210> SEQ ID NO 57
<211> LENGTH: 136
<212> TYPE: PRT
<213> ORGANISM: Streptomyces hygroscopicus

<400> SEQUENCE: 57

Val Arg Ala Val Cys Glu Val Leu Ala Gly Leu Ala Glu Arg Thr Pro
1               5                   10                  15

Gln Pro Pro Pro Pro Ala Ser Gly Arg Thr Ala Gln Glu Ala Leu Gly
            20                  25                  30

Ala Phe Ala Arg Ala Trp Val Ala Arg Leu Pro Leu Ala Thr Asp Glu
        35                  40                  45

His Arg Ala Ala Gly Ile Gly Met Val Leu Met Pro Glu Ile Leu Ala
    50                  55                  60

Asp Ala Arg Thr Arg Leu Pro Phe Ala Gln Leu Met Lys Leu Asn Ala
65                  70                  75                  80

Ile Leu Leu Gly Leu Ala Pro Glu Arg Leu His Arg Pro Glu Ala Ser
                85                  90                  95

Ala Pro Arg Leu Val Arg Val Ala Glu Ala Thr Ser Pro Pro Cys Thr
            100                 105                 110

Ala Arg Ala Asn Trp Pro Thr Pro His Pro Ala Ser Pro Asn Pro Ser
        115                 120                 125

Thr Ser Ser Ala Pro Ala Ser Gly
    130                 135
```